US008980585B2

(12) United States Patent
Petkovic et al.

(10) Patent No.: US 8,980,585 B2
(45) Date of Patent: Mar. 17, 2015

(54) PROCESS FOR PREPARATION OF TACROLIMUS

(75) Inventors: Hrvoje Petkovic, Ljubljana (SI); Enej Kuscer, Ljubljana (SI); Stefan Fujs, Ljubljana (SI); Gregor Kopitar, Ljubljana (SI); Peter Mrak, Ljubljana (SI); Gregor Kosec, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 294 days.

(21) Appl. No.: 13/383,182

(22) PCT Filed: Jul. 9, 2010

(86) PCT No.: PCT/EP2010/059896
§ 371 (c)(1),
(2), (4) Date: Jun. 29, 2012

(87) PCT Pub. No.: WO2011/004008
PCT Pub. Date: Jan. 13, 2011

(65) Prior Publication Data
US 2012/0295316 A1    Nov. 22, 2012

(30) Foreign Application Priority Data
Jul. 9, 2009   (EP) .................................... 09165035

(51) Int. Cl.
C12P 17/16    (2006.01)
C12N 1/20    (2006.01)
C12N 15/52    (2006.01)
C12P 17/18    (2006.01)

(52) U.S. Cl.
CPC ............... *C12N 15/52* (2013.01); *C12P 17/188* (2013.01)
USPC ........................................ 435/118; 435/252.3

(58) Field of Classification Search
CPC ............................. C12N 15/52; C12P 17/188
USPC .................................. 435/118, 252.3; 536/23.2
See application file for complete search history.

(56) References Cited

FOREIGN PATENT DOCUMENTS

WO    WO 00/20601 A2    4/2000
WO    WO 03/070908 A2    8/2003
WO    WO 2006/011156 A1    2/2006

OTHER PUBLICATIONS

Motamedi et al. [Eur. J. Biochem. 244, 74-80 (1997)].*
Motamedi et al., "The biosynthetic gene cluster for the macrolactone ring of the immunosuppressant FK506", European Journal of Biochemistry, Blackwell Publishing, Berlin, DE, vol. 256, No. 3, Jan. 1, 1998 pp. 528-534.
Reynolds et al., "Rapamycin, FK506, and Ascomycin-Related Compounds", Drugs and the Pharmaceutical Sciences, Dekker, New York, NY, US, vol. 82, No. 82, Jan. 1, 1997, pp. 497-520.
Liu et al., "Role of Crotonyl Coenzyme a reductase in Determining the Ratio of Polyketides Monensin A and Monensin B Produced by Streptomyces cinnamonensis", Journal of Bacteriology, vol. 181, No. 21, Nov. 1999, pp. 6806-6813.
Molnar et al., "Organisation of the biosynthetic gene cluster for rapamycin in Streptomyces hygroscopicus: analysis of genes flanking the polyketide synthase", Gene, Elsevier Science B.V., 1996, pp. 1-7.
Schwecke et al., "The biosynthetic gene cluster for the polyketide immunosuppressant rapamycin", Proc. Natl. Acad. Sci. USA, vol. 92, Aug. 1995, pp. 7839-7843.
He et al., "Isolation and characterization of meridamycin biosynthetic gene cluster from Streptomyces sp. NRRL 30748", Gene, Elsevier Science B.V., 2006, pp. 109-118.
International Search Report in PCT/EP2010/059896 completed Sep. 28, 2010.
Cropp et al., "Genetic approaches for controlling ratios of related polyketide products in fermentation processes," Journal of Industrial Microbiology & Biotechnology, vol. 27, No. 6, pp. 368-377 (Dec. 2001); XP002561992.
International Search Report and Written Opinion dated May 11, 2010 issued in International Patent Application No. PCT/EP2010/059896.
Li at al., "Crotonyl-coenzyme A reductase provides methylmalonyl-CoA precursors for monensin biosynthesis by Streptomyces cinnamonensis in an oil-based extended fermentation," Microbiology, vol. 150, no. Part 10, pp. 3463-3472 (Oct. 2004); XP026736580.
Li et at, "High titer production of tetracenomycins by heterologous expression of the pathway in a Streptomyces cinnamonensis industrial monensin producer strain," Metabilic Engineering, vol. 11. No. 6, pp. 319-327 (Jul. 10, 2009); XP026736580.
Liu et al., "Precursor Supply for Polyketide Biosynthesis: The Role of Crotonyl-CoA Reductase," Metabolic Engineering, vol. 3, No. 1, pp. 40-48 (Jan. 1, 2001); XP001011425.
Stassi et al., "Ethyl-substituted erythromycin derivatives produced by directed metabolic engineering," Proc. Natl. Acad. Sci. USA, vol. 95, No. 13, pp. 7305-7309 (Jun. 23, 1998); XP002131683.
Sun et al., "Crotonic Acid-Directed Biosynthesis of the Immunosuppressants Produced by Streptomyces hygroscopicus var. ascomyceticus," Journal of Fermentation and Bioengineering, vol. 86, No. 3, pp. 261-265 (Jan. 1, 1998); XP000906779.
Wu et al., "The FK520 gene cluster of Streptomyces hygroscopicus var. ascomyceticus ATCC 14891) contains genes for biosysnthesis of unusual polyketide extender units," Gene vol. 251, No. 1, pp. 81-90 (Jun. 1, 2000); XP004202089.

* cited by examiner

Primary Examiner — Tekchand Saidha
(74) Attorney, Agent, or Firm — Arent Fox LLP

(57) ABSTRACT

Genetically modified strains of Streptomyces tsukubaensis (S. tsukubaensis) can be used for an improved fermentation process for the preparation of tacrolimus or a salt or derivative thereof by cultivation of these genetically modified strains. Novel genes allowing biosynthesis of allylmalonyl-CoA can be used for polyketide production with allylmalonyl extender unit.

5 Claims, 2 Drawing Sheets

SEQUENCE LISTING

```
<160> NUMBER OF SEQ ID NOS: 37

<210> SEQ ID NO 1
<211> LENGTH: 15080
<212> TYPE: DNA
<213> ORGANISM: Streptomyces tsukubaensis

<400> SEQUENCE: 1
agcacctgca ctcaacggat gaggggcctc gacagggtgt ccccgagggc gaaccgcgta     60
tcggaacagg ggtagcggat gctggaagtc tttgccggat tgagcggtgt cgtcgtactg    120
ctgggaacac gtctggcgta tcagtggatc cggggtcgga cggaggtcga gctggcccgg    180
gtggcccggg agaccgcggc cggtctgccg ccgggcagtg tgctcaccga tcggcgcccg    240
ggcagcgagc tacgggtgca gatcgggccc ggattccggg ggcagtcgca tggctgaggc    300
cccgggccac cccgccgtcc cggtggcgca gccgttacgc ccgcccgacc cggacacacg    360
gccgggcgcc gagttcgccc gctactacga acagcagatg ccccggctgc tcattcatct    420
ggtccgccgg ggggcgagct ggcacgaggc cggggaagcc gcccaggccg ccttcaccga    480
ggcgttcacc cagtgggatc gcatcgcaca ccccgccggc tggctgcggc tggtcgccta    540
ccgcctctat ctgcgccgcc ccgcacgccg ggaggagccc accgaccagc tgcccgacgg    600
gcccggaggc agctgtccgc tgcacaaggt ggaactgaag gagtccgagc agtgggtcct    660
gtccgctctg tcggccctgc cgtcgcagca gagcgcggtc atggcctggc acctcgacgg    720
cttcgccacc cgggagatcg cggaggccct cgggaccacc ccggcagcgg tacggcagaa    780
cctcgccagg gcccgcgccc ggctcaagac gatcctgctc gcacccaccg accggacagg    840
```

```
agacggaggc cgggaatgac gatccacgac gacgatgacg cagcactcga cgcgctgctc    900
gacgccgccg acgacggcct gcgcgctgcg gtcgcggcga gcctggacgc cgacgcaggc    960
cgtgccgcga tcttcacccg ggcactgccg ccccaccgcg acgcgctccc accggcggac   1020
aatatgttcg gcggccacac cacgatccac tgggccgatg cgatcgacac cgaccccac    1080
gtcagccgga tcctggagct tctgtccgag gccctgaacc gcctctcgga gctgggctgc   1140
tggctccgga ccccgggcgg cccgggaacc ccaccgggcc ggacggagac cgccgccacc   1200
ctgctgaccg ccctgtggct gggggtcaag gaacggggcg tcgaccagcc caccgcccag   1260
accttcgtgg gcgtcggcct cgacgagatc cgtgaactgc ggaacgagct gaggaggtcc   1320
gtcggatcgg ggcggcagct acggcccgat ccctgggaca gctgggacgg ccagtgggcc   1380
gacgccccact gtcaccggct gcacaccacc ctgcagaccg cccggaatct gctcccggac   1440
ctcttccgcg acggcagcga gacctcctcc gtgccctgt cgagccgttg aatccgcggc    1500
gccgcggtga ccggaaggca cccgcgggcc cgcccgtgat ctactgacag gaatcggccg   1560
cagcagcggc tgcagcgggg ctacgacagg gctacgacgg gggaacgacg cgatgttcgg   1620
attccggggg cggcggaacg atccgccggc cgagcgcgcc aggggcgggg gcgcggagct   1680
ggtcctgccg tccgccgatc cggtcgagcg ggcggaggcg ctgagctggc tccaggagca   1740
cgcgcgcgag tatctcgacc ccggtgccct cgccgaccgt gaggatctgc gccggtgacc   1800
ccctccgagc ggccggcccc cgcgctacctc gcccatacgt cactggtctg gcggctgctt   1860
ttcggcacgg tcggcggccc ctggcccgag cgggtcgccg aagggctcgt gaccatctgc   1920
cccgtcaccc atgccgaact ccggcacggt ctgcaccccg gtacggaccc cttgcccctg   1980
catctggcgc tcgaccgggc cttcggctcc gtcccgctga ggcacttcga caagcagccc   2040
gaagccgccg acgtgggcaa gcggctgcgc gcgctcggcg tcgggcagcc gccctccctg   2100
atggacatcg tgaccgcgct caccgcacgc gaccacggtc tgaccctcgt ccacaccatc   2160
gaccgcttcg acagcatcaa ccgggtgtgc cccgatatct ccctgatcaa ggtgcaggcg   2220
gcccgccctc cgcgccccga ccctcccgg acaccaacc ggcggcgggg cttcctgcgc    2280
agcctcctgg acgactgacc cggccccacc ggccccgagc ggcccctcagc ggcccggacc   2340
ccgcccccgac cggggcccgc gtacagccgc cggagtccgc ggcacgggca gcccggcggc   2400
cgacccgttc ccggacaagg gccctcccac cgcccccta ggcatctgtc ccatggtcgc    2460
ttagggggt ccggcctgcc gtcctagggg gctgacgggc cgacgaagcc ctccctatgc    2520
tcgggtcgtt cgttacgggg agacggcatc ccggagccgc cgcggccact cttcgaccac   2580
cggtgggtcc ggtacgcggc ggacccgtcc cctcgtcccg cgctaccgca cctccatccc   2640
gatcatgccc ctcctgtccg gccggagcat gtccagcggc atgtccgacg gttccccctg   2700
cccggcagga gaagcgccgg cccgagctgt ccgggcggga ccggcccggg ccatcccgac   2760
gaaaggacga tgacatgacc agtggggtgg cgttcctctt ccccggccaa gggtcgtacg   2820
taccgggcgt cttcgccggt ctgggtgccg atgccggccg ggtggcgacc ctcgtcgcgg   2880
agatcgacgc ggccgtcgag gagttccggc tgaagccggt ccggccgctt ctgttctccc   2940
cggacgctcc ggcgctggcg gagctgctcg aatccgatca cgagcggctc gacgtggcca   3000
tcctggcaac ctccatcgcc ctggcggagc ttctggagtc acggcacggg atgagtcccg   3060
accatgtcgc cggcacagt ctcggggagt tcggagccct cgccgtcgcc ggtgtcttca   3120
cccgggcga cgcggccagg gcggtctgcg aacgccacgc cacgctgcgc aaggcgccgc   3180
cgcccacggg cgggatgctg gcggtgaagg cggacgcggc ccgcgccggg gagctgatcg   3240
```

```
ctgccgcgcg ggccgggacg tcggccgtat cggcgctgaa ctcccccagc cagacggtga   3300
tcagcggcgc ggaagcggat ctggtgaagg tgcagcagct ggcacgggag gaaggcatcc   3360
gtacctcccg gctgcatgtc cccggcccct ccacgtccc gcagctggcc gacgcgagcg    3420
ccctgtacgc gacgacgatg cgcaccatac ggatatccgc gcccccggag cgcttcttct    3480
actcccacgg tctgggccgc ttcctgacgg cgcaggacga tgtcgtcgac ctgatggtga   3540
acgacatgac ccgtccggtg cggttccacg actccgtacg cgcgctgaac gcggagggcg   3600
tcacgaccta tgtggagtgc ggtgcgctgg acgtcctcac ccggatcgtg tccggatcgc    3660
tgccccgcgc cgtgaccctg gcaccgctcc gggaggccac gacgcaccg gatctgtccg    3720 cccggctgcg gcccgccggc accccggccg tgaacggcgt cgctgcgccc gcgggcccgg   3780
cgccggccgc cgaggtcgac ccggaggtgc tcgcgggggg acgtgcggtg tgcgccgagg   3840
tcctggagta tccgctggag gtgatcaccg acgacgcgga cttccaggcc gatctcggtg   3900
tcgactccct ggcgatgacc gagctgcagg cccacgcgct gcagcggttc ggtctgaagg   3960
agacgctgca ggacgcggat acgggaacgt acggcacggt ttccggtctg ccgcgtaca    4020 tcacgggcct gctgagtgag ggcaccggtt ccgtttccgg gcggcggtga tccggtcgtg    4080
atctcccgtg ctccggacgg ggaggggccg cacgacgaca gggtcgccgt cgtcgggatg   4140
ggtgtcgccg tgccgggcgc ctgcgacccg gaggagctgt ggaagctgct gtgcggtgac   4200 agaccgtgt tcgatgagcc gtcggaccgc ttccggctcg attccttctg gtccgcggat    4260
ccggccgccg aggaccgcgg ctatgtccgc acttcgggtt ttctgcacga cttccgtccg    4320 cacccccgcac tggccgcgga gatcgcggcc ggaacgctct cggccgccgc gcagaacccg   4380
gtctggctgc ggcactgcct gctgcaggcg cgggacaccg tcaccgcccg cagcaccgac   4440
cgatacgcct accacgtcgg gaccagcgcc ctggtcggcc agcgcaccga cgaggcggtg   4500
ctggccgagt gcgttccccg ggccgtcgcc gagcggctgc accgcgacga gcccgccgg   4560 atggccgagg ccgaggcacg gctgcgcgcc ctgctgagaa gccaccacgg gtacggcgcc   4620
gaagagccgc gggacacact gcccgaccgg gtcgtacggg ccgcggcggc cggactgtta   4680
cccgacgact gcgagttctc cgtggtcgac gcggcctgct cgtcctcgct gtacgcgatc   4740
ggtctgggtg tcgcgagcct gctggcgggc gcctgcgata tcgcctactg cggcggggtg   4800
tcgggagtga cgccgcgtta caacgtcacg ttctccaaac tgcacgggct gagccccagc   4860
ggcgacgtcc gcgcgttcga cgacgacgcc gacggaacgc tgttctcgga cggagcgggc   4920
gttgtcgcgc tgaagcgcct ggaccgggcc gtcgaggacg ggacccggt gttcggcgtc    4980 ctcgtgggat tcggcgggtc gtcggacggc cggggaacgg cgatctacgc ccccaacccc   5040
gtcggtcagc gccgctgcct ggaccgcgcc cggcaggcat cgggtctcac ggcggacgat   5100
gtcgactggg tcatcgcgca cgggacgggc acggccgtcg gtgacgcggt cgagctgcgg   5160
accctcgccg ccgccaccga tccgggcagc gtctggtgcg gatccaacaa gtccctgctc   5220
ggtcataccg ggtggagctc cggagtggtc tcggtcgtcc aggccctcac ggcgctgcgg   5280
cagggcacga taccggcaca gcgacgcttc accggtcccg ggctcaccgc gcagaccggc   5340 gacccgggtac gcataccttc ggcggacgtt ccctggcatg cgggcggccg gcgttccagg   5400
accgcaggcg tctccgcctt cggcttcggc ggcaccaacg cccatctgct gatcaccgac   5460
cgagagcccg tgcggacggg cccgcgcccc gcccgcaccg gcccgatcc ggtggtcgtc     5520 ctcgcctgga ccgcgcacct gcccggcgac cccgccccg aggcgacgga gcggctgctg    5580
```

```
cgcgaaggcc gcatccccgg gccgcgtacc ttcggccccc gctatccggc gccccgttt      5640 ccggacgtcc gtctccctcc gcccaccgta cggtccacgg acgcgggcca gctcatggcc     5700
ctgcgggtgg cgggcctgtt cgccgccgaa cacggtgagc tgtgggcgcc ggtacgggcg     5760
accaccgggg tcttcgcggc cgccaccggt ccgccgccgt cctccatgga tcatctggtg     5820
cgctgtcatg ccgccgacgt acaccgcatt ctcgacgaac ccgaccggac ggcgttcacc     5880
gaatggctcg ccgacctgcg ggccacgacc ccggcgacca ccaaggacac gctgccgggg     5940
ctgctgccca acatcatccc ggcgcgtatc gccaaccgct acgacctggg cggccccacc     6000
atgctggtcg acacgggcac caccagcggg ctcaccgccg tgcacaccgc cgtccgccaa     6060
ctggcggccg gtgccgtcga catggcgctc gtcctcggtg tcagcgcgac cggccgaccc     6120
gagttcgccc gcttcatggg cgtcgcggcc gagcggatcg cggaggggc gttcctcctc      6180 gcgctgagtc gcgagtccgt cgccctcgcg cacggcctga ccccctcgt ccgcctccgc      6240 acggactgga ccggcagccc tcaggcgtct gcggatgccg tccccggcgg gcccggtgcg     6300
gcggaggaca ccttcctcgg cgccgacggc gtcctcgccg tgatccgtgc cctgcactcc     6360
accgcgtccg gcgtcaccgt gggacccgcg gacggcgaac cgggcccggt gatcaccctc     6420
tcccccgccg acggctcacc tcttcggcag acaaggacca gccgatgacc cacgttcgcg     6480
acgccgcggc caccgacgac ccgcaggcca tcgccgcctg cgaggtcccg gccggctacc     6540
gggccgccgt tgtcctcgcg gccgaccacc aggcactcgc cggagccccc gtcgaagacc     6600 gggaccccg caagacggtc caggtccagg aggtccccac ccccgaaccg gaccacggcg      6660
aggtgctcat cgccaccatg gcgagctcca tcaactacaa caccgtgtgg tcggcgctct     6720
tcgagcccgt tcccaccttc cgcttctgc gcaccctcgg ccgtacctca ccggaggcgg     6780
cccgccacga ccagccgtac cacgtgctcg gctccgacct gtccggagtg gtgctgcgca     6840
ccggaccggg tgtacgggag tggaagcccg gcgacgaagt cgtcgcgcac tgtctgcaac     6900
cggacctgca gacgccgggc gggcacgacg acaccctgct cgaccccggc cagcgggtct     6960
ggggctacga gacgaacttc ggcggcctcg ccgaactctc cctggtcaag gcgaaccagc     7020
tgatgccgaa gcccgcccat ctcacctggg aggaggcggc ctcccgggg gtggcgctct     7080 ccacggccta ccgtcagctg gtgtcccacc acggggcggc gatgaagcag ggcgagcgcg     7140
tcctggtctg gggtgccgcc ggtggcgtcg gcgcctacgc gacccagctg gccctcaacg     7200
gcggcgccgt tccgatctgt gtggtgtcgt cgcaggccaa ggccgacctg tgccggcaga     7260
tgggcgcgga gctcgtcatc gaccgtgctc cggagggctt ctcgttctgg gaggggcggg     7320
accgcccgcg gctgagcgag tggagccgct tccgcggtgc cgtccggtcc ctggcgggtg     7380
acgaccggga tcgtcatc gagcaccccg gccgggacac cttcggcgtc agcgtcatga      7440
tcgccgcccg gggcggaaag gtggtcacct gcgcatcgac caccggctac cagcacacct     7500
acgacaaccg ccatctgtgg atgcgcgtca acgcatcat cgggtcacat atggcgaact     7560
accgggaagc ctgggccgcg aacgaactcg tcgcacgcgg cagcatccac cccgtgctct     7620
cccgggtcta ccccctcgac gccacaggcg acgccacgca cgccgtcgcc aacaacagcc     7680
accacggcaa ggtgggcgtg ctctgcctcg ccgaccgccc cggcatggga gtgcgcgacc     7740
ccgagctgcg ggcccggaaa ctcgacagca tcaacctgtt ccggaagggg cagccccggt     7800
gagcgaatcc gaacgcctcg gtatcgtcag ggatttcgtc gcccgggaga tcctgggccg     7860
cgaaggcatc ctcgactcgc tggcggacgc accactgggc ctgtacgaac gcttcgccga     7920
gacgggcctg atgaactggt gggtccccaa ggagcacggc ggtcttgggc tcggcctgga     7980
```

```
agagagtgtg cggatcgtct ccgaactcgc ctacggggac gccggggtgg cgttcaccct   8040
gtttctgccc gtcctgacga ccagcatgat cggctggtac ggcagcgagg agctcaagga   8100
gagattcctc ggccctctcg tggcccggcg gggcttctgc gccacgctgg gcagcgagca   8160
cgaggccggc agcgaactgg cccggatctc caccacggtc cgccgtgacg cgacacgct    8220 ggtactcgac ggcaccaagg ccttctccac cagcaccgac ttcgcccggt tcctcgtcgt   8280
catcgcccgt tcggcggacg acccggcccg gtacacggcg gtcaccgtac cgcgggacgc   8340
gccggggctg cgggtcgaca aacgctggga cgtcatcggg atgcgcgcct ccgcgaccta   8400
tcaggtgtcg ttctccgact gccgggtgcc ggggacaac gcgctgaacg gcaatgggct    8460
gcggctgctg gagatcggcc tcaacgccag cagaatcctg atcgccgcat ccgctctggg   8520
tgtcgcccgc aggatccgcg atgtgtgcat ggagtacggg aagacgaagt cgctcaaggg   8580
cgctccgctc gtcaaggacg gcgtgttcgc cgggcggctc ggccagttcg agatgcagat   8640
cgacgtgatg gcgaaccagt gcctggcggc cgcacgggcc tacgacgcga ccgcggcccg   8700
gcccgacgcc gccagggtgc tgctgcggca gggcgcccag aagtcggcac tgaccgcgaa   8760
gatgttctgc gggcagacgg cctggcagat cgcgtccacc gcgtcggaga tgttcggcgg   8820
catcgggtac acgcacgaca tggtgatcgg gaagctgctg cgggatgtgc ggcacgcttc   8880
gatcatcgag ggcggcgacg acgtcctgcg cgatctcgtc taccagcgct tcgtcgtccc   8940
caccgcgaaa cgtacctagg gcatgttctg gtcagtcccg cgtcagggcc tgggtgaggt   9000
cggcccacag atcgtcgacg tgttcgaggc cgacggagat ccggagcagt cggtcggaga   9060
taccggcctg ttcgcgtgag cccgggtcca tggcgtggtg ggtgagcgag accgggtgct   9120
gaatgaggct gtcgacgctg ccgaggctga ccgccgggt gaagagacgt acgccgccgg    9180
tcaccgcgtg cggatcgtcg acctcgaagg acacgattgc cccgcctgcg gccatctgct   9240
tcggcggccg gggttcaccg ctcagccccg ggtagtggac cctggtgacc gccggatggt   9300
gcaggagccg gcgggcgatc tcggcagccg aggccgaagc gtggtgcatc cgcaccgaga   9360
gcgtcgacag tcctctgagg agctggtagc cagccagggg gtgcaggatc cctccggtgg   9420
cgaaccggat ccgccgcagg gcacgggcga actcctcgtt cgacgccacc acaccgccca   9480
tgacgtcacc gtggccccc aggtacttcg tcgcgctgtg cagaacgatg gcggcacccc    9540
tgttcagggg gcgctggagc gcgggcgttg cgaaggtgtt gtcgaccagt accggaaccg   9600
gagcgcatgc agcggccagc gcctggatgt cggtctccgt cagtgtgggg ttggcgggtg   9660
actcgacgat caccagcccc gtgtcgctgc ggatggcatc gccggcgctg tggggttgcg   9720
cccaggtcac cgaggtgccc agcaggcccg agtccaggag gtagtcgctg gtgccgtaca   9780
ggggacggac ggcgacgata tgcggccgtc cccgggcgac ctgcacgaga aggcaggcgc   9840
agagcgctgc cataccgctg gcgaaggcca ccgcggcttc ggccccttcc agttcggcca   9900
gcgcggactc gaaccgtgcg acggtggggt tccctgcccg gccgtagatc ggcggaccgc   9960
cgtcgtcggc tccggagccg aacacgtcga tccgcgccgc ctcggcaacg tgtcgcgg   10020 aggggtaggt ggtggacagg tctatgggcg ggacatgcag tccgagatcg acaagatcct   10080 cacgccggc atgaccgcc cgggtttccc agtgatgcga aggcatgacg acagtcttcg      10140
caaagcgtca ggatcagtga ctgaatctcg cactacattc ggtccatgaa agaaaaggtt   10200
gtcctggatt cgatagatca ggcaattctg cgtgagctgc agaatgatgg tcggctgccc   10260
aacaagacgc tggcccggag ggtcggcgtg gcaccgtcca cctgtctggc ccgcacgcag   10320
```

```
aggctgatgg aggcaggtgt gatcagaggt ttccaggctc aggtgagtgc cgcggcgatc   10380
ggccggcagg tccaggccgt cctcgccgtc cagttcatcg cccattcacg tccctttgtc   10440
gacccgttcg tggcatgggc cagggagcgg cccgagactc gtgcgcttca ccatgtgacc   10500
ggagccttcg acttcctcgt ccacacggcc tgccgtgaca ccgagaacct ccagcaactc   10560
gtcctggagt tcaccgcacg ccgagaggtg ggccgagtgg agacccacct cgtattcgga   10620
tcctggtcgg gaggacccct gactccgggc tagtgatctg aatcggagat tcgtcggcag   10680
gtcgggcggg cgccgatgtc ccgccggtac agtcgccacc gtcgttccat ccaccctctg   10740
tctccaagga gacctcgtgg accgagaacc cgttttcgtc ctcgacccgc gcggcggcga   10800
tcgccatggc gaggacgccg ccctccgcgc ccgcggcccc ctgacccgag tcgacgccct   10860
cggcgtggag gcgtggtcgg tcaccgaccc ggtgctgctc cgtcggctgc tgctggactc   10920
gcgggtctcc aaaaacgccc ggcaacactg gcccgccttc ccggaggaga tcgtcggagt   10980
ctggccgctc gccctctggg tcgccgtgga gaacatgttc accgcctatg gcgaggagca   11040
ccgacggctg cggcggacca tcgggccggc cttcgccgcc cgcaggatca acgcgctggc   11100
gccggtcatc gagcagctcg tgggggagct gctggacgag ctcgccgcca ccccgcccgg   11160
agagccggtc gacctgcggg agcacttcgc ctatccgctg cccatcgggg tcgtcggcca   11220
gctcgccggc ctccccgaat ccgtccggcc ccggttccgc cgtaccgtcg acgtgatctt   11280
ctccaccagc cacagccccg aggagacgac cgccgcggtc caggatctgt acgcgctcct   11340
cgccgacctc gtggccgcca agcgcgccga gccgggagac gacctcacgt cggcgctcat   11400
cgccgccagg gatacggaag gcgacggaga gccctgacg gaggccgaac tcgtcgacac   11460
cctgctgctg gtggtcaacg ccggtttcga aaccaccgtc aacctcctgg accaggcgat   11520
caccgcactc ctcaccgacc ccgggcaact cgcccatgtc cgcgccggac gcgcgggctg   11580
gaaggacgtg gtcgaggaat cactccgcca cgaggcccccg ctcgcgcatc tgccgatgcg   11640
cttcgccgtg gaggacatcc ccctccccga acacggcgtg accatccggc agggcgacgc   11700
cgtcctgccc gcctacgccg ccgccaaccg gcatccggac ctgcacggcc tcaccgccga   11760
cgacttcgac gccacccgga gcgacaagag ccatctctcc ttcggacacg gcatgcacct   11820
ctgcctcgga gccgccctcg gtcgcctcga agccgaaatc gccctgcgcg gcctcttcga   11880
acgcttcccc cgtctcgccc tcgccgtgcc cctggaccga ctgcgcccca agccgagctt   11940
catctccaac ggccacagcg aactgcccgt catcatcgac ccgtagcccc cggccgacgg   12000
cagggatgtc cgctctcaac agcacggggga tactctgatg aaccgcttcg cctcggacga   12060
ggggctggac gacagagtcg cctactgact gcgaaggact tggaagcaca ccgagccgcc   12120
gccccctccg ccccgtaccg gggcggcacg acgaaagggc agggacgact gtgggcactc   12180
ctcaacccga tgtcgccgag ggcctcacgc cggtcgaggc ggcgcgctca ctggtcccgc   12240
tgctcgctgc cgaagcggcc cgcaccgagg agcggcgcgc cctcaccggc gccactgtga   12300
ccggcctgcg ccgggccggt ctgctccgcc tcggaccccc gaccgagtgc ggcggccggg   12360
gtgcgggtgc ccgtaccgcg gtggatgtgt gcgaggagct ggccaagggc tgtgcgtccg   12420
cctcctggat cgtgggcatc gcctacgcg gcgccctctt cgcctcccag cttccccact   12480
ccgagcgtgc ggccctgtgg cgggacgacc cggacgctgt cgtctgcggc agcgccaacc   12540
cgtccggaac ggcgcggcgt acggacggcg gctggaccct gagcggccgt tggccctgga   12600
tctccggcat ccaccatgcg ccctggaccc tgctcggctt cgtccggccc ggcgcagggg   12660
gcgaaccgga gcgcggcatg gccgtggtcc ccaccgccgg cctgaccgtc gaggacgtct   12720
```

-continued

```
ggcatatggc gggcatgcgc ggcaccggca gcgacacggc cgtcgcggac ggcgtgtacg   12780
tgccggactc ccgcacgatc tccctgaccg ccatggcgga cggcgcctac cggcgacgcc   12840
atcccggcga accccgggtc accttccatc tctccatcaa cctgccgttg gtggcgacgg   12900
ccgtcgggat cgccacagcg tccctggaga aggtgctgga tgccgcggcc cggggcaaac   12960
agacggtctc cccgctgcac cggctggtcg ccgaggactc cgcccatcag ctcaatgtgg   13020
cggacgccgc gacgctcatc gacacggccc ggctgcatct gccgcgcgcc gccgacgagg   13080
tggactccca cgcccgcgcg gggcgccgtc ccgcgctcgc cgagcgggcc cgactgcgga   13140
tggacgccgc ccacgccatg cgctgcgccc gcgacgccgt gagcctgctg ctggacaccg   13200
cgggcgcggg cagcttcgcg gacggctcgg tcctgcaacg ggcctggcgc gatatcgaga   13260
cggcgtcccg gcacgccgcg ctcagcgtcc agaccagcaa ggagatatac ggccgcgctc   13320
tgctcggcgc cccgctgccg cccggcccgg tcgtctgagg ggggccacga tgacgacggc   13380
aggcctccgg gtggcgctgg tcaccggcgc gggacgcggg atcggggggcc gcgatcgccg   13440
```

```
aacggctgca cgggtccggc caccgggtgg ccctgctgga ccgcgacggc gacgccgtga   13500
ccgggctgtc cgccgccctc gaccccgccg gcgcgggcac cgcgctgccg ctgcgtgcgg   13560
acgtcgacga cacggacgcc gtccacgccg cgctgcgcga gaccgccgcc gcctggcacg   13620
cgcccgacat cctgatcaac aatgccgccc ggaccgcccc cggctcggta tgggacatcg   13680
aaccggacga atgggacgcc gtactgacga ccaatctgcg cagcgtcctg accctgaccc   13740
ggctgtgcgc gcccgcgatg cgcgaccgcg gctggggccg ggtggtcaac ctctcctcgc   13800
tggccggtca gcagggcggc accctcgccg gcgcccacta ctccgccgcc aaggcgggcg   13860
ttctcgtgct gaccaaggtg ttcgcccgtg aactggcggc gcacggcgtg accgtcaacg   13920
cggtagcccc ggccgccgtc gacacccggg cggtcgccgg gctcggcccg tcggcggtgg   13980
ccgaggcggc ccggcagatc ccggtggggcc ggatggggag gccttcggag gtcgccggcc   14040
tcgtggccta tctggtgggc gaagagggcg gatacgtcac cggcgccacc ttcgacatca   14100
acggcggcac ccatatgcgc tgacgcggcc ccgcgccctg cgatcgcgat gccgcccccg   14160
aggcgccgct ggaccgtgtg gtcccgggtg ggtcccggcg ccgcaccgct accccccctcc   14220 ccaccccccct ggaccccccct gacccggggg tccgggccgg gaggggggacg ggacgcccgc   14280 ctagcattcc gggcatggcg aatcaggtga ccatgtccga cgcgctgctc gcttacgtcc   14340
ggaaggtgtc actgcgggac gacagggtgc tgggcggtct gcgggcggag tcggcagggc   14400
tgccgggggg caacgctctg ccggtatccg ccgaagaggg ccagttcctg gaattcctgg   14460
tgcggttgac cggcgcccgt caggtgctgg agatcgggac gtacaccggc tacagcaccc   14520
tctgtctggc ccgcgggctg ccgccgggg cccggtggt gacgtgcgac aacacggcga   14580
agtggccgga ggtgggcagg ccgtactggg agcgggccgg ggtggccgaa cggatcgacg   14640 tacgatcgg cgacgccctg gacgtgctgg ccggactccg cgacgagccg ggcgcgggac   14700
cggggtcgtt cgatgtcgtg ttcatcgacg ccgacaagga acgctatccg gcctactacg   14760
aggcggctct gccgctggtg cgcggcggtg gcctgatcgt cgtcgacaac acgctgttct   14820
tcggacgggt ggccgacgac gcggtgacgg acccggagac gacagcgatc cgcgcactca   14880
atgcggggct gcgcgacgac gatcgggtgg acctggccat gctggcgtcg gccgacggca   14940
tcaccttgtt gcgaagcgg tgaacgggat actgccgcg gcggtcagtg tcagggtcct   15000
cggcccgggt cgcggcgagg gctccagatg cagccgttcc acaccaccgg ccggctcccc   15060
```
cagcggcgac gcgcaggcgc                                               15080

<210> SEQ ID NO 2
<211> LENGTH: 1293
<212> TYPE: DNA
<213> ORGANISM: Streptomyces tsukubaensis

<400> SEQUENCE: 2
atgaccagtg gggtggcgtt cctcttcccc ggccaagggt cgtacgtacc gggcgtcttc      60
gccggtctgg gtgccgatgc cggccgggtg cgacccctcg tcgcggagat cgacgcggcc     120
gtcgaggagt tccggctgaa gccggtccgg ccgcttctgt tctccccgga cgctccggcg     180
ctggcggagc tgctcgaatc cgatcacgag cggctcgacg tggccatcct ggcaacctcc     240
atcgccctgg cggagcttct ggagtcacgg cacgggatga gtcccgacca tgtcgccggg     300
cacagtctcg gggagttcgg agccctcgcc gtcgccggtg tcttcacccc gggcgacgcg     360
gccagggcgg tctgcgaacg ccacgccacg ctgcgcaagg cgccgccgcc cacgggcggg     420
atgctggcgg tgaaggcgga cgcggcccgc gccggggagc tgatcgctgc cgcgcgggcc     480
gggacgtcgg ccgtatcggc gctgaactcc ccagccaga cggtgatcag cggcgcggaa      540
gcggatctgg tgaaggtgca gcagctggca cgggaggaag catccgtac ctccccggctg     600 catgtccccg gccccttcca cgtcccgcag ctggccgacg cgagcgccct gtacgcgacg     660
acgatgcgca ccatacggat atccgcgccc gggagcgct tcttctactc ccacggtctg      720
ggccgcttcc tgacggcgca ggacgatgtc gtcgacctga tggtgaacga catgacccgt     780
ccggtgcggt tccacgactc cgtacgcgcg ctgaacgcgg agggcgtcac gacctatgtg     840
gagtgcggtg cgctggacgt cctcacccgg atcgtgtccg atcgctgcc ccgcgccgtg      900 accctggcac cgctccggga ggccacgacg acaccggatc tgtccgcccg gctgcggccc     960
gccggcaccc cggccgtgaa cggcgtcgct gcgcccgcgg gccggcgcc ggccgccgag     1020 gtcgacccgg aggtgctcgc gggggtacgt gcggtgtgcg ccgaggtcct ggagtatccg    1080
ctggaggtga tcaccgacga cgcggacttc caggccgatc tcggtgtcga ctccctggcg    1140
atgaccgagc tgcaggccca cgcgctgcag cggttcggtc tgaaggagac gctgcaggac    1200
gcggatacgg gaacgtacgg cacggttttcc ggtctggccg cgtacatcac gggcctgctg    1260
agtgagggca ccggttccgt ttccgggcgg cgg                                 1293

<210> SEQ ID NO 3
<211> LENGTH: 2388
<212> TYPE: DNA
<213> ORGANISM: Streptomyces tsukubaensis

<400> SEQUENCE: 3
gtgatctccc gtgctccgga cggggagggg ccgcacgacg acagggtcgc cgtcgtcggg      60
atgggtgtcg ccgtgccggg cgcctgcgac ccggaggagc tgtggaagct gctgtgcggt     120
gacagacccg tgttcgatga ccgtcggac ccgcttccggc tcgattcctt ctggtccgcg     180
gatccggccg ccgaggaccg cggctatgtc cgcacttcgg gttttctgca cgacttccgt     240
ccgcaccccg cactgccgc ggagatcgcg ccggaacgc tctcggccgc cgcgcagaac       300
ccggtctggc tgcggcactg cctgctgcag gcgcgggaca ccgtcaccgc ccgcagcacc     360
gaccgatacg cctaccacgt cggggaccagc gccctggtcg gccagcgcac cgacgaggcg     420
gtgctggccg agtgcgttcc ccgggccgtc ccgagcggg tgcaccgcga cgagcccgcc      480
cggatggccg aggccgaggc acggctgcgc gccctgctga gaagccacca cgggtacggc     540

```
gccgaagagc cgcgggacac actgcccgac cgggtcgtac gggccgcggc ggccggactg      600
ttacccgacg actgcgagtt ctccgtggtc gacgcggcct gctcgtcctc gctgtacgcg      660
atcggtctgg gtgtcgcgag cctgctggcg ggcgcctgcg atatcgccta ctgcggcggg      720
gtgtcgggag tgacgccgcg ttacaacgtc acgttctcca aactgcacgg gctgagcccc      780
agcggcgacg tccgcgcgtt cgacgacgac gccgacggaa cgctgttctc ggacggagcg      840
ggcgttgtcg cgctgaagcg cctggaccgg ccgtcgagg acggggaccc ggtgttcggc       900
gtcctcgtgg gattcggcgg gtcgtcggac ggccggggaa cggcgatcta cgcccccaac      960
cccgtcggtc agcgccgctg cctggaccgc gcccggcagg catcgggtct cacggcggac     1020
gatgtcgact gggtcatcgc gcacgggacg ggcacggccg tcggtgacgc ggtcgagctg     1080 cggacccctcg ccgccgccac cgatccgggc agcgtctggt gcggatccaa caagtccctg    1140
ctcggtcata ccgggtggag ctccggagtg gtctcggtcg tccaggccct cacggcgctg     1200
cggcagggca cgataccggc acagcgacgc ttcaccggtc ccgggctcac cgcgcagacc     1260
ggcgaccggg tacgcatacc ttcggcggac gttccctggc atgcgggcgg ccggcgttcc     1320
aggaccgcag gcgtctccgc cttcggcttc ggcggcacca cgcccatct gctgatcacc      1380 gaccgagagc ccgtgcggac gggcccgcgc cccgcccgca ccgggcccga tccggtggtc     1440
gtcctcgcct ggaccgcgca cctgcccggc gaccccggcc cgaggcgac ggagcggctg      1500 ctgcgcgaag gccgcatccc cgggccgcgt accttcggcc ccgctatcc ggcgccccg       1560 tttccggacg tccgtctccc tccgcccacc gtacggtcca cggacgcggg ccagctcatg     1620
gccctgcggg tggcgggcct gttcgccgcc gaacacggtg agctgtgggc gccggtacgg     1680
gcgaccaccg gggtcttcgc ggccgccacc ggtccgccgc cgtcctcat ggatcatctg      1740 gtgcgctgtc atgccgccga cgtacaccgc attctcgacg aacccgaccg gacggcgttc     1800
accgaatggc tcgccgacct gcgggccacg accccggcga ccaccaagga cacgctgccg     1860
gggctgctgc ccaacatcat cccggcgcgt atcgccaacc gctacgacct gggcggcccc     1920
accatgctgg tcgacacggg caccaccagc gggctcaccg ccgtcacac cgccgtccgc      1980 caactggcgg ccggtgccgt cgacatggcg ctcgtcctcg gtgtcagcgc gaccggccga     2040
cccgagttcg cccgcttcat gggcgtcgcg gccgagcgga tcgcggaggg ggcgttcctc     2100
ctcgcgctga gtcgcgagtc cgtcgccctc gcgcacggcc tgaccccct cgtccgcctc     2160 cgcacggact ggaccggcag ccctcaggcg tctgcggatg ccgtccccgg cgggcccggt     2220
gcggcggagg acaccttcct cggcgccgac ggcgtcctcg ccgtgatccg tgccctgcac     2280
tccaccgcgt ccggcgtcac cgtgggaccc gcggacggcg aaccgggccc ggtgatcacc     2340 ctctccccg ccgacggctc acctcttcgg cagacaagga ccagccga                  2388
```

<210> SEQ ID NO 4
<211> LENGTH: 1335
<212> TYPE: DNA
<213> ORGANISM: Streptomyces tsukubaensis

<400> SEQUENCE: 4

```
atgacccacg ttcgcgacgc cgcggccacc gacgacccgc aggccatcgc cgcctgcgag       60
gtcccggccg gctaccgggc cgccgttgtc ctcgcggccg accaccaggc actcgccggg      120
agccccgtcg aagaccggga cccccgcaag acggtccagg tccaggaggt ccccacccccc    180 gaaccggacc acggcgaggt gctcatcgcc accatggcga gctccatcaa ctacaacacc     240
```

```
gtgtggtcgg cgctcttcga gcccgttccc accttccgct ttctgcgcac cctcggccgt    300
acctcaccgg aggcggcccg ccacgaccag ccgtaccacg tgctcggctc cgacctgtcc    360
ggagtggtgc tgcgcaccgg accgggtgta cgggagtgga agcccggcga cgaagtcgtc    420
gcgcactgtc tgcaaccgga cctgcagacg ccgggcgggc acgacgacac cctgctcgac    480
cccggccagc gggtctgggg ctacgagacg aacttcggcg gcctcgccga actctccctg    540
gtcaaggcga accagctgat gccgaagccc gcccatctca cctgggagga ggcggcctcc    600
ctgggggtgg cgctctccac ggcctaccgt cagctggtgt cccaccacgg ggcggcgatg    660
aagcagggcg agcgcgtcct ggtctggggt gccgccggtg cgtcggcgc ctacgcgacc    720 cagctggccc tcaacggcgg cgccgttccg atctgtgtgg tgtcgtcgca ggccaaggcc    780
gacctgtgcc ggcagatggg cgcggagctc gtcatcgacc gtgctgcgga gggcttctcg    840
ttctgggagg ggcgggaccg cccgcggctg agcgagtgga gccgcttccg cggtgccgtc    900
cggtccctgg cgggtgacga cccggacatc gtcatcgagc accccggccg ggacaccttc    960
ggcgtcagcg tcatgatcgc cgcccggggc ggaaaggtgg tcacctgcgc atcgaccacc   1020
ggctaccagc acacctacga caaccgccat ctgtggatgc gcgtcaaacg catcatcggg   1080
tcacatatgg cgaactaccg ggaagcctgg gccgcgaacg aactcgtcgc acgcggcagc   1140
atccaccccg tgctctcccg ggtctacccc ctcgacgcca caggcgacgc cacgcacgcc   1200
gtcgccaaca cagccacca cggcaaggtg ggcgtgctct gcctcgccga ccgccccggc   1260
atgggagtgc gcgaccccga gctgcgggcc cggaaactcg acagcatcaa cctgttccgg   1320
aaggggcagc cccgg                                                    1335

<210> SEQ ID NO 5
<211> LENGTH: 1158
<212> TYPE: DNA
<213> ORGANISM: Streptomyces tsukubaensis

<400> SEQUENCE: 5
gtgagcgaat ccgaacgcct cggtatcgtc agggatttcg tcgcccggga gatcctgggc     60
cgcgaaggca tcctcgactc gctggcggac gcaccactgg ccctgtacga acgcttcgcc    120
gagacgggcc tgatgaactg gtgggtcccc aaggagcacg gcggtcttgg gctcggcctg    180
gaagagagtg tgcggatcgt ctccgaactc gcctacgggg acgccggggt ggcgttcacc    240
ctgtttctgc ccgtcctgac gaccagcatg atcggctggt acggcagcga ggagctcaag    300
gagagattcc tcggccctct cgtggcccgg cggggcttct cgccacgct gggcagcgag    360 cacgaggccg gcagcgaact ggcccggatc tccaccacgg tccgccgtga cggcgacacg    420
ctggtactcg acggcaccaa ggccttctcc accagcaccg acttcgcccg gttcctcgtc    480
gtcatcgccc gttcggcgga cgacccggcc cggtacacgg cggtcaccgt accgcgggac    540 gcgccgggge tgcgggtcga caaacgctgg gacgtcatcg ggatgcgcgc ctccgcgacc    600
tatcaggtgt cgttctccga ctgccgggtg ccggggggaca acgcgctgaa cggcaatggg    660
ctgcggctgc tggagatcgg cctcaacgcc agcagaatcc tgatcgccgc atccgctctg    720
ggtgtcgccc gcaggatccg cgatgtgtgc atggagtacg ggaagacgaa gtcgctcaag    780
ggcgctccgc tcgtcaagga cggcgtgttc gccgggcggc tcggccagtt cgagatgcag    840
atcgacgtga tggcgaacca gtgcctggcg gccgcacggg cctacgacgc gaccgcggcc    900
cggcccgacg ccgccagggt gctgctgcgg cagggcgccc agaagtcggc actgaccgcg    960
aagatgttct gcgggcagac ggcctggcag atcgcgtcca ccgcgtcgga gatgttcggc   1020
```

```
ggcatcgggt acacgcacga catggtgatc gggaagctgc tgcgggatgt gcggcacgct   1080
tcgatcatcg agggcggcga cgacgtcctg cgcgatctcg tctaccagcg cttcgtcgtc   1140
cccaccgcga aacgtacc                                                 1158

<210> SEQ ID NO 6
<211> LENGTH: 1152
<212> TYPE: DNA
<213> ORGANISM: Streptomyces tsukubaensis

<400> SEQUENCE: 6
atgccttcgc atcactggga aacccgggcg gtccatgccg ccgtgaggat tcttgtcgat     60
ctcggactgc atgtcccgcc catagacctg tccaccacct accccctccccg cgacaccgtt  120 gccgaggcgg cgcggatcga cgtgttcggc tccggagccg acgacggcgg tccgccgatc   180
tacggccggg cagggaaccc caccgtcgca cggttcgagt ccgcgctggc cgaactggaa   240
ggggccgaag ccgcggtggc cttcgccagc ggtatggcag cgctctgcgc ctgccttctc    300
gtgcaggtcg cccggggacg gccgcatatc gtcgccgtcc gtccctgta cggcaccagc    360 gactacctcc tggactcggg cctgctgggc acctcggtga cctgggcgca accccacagc   420
gccggcgatg ccatccgcag cgacacgggg ctggtgatcg tcgagtcacc cgccaacccc   480
acactgacgg agaccgacat ccaggcgctg ccgctgcat cgctccggt tccggtactg    540 gtcgacaaca ccttcgcaac gcccgcgctc cagcgccccc tgaacagggg tgccgccatc   600
gttctgcaca gcgcgacgaa gtacctgggg gccacggtg acgtcatggg cggtgtggtg   660
gcgtcgaacg aggagttcgc ccgtgccctg cggcggatcc ggttcgccac cggagggatc   720
ctgcaccccc tggctggcta ccagctcctc agaggactgt cgacgctctc ggtgcggatg   780
caccacgctt cggcctcggc tgccgagatc gcccgccggc tcctgcacca tccggcggtc   840
accagggtcc actacccggg gctgagcggt gaaccccggc cgccgaagca gatggccgca   900
ggcggggcaa tcgtgtcctt cgaggtcgac gatccgcacg cggtgaccgg cggcgtacgt   960
ctcttcaccc cggcggtcag cctcggcagc gtcgacagcc tcattcagca cccggtctcg  1020
ctcacccacc acgccatgga cccgggctca cgcgaacagg ccggtatctc cgaccgactg  1080
ctccggatct ccgtcggcct cgaacacgtc gacgatctgt gggccgacct cacccaggcc  1140
ctgacgcggg ac                                                      1152

<210> SEQ ID NO 7
<211> LENGTH: 465
<212> TYPE: DNA
<213> ORGANISM: Streptomyces tsukubaensis

<400> SEQUENCE: 7
atgaaagaaa aggttgtcct ggattcgata gatcaggcaa ttctgcgtga gctgcagaat     60
gatggtcggc tgcccaacaa gacgctggcc cggagggtcg gcgtggcacc gtccacctgt   120
ctggcccgca cgcagaggct gatggaggca ggtgtgatca gaggtttcca ggctcaggtg   180
agtgccgcgg cgatcggccg gcaggtccag gccgtcctcg ccgtccagtt catcgcccat   240
tcacgtccct ttgtcgaccc gttcgtgcca tgggccaggag agcggcccga gactcgtgcg    300
cttcaccatg tgaccggagc cttcgacttc ctcgtccaca cggcctgccg tgacaccgag   360
aacctccagc aactcgtcct ggagttcacc gcacgccgag aggtgggccg agtggagacc   420
cacctcgtat tcggatcctg gtcgggagga cccctgactc cgggc                   465
```

<210> SEQ ID NO 8
<211> LENGTH: 1227
<212> TYPE: DNA
<213> ORGANISM: Streptomyces tsukubaensis

<400> SEQUENCE: 8

| | | |
|---|---|---|
| atggaccgag aacccgtttt cgtcctcgac ccgcgcggcg gcgatcgcca tggcgaggac | 60 |
| gccgccctcc gcgcccgcgg cccctgacc cgagtcgacg ccctcggcgt ggaggcgtgg | 120 |
| tcggtcaccg accggtgct gctccgtcgg ctgctgctgg actcgcgggt ctccaaaaac | 180 |
| gcccggcaac actggcccgc cttcccggag gagatcgtcg gagtctggcc gctcgccctc | 240 |
| tgggtcgccg tggagaacat gttcaccgcc tatggcgagg agcaccgacg gctgcggcgg | 300 |
| accatcgggc cggccttcgc cgcccgcagg atcaacgcgc tggcgccggt catcgagcag | 360 |
| ctcgtggggg agctgctgga cgagctcgcc gccacccgc ccggagagcc ggtcgacctg | 420 |
| cgggagcact tcgcctatcc gctgcccatc ggggtcgtcg ccagctcgc cggcctcccc | 480 |
| gaatccgtcc ggccccggtt ccgccgtacc gtcgacgtga tcttctccac cagccacagc | 540 |
| cccgaggaga cgaccgccgc ggtccaggat ctgtacgcgc tcctcgccga cctcgtggcc | 600 |
| gccaagcgcg ccgagccggg agacgacctc acgtcggcgc tcatcgccgc cagggatacg | 660 |
| gaaggcgacg gagagcccct gacggaggcc gaactcgtcg acaccctgct gctggtggtc | 720 |
| aacgccggtt cgaaaccac cgtcaacctc ctggaccagg cgatcaccgc actcctcacc | 780 |
| gaccccgggc aactcgccca tgtccgcgcc ggacgcgcgg gctggaagga cgtggtcgag | 840 |
| gaatcactcc gccacgaggc cccgctcgcg catctgccga tgcgcttcgc cgtggaggac | 900 |
| atccccctcc ccgaacacgg cgtgaccatc cggcagggcg acgccgtcct gcccgcctac | 960 |
| gccgccgcca accggcatcc ggacctgcac ggcctcaccg ccgacgactt cgacgccacc | 1020 |
| cggagcgaca agagccatct ctccttcgga cacggcatgc acctctgcct cggagccgcc | 1080 |
| ctcggtcgcc tcaagccga aatcgccctg gcggcctct tcgaacgctt ccccgtctc | 1140 |
| gccctcgccg tgcccctgga ccgactgcgc cccaagccga gcttcatctc caacggccac | 1200 |
| agcgaactgc ccgtcatcat cgacccg | 1227 |

<210> SEQ ID NO 9
<211> LENGTH: 1188
<212> TYPE: DNA
<213> ORGANISM: Streptomyces tsukubaensis

<400> SEQUENCE: 9

| | | |
|---|---|---|
| gtgggcactc ctcaacccga tgtcgccgag ggcctcacgc cggtcgaggc ggcgcgctca | 60 |
| ctggtcccgc tgctcgctgc cgaagcggcc cgcaccgagg agcggcgcgc cctcaccggc | 120 |
| gccactgtga ccggcctgcg ccgggccggt ctgctccgcc tcgggacccc gaccgagtgc | 180 |
| ggcggcgggg gtgcgggtgc ccgtaccgcg gtggatgtgt gcgaggagct ggccaagggc | 240 |
| tgtgcgtccg cctcctggat cgtgggcatc gcctacggcg gcgccctctt cgcctcccag | 300 |
| cttcccccact ccgagcgtgc gggccctgtgg cgggacgacc cggacgctgt cgtctgcggc | 360 |
| agcgccaacc cgtccggaac ggcgcggcgt acggacggcg gctggaccct gagcggccgt | 420 |
| tggccctgga tctccggcat ccaccatgcg ccctggaccc tgctcggctt cgtccggccc | 480 |
| ggcgcagggg gcgaaccgga gcggcatg gccgtggtcc ccaccgccgg cctgaccgtc | 540 |
| gaggacgtct ggcatatggc gggcatgcgc ggcaccggca gcgacacggc cgtcgcggac | 600 |
| ggcgtgtacg tgccggactc ccgcacgatc tccctgaccg ccatggcgga cggcgcctac | 660 |

```
cggcgacgcc atcccggcga accccgggtc accttccatc tctccatcaa cctgccgttg    720
gtggcgacgg ccgtcgggat cgccacagcg tccctggaga aggtgctgga tgccgcggcc    780
cggggcaaac agacggtctc cccgctgcac cggctggtcg ccgaggactc cgcccatcag    840
ctcaatgtgg cggacgccgc gacgctcatc gacacggccc ggctgcatct gcgccgcgcc    900
gccgacgagg tggactccca cgcccgcgcg gggcgccgtc ccgcgctcgc cgagcgggcc    960
cgactgcgga tggacgccgc ccacgccatg cgctgcgccc gcgacgccgt gagcctgctg   1020
ctggacaccg cgggcgcggg cagcttcgcg gacggctcgg tcctgcaacg ggcctggcgc   1080
gatatcgaga cggcgtcccg gcacgccgcg ctcagcgtcc agaccagcaa ggagatatac   1140
ggccgcgctc tgctcggcgc cccgctgccg cccggcccgg tcgtctga                1188

<210> SEQ ID NO 10
<211> LENGTH: 654
<212> TYPE: DNA
<213> ORGANISM: Streptomyces tsukubaensis

<400> SEQUENCE: 10
gtggccctgc tggaccgcga cggcgacgcc gtgaccgggc tgtccgccgc cctcgacccc     60
gccggcgcgg gcaccgcgct gccgctgcgt gcggacgtcg acgacacgga cgccgtccac    120
gccgcgctgc gcgagaccgc cgccgcctgg cacgcgcccg acatcctgat caacaatgcc    180
gcccggaccg ccccggctc ggtatgggac atcgaaccgg acgaatggga cgccgtactg    240
acgaccaatc tgcgcagcgt cctgaccctg accggctgt gcgcgcccgc gatgcgcgac    300
cgcggctggg gccgggtggt caacctctcc tcgctggccg gtcagcaggg cggcacccct    360
gccggcgccc actactccgc cgccaaggcg ggcgttctcg tgctgaccaa ggtgttcgcc    420
cgtgaactgg cggcgcacgg cgtgaccgtc aacgcggtag ccccggccgc cgtcgacacc    480
ccggcggtcg ccgggctcgg cccgtcggcg gtggccgagg cggccggca gatcccggtg    540 ggccggatgg ggaggccttc ggaggtcgcc ggcctcgtgg cctatctggt gggcgaagag    600
ggcggatacg tcaccggcgc caccttcgac atcaacggcg gcacccatat gcgc          654

<210> SEQ ID NO 11
<211> LENGTH: 1335
<212> TYPE: DNA
<213> ORGANISM: Streptomyces tsukubaensis

<400> SEQUENCE: 11
gtgaaggaaa tcctggacgc gatctcgtcg gcggatgcga cgccggcgga cttcgccgcc     60
ctcgcagtcc ccgagtccta ccgcgcggtg accgtgcaca aggacgaagc cgagatgttc    120
gccggcctgc cgagccggga caaggacccc cgtaagtcgc tgcatgtcga agacgtcgcg    180
gtgcccgaac tcgggcccgg tgaggcgctc gtcgccgtga tggccagctc cgtcaactac    240
aactccgtgt ggacgtcgat cttcgagccg ctgtccacct tcggcttcct ggagcgctac    300
gggcgcgtca gcgaactcac ccggcggcac gatctgccgt accacgtcat cggctcggac    360
ctggcgggcg tcgtcctgcg caccgggccc ggggtgaacg cctggaaacc gggggacgag    420
gtcgtcgccc actgtctgtc ggtggagctg agtcctcgg acgggcacaa cgacaccatg    480
ctcgaccccg agcagcggat ctggggcttc gagaccaact tcggcggcct cgccgaactc    540
gcgctggtca gtcgaaacca gctgatgccc aagccagccc atctgtcctg ggaggaggcc    600
gcggcgccgg ggctggtgaa ctccaccgcg taccgccagc tggtctcccg caacggcgcc    660
```

```
cggatgaagc agggcgacaa cgtcctgatc tggggtgcga gcggcgggct cggctcgtac    720
gccacccagt tcgcgctcgc cggggcgcc aacccgatct gtgtggtctc cagcgaccgc    780
aaggcggaca tctgccggtc gatgggcgcg gaggcgatca tcgaccggag cgccgaggac    840
taccggttct ggaaggacga gcggtcgcag gacccgcgtg agtggaagcg gttcggcgcc    900
cggatccgtg agctgaccgg cggcgaggac gtcgacatcg tcttcgagca ccccggccgg    960
gagaccttcg gggcctccgt gtacgtcacc cgcaagggcg gcacgatcgt cacctgcgcc   1020
tcgacctcgg gctatcagca cgagtacgac aaccgctacc tctggatgtc gctgaagcgg   1080
atcatcggct cccacttcgc caactaccgg gaggcgtggg aggccaaccg gctgatcgcc   1140
aaggggaaga tccaccccac gctgtcgaag gtgtaccccc tggcggagac cggccaggcg   1200
gcgcacgacg tccaccgcaa cgcccaccag ggcaaggtcg gcgtcctctg tctggcaccc   1260
cgtgagggca tgggtgtgcg ggacgaggag acgcgcgccc ggcacctcgg cgccatcaac   1320
cggttccgca atgtc                                                    1335

<210> SEQ ID NO 12
<211> LENGTH: 1977
<212> TYPE: DNA
<213> ORGANISM: Streptomyces tsukubaensis

<400> SEQUENCE: 12
atgcgcacct atgccgggca ctccacggcc gaggcctcga cgagctgta ccggcgcaat     60 ctcgccaagg ggcagacggg cctgtcggtc gccttcgacc tgccgacgca gacggggtac    120
gaccccgatc atctgctggc ccgcggcgag gtcggccggg tcggggtgcc cgtcgcccat    180
ctcggcgata tgcggaggct gttccggag atcccgctgg gcagatgaa cacgtcgatg    240 acgatcaacg ccaccgcgat gtggctgctg gcgctctacc aggtcgtcgc cgaggaacag    300
ggcacggatc tcgccgccct ccagggcacc acccagaacg acatcgtgaa ggagtacctg    360
tcgcgcggga cgcacgtctt cccgcccggc ccttcgctgc ggctgacgac cgacatgatc    420
gcgtacacgg tcggccggat gcccaagtgg aatccgatca acatctgcag ctaccacctc    480
caggaggccg gtgccacccc ggtccaggag atcagctacg cgatgtcgac ggcggtcgcc    540
gtactggacg cggtcttcgc ctccggacag gtgcccgacg accgcagggg cgaggtggtg    600
ggccggatct ccttcttcgt gaacgcgggc gtccggttca tcgaggagat gtgcaagatg    660
cgggccttcg gccggatctg ggaccggatc acccgggagc ggtacggaat cgaggacccc    720
cggcagcgcc ggttccgcta cggcgtccag gtcaactcgc tggggctgac cgaggcacag    780
ccggagaaca acgtccagcg gatcgtgctg gagatgctgg cggtgacgct ctccaaggac    840
gcccgggccc gggccgtaca gcttccggcg tggaacgagg cgctcgggct gccccggccg    900
tgggaccagc agtggtcgct ccgtatccag caggtcctgg cgcacgagtc ggatctgctg    960
gagtacgacg atatcttcgc gggctcccgg gtgatcgagg ccgaggtcgc cgcgctggag   1020
gcggagtgcc tggccgagat cgcccggatc gaggagatgg cgggggcgat ggctgccgtg   1080
gagtcgggct atctgaaggc gcagctggtc tcctcgcacg ccgagcggcg ggcccggatc   1140
gaggccggca aggagaagat cgtcgggtc aacgtcttcc aaagcaccga ggagaatccg   1200
ctgaccgccg atctggacgg cgcgatcatg acggtcgatc cggcgaacga ggcccgggtg   1260
gtcgccgccc tgcactcctg gcgcgaggat cggaacgaac ccgcgccac cgaggcgctg   1320 accgcgctga agaggcggc ggcgggtacg gacaatctga tgaccaccac gctggagtgc   1380
gcccgcgcgg gcgtcaccac cggcgagtgg agctgggcgc tgcgggacgt cttcggcgag   1440
```

```
ttccgggcgc cgacgggggt gtcgggcgcg ccgctcgcgg tgaccgccga accggggagc   1500
ccgctggcgg cggtccggga aaggtgacc cgtaccgcgc gggagctggg ggccgggaag    1560
ctgcggctgc tggtgggcaa gccggggctc gacgggcatt ccaacggtgc cgagcagatc   1620
gccgtacggg ccaggacgc cggggttcgag gtggtctacc agggcatccg gctgaccccg   1680
gggcagatcg tgtcggcggc gctcgcggag gacgtgcact gtgtgggcct gtcgatcctc   1740
tccggatcgc atgccgagct ggtgcccgag gtactggcgc agctccgcgc ggccggtgcg   1800
gccgagctgc cggtggtggt cggcgggatc attccggccg cggacgcagc cgcgctccgg   1860
gcggccgggg tggccgccgt cttcaccccg aaggacttcg gtatcacgga gatcatcggc   1920
cgtatcgtcg acgagatccg gcaagcgaac cagctcgacc ccctggaggt ccccgta     1977
```

<210> SEQ ID NO 13
<211> LENGTH: 431
<212> TYPE: PRT
<213> ORGANISM: Streptomyces tsukubaensis

<400> SEQUENCE: 13

```
Met Thr Ser Gly Val Ala Phe Leu Phe Pro Gly Gln Gly Ser Tyr Val
1               5                   10                  15

Pro Gly Val Phe Ala Gly Leu Gly Ala Asp Ala Gly Arg Val Ala Thr
            20                  25                  30

Leu Val Ala Glu Ile Asp Ala Ala Val Glu Glu Phe Arg Leu Lys Pro
        35                  40                  45

Val Arg Pro Leu Leu Phe Ser Pro Asp Ala Pro Ala Leu Ala Glu Leu
    50                  55                  60

Leu Glu Ser Asp His Glu Arg Leu Asp Val Ala Ile Leu Ala Thr Ser
65                  70                  75                  80

Ile Ala Leu Ala Glu Leu Leu Glu Ser Arg His Gly Met Ser Pro Asp
                85                  90                  95

His Val Ala Gly His Ser Leu Gly Glu Phe Gly Ala Leu Ala Val Ala
            100                 105                 110

Gly Val Phe Thr Pro Gly Asp Ala Ala Arg Ala Val Cys Glu Arg His
        115                 120                 125

Ala Thr Leu Arg Lys Ala Pro Pro Thr Gly Gly Met Leu Ala Val
    130                 135                 140

Lys Ala Asp Ala Ala Arg Ala Gly Glu Leu Ile Ala Ala Arg Ala
145                 150                 155                 160

Gly Thr Ser Ala Val Ser Ala Leu Asn Ser Pro Ser Gln Thr Val Ile
                165                 170                 175

Ser Gly Ala Glu Ala Asp Leu Val Lys Val Gln Gln Leu Ala Arg Glu
            180                 185                 190

Glu Gly Ile Arg Thr Ser Arg Leu His Val Pro Gly Pro Phe His Val
        195                 200                 205

Pro Gln Leu Ala Asp Ala Ser Ala Leu Tyr Ala Thr Thr Met Arg Thr
    210                 215                 220

Ile Arg Ile Ser Ala Pro Arg Glu Arg Phe Phe Tyr Ser His Gly Leu
225                 230                 235                 240

Gly Arg Phe Leu Thr Ala Gln Asp Val Val Asp Leu Met Val Asn
                245                 250                 255

Asp Met Thr Arg Pro Val Arg Phe His Asp Ser Val Arg Ala Leu Asn
            260                 265                 270

Ala Glu Gly Val Thr Thr Tyr Val Glu Cys Gly Ala Leu Asp Val Leu
```

```
                     275                 280                 285
Thr Arg Ile Val Ser Gly Ser Leu Pro Arg Ala Val Thr Leu Ala Pro
290                 295                 300

Leu Arg Glu Ala Thr Thr Pro Asp Leu Ser Ala Arg Leu Arg Pro
305                 310                 315                 320

Ala Gly Thr Pro Ala Val Asn Gly Val Ala Pro Ala Gly Pro Ala
                325                 330                 335

Pro Ala Ala Glu Val Asp Pro Glu Val Leu Ala Gly Val Arg Ala Val
                340                 345                 350

Cys Ala Glu Val Leu Glu Tyr Pro Leu Glu Val Ile Thr Asp Asp Ala
                355                 360                 365

Asp Phe Gln Ala Asp Leu Gly Val Asp Ser Leu Ala Met Thr Glu Leu
    370                 375                 380

Gln Ala His Ala Leu Gln Arg Phe Gly Leu Lys Glu Thr Leu Gln Asp
385                 390                 395                 400

Ala Asp Thr Gly Thr Tyr Gly Thr Val Ser Gly Leu Ala Ala Tyr Ile
                405                 410                 415

Thr Gly Leu Leu Ser Glu Gly Thr Gly Ser Val Ser Gly Arg Arg
                420                 425                 430

<210> SEQ ID NO 14
<211> LENGTH: 796
<212> TYPE: PRT
<213> ORGANISM: Streptomyces tsukubaensis

<400> SEQUENCE: 14

Val Ile Ser Arg Ala Pro Asp Gly Glu Gly Pro His Asp Asp Arg Val
1               5                   10                  15

Ala Val Val Gly Met Gly Val Ala Val Pro Gly Ala Cys Asp Pro Glu
                20                  25                  30

Glu Leu Trp Lys Leu Leu Cys Gly Asp Arg Pro Val Phe Asp Glu Pro
            35                  40                  45

Ser Asp Arg Phe Arg Leu Asp Ser Phe Trp Ser Ala Asp Pro Ala Ala
        50                  55                  60

Glu Asp Arg Gly Tyr Val Arg Thr Ser Gly Phe Leu His Asp Phe Arg
65                  70                  75                  80

Pro His Pro Ala Leu Ala Ala Glu Ile Ala Ala Gly Thr Leu Ser Ala
                85                  90                  95

Ala Ala Gln Asn Pro Val Trp Leu Arg His Cys Leu Leu Gln Ala Arg
                100                 105                 110

Asp Thr Val Thr Ala Arg Ser Thr Arg Asp Tyr Ala Tyr His Val Gly
            115                 120                 125

Thr Ser Ala Leu Val Gly Gln Arg Thr Asp Glu Ala Val Leu Ala Glu
        130                 135                 140

Cys Val Pro Arg Ala Val Ala Glu Arg Leu His Arg Asp Glu Pro Ala
145                 150                 155                 160

Arg Met Ala Glu Ala Glu Ala Arg Leu Arg Ala Leu Leu Arg Ser His
                165                 170                 175

His Gly Tyr Gly Ala Glu Glu Pro Arg Asp Thr Leu Pro Asp Arg Val
                180                 185                 190

Val Arg Ala Ala Ala Ala Gly Leu Leu Pro Asp Asp Cys Glu Phe Ser
            195                 200                 205

Val Val Asp Ala Ala Cys Ser Ser Ser Leu Tyr Ala Ile Gly Leu Gly
        210                 215                 220
```

```
Val Ala Ser Leu Leu Ala Gly Ala Cys Asp Ile Ala Tyr Cys Gly Gly
225                 230                 235                 240

Val Ser Gly Val Thr Pro Arg Tyr Asn Val Thr Phe Ser Lys Leu His
            245                 250                 255

Gly Leu Ser Pro Ser Gly Asp Val Arg Ala Phe Asp Asp Ala Asp
        260                 265                 270

Gly Thr Leu Phe Ser Asp Gly Ala Gly Val Val Ala Leu Lys Arg Leu
        275                 280                 285

Asp Arg Ala Val Glu Asp Gly Asp Pro Val Phe Gly Val Leu Val Gly
        290                 295                 300

Phe Gly Gly Ser Ser Asp Gly Arg Gly Thr Ala Ile Tyr Ala Pro Asn
305                 310                 315                 320

Pro Val Gly Gln Arg Arg Cys Leu Asp Arg Ala Arg Gln Ala Ser Gly
            325                 330                 335

Leu Thr Ala Asp Asp Val Asp Trp Val Ile Ala His Gly Thr Gly Thr
                340                 345                 350

Ala Val Gly Asp Ala Val Glu Leu Arg Thr Leu Ala Ala Ala Thr Asp
            355                 360                 365

Pro Gly Ser Val Trp Cys Gly Ser Asn Lys Ser Leu Leu Gly His Thr
370                 375                 380

Gly Trp Ser Ser Gly Val Val Ser Val Val Gln Ala Leu Thr Ala Leu
385                 390                 395                 400

Arg Gln Gly Thr Ile Pro Ala Gln Arg Arg Phe Thr Gly Pro Gly Leu
                405                 410                 415

Thr Ala Gln Thr Gly Asp Arg Val Arg Ile Pro Ser Ala Asp Val Pro
            420                 425                 430

Trp His Ala Gly Gly Arg Arg Ser Arg Thr Ala Gly Val Ser Ala Phe
        435                 440                 445

Gly Phe Gly Gly Thr Asn Ala His Leu Leu Ile Thr Asp Arg Glu Pro
    450                 455                 460

Val Arg Thr Gly Pro Arg Pro Ala Arg Thr Gly Pro Asp Pro Val Val
465                 470                 475                 480

Val Leu Ala Trp Thr Ala His Leu Pro Gly Asp Pro Gly Pro Glu Ala
                485                 490                 495

Thr Glu Arg Leu Leu Arg Glu Gly Arg Ile Pro Gly Pro Arg Thr Phe
            500                 505                 510

Gly Pro Arg Tyr Pro Ala Pro Pro Phe Pro Asp Val Arg Leu Pro Pro
        515                 520                 525

Pro Thr Val Arg Ser Thr Asp Ala Gly Gln Leu Met Ala Leu Arg Val
    530                 535                 540

Ala Gly Leu Phe Ala Ala Glu His Gly Glu Leu Trp Ala Pro Val Arg
545                 550                 555                 560

Ala Thr Thr Gly Val Phe Ala Ala Thr Gly Pro Pro Ser Ser
                565                 570                 575

Met Asp His Leu Val Arg Cys His Ala Ala Asp Val His Arg Ile Leu
            580                 585                 590

Asp Glu Pro Asp Arg Thr Ala Phe Thr Glu Trp Leu Ala Asp Leu Arg
        595                 600                 605

Ala Thr Thr Pro Ala Thr Thr Lys Asp Thr Leu Pro Gly Leu Leu Pro
            610                 615                 620

Asn Ile Ile Pro Ala Arg Ile Ala Asn Arg Tyr Asp Leu Gly Gly Pro
625                 630                 635                 640

Thr Met Leu Val Asp Thr Gly Thr Thr Ser Gly Leu Thr Ala Val His
```

```
            645                 650                 655
Thr Ala Arg Gln Leu Ala Ala Gly Ala Val Asp Met Ala Leu Val
            660                 665                 670

Leu Gly Val Ser Ala Thr Gly Arg Pro Glu Phe Ala Arg Phe Met Gly
            675                 680                 685

Val Ala Ala Glu Arg Ile Ala Glu Gly Ala Phe Leu Leu Ala Leu Ser
            690                 695                 700

Arg Glu Ser Val Ala Leu Ala His Gly Leu Thr Pro Leu Val Arg Leu
705                 710                 715                 720

Arg Thr Asp Trp Thr Gly Ser Pro Gln Ala Ser Ala Asp Ala Val Pro
                725                 730                 735

Gly Gly Pro Gly Ala Ala Glu Asp Thr Phe Leu Gly Ala Asp Gly Val
            740                 745                 750

Leu Ala Val Ile Arg Ala Leu His Ser Thr Ala Ser Gly Val Thr Val
            755                 760                 765

Gly Pro Ala Asp Gly Glu Pro Gly Pro Val Ile Thr Leu Ser Pro Ala
            770                 775                 780

Asp Gly Ser Pro Leu Arg Gln Thr Arg Thr Ser Arg
785                 790                 795

<210> SEQ ID NO 15
<211> LENGTH: 445
<212> TYPE: PRT
<213> ORGANISM: Streptomyces tsukubaensis

<400> SEQUENCE: 15

Met Thr His Val Arg Asp Ala Ala Thr Asp Pro Gln Ala Ile
1               5                   10                  15

Ala Ala Cys Glu Val Pro Ala Gly Tyr Arg Ala Ala Val Val Leu Ala
                20                  25                  30

Ala Asp His Gln Ala Leu Ala Gly Ser Pro Val Glu Asp Arg Asp Pro
            35                  40                  45

Arg Lys Thr Val Gln Val Gln Glu Val Pro Thr Pro Glu Pro Asp His
50                  55                  60

Gly Glu Val Leu Ile Ala Thr Met Ala Ser Ser Ile Asn Tyr Asn Thr
65                  70                  75                  80

Val Trp Ser Ala Leu Phe Glu Pro Val Pro Thr Phe Arg Phe Leu Arg
                85                  90                  95

Thr Leu Gly Arg Thr Ser Pro Glu Ala Ala Arg His Asp Gln Pro Tyr
                100                 105                 110

His Val Leu Gly Ser Asp Leu Ser Gly Val Val Leu Arg Thr Gly Pro
            115                 120                 125

Gly Val Arg Glu Trp Lys Pro Gly Asp Glu Val Ala His Cys Leu
130                 135                 140

Gln Pro Asp Leu Gln Thr Pro Gly Gly His Asp Asp Thr Leu Leu Asp
145                 150                 155                 160

Pro Gly Gln Arg Val Trp Gly Tyr Glu Thr Asn Phe Gly Gly Leu Ala
                165                 170                 175

Glu Leu Ser Leu Val Lys Ala Asn Gln Leu Met Pro Lys Pro Ala His
                180                 185                 190

Leu Thr Trp Glu Glu Ala Ala Ser Leu Gly Val Ala Leu Ser Thr Ala
            195                 200                 205

Tyr Arg Gln Leu Val Ser His His Gly Ala Ala Met Lys Gln Gly Glu
            210                 215                 220
```

```
Arg Val Leu Val Trp Gly Ala Gly Gly Val Gly Ala Tyr Ala Thr
225                 230                 235                 240

Gln Leu Ala Leu Asn Gly Gly Ala Val Pro Ile Cys Val Val Ser Ser
                245                 250                 255

Gln Ala Lys Ala Asp Leu Cys Arg Gln Met Gly Ala Glu Leu Val Ile
            260                 265                 270

Asp Arg Ala Ala Glu Gly Phe Ser Phe Trp Glu Gly Arg Asp Arg Pro
        275                 280                 285

Arg Leu Ser Glu Trp Ser Arg Phe Arg Gly Ala Val Arg Ser Leu Ala
    290                 295                 300

Gly Asp Asp Pro Asp Ile Val Ile Glu His Pro Gly Arg Asp Thr Phe
305                 310                 315                 320

Gly Val Ser Val Met Ile Ala Ala Arg Gly Gly Lys Val Val Thr Cys
                325                 330                 335

Ala Ser Thr Thr Gly Tyr Gln His Thr Tyr Asp Asn Arg His Leu Trp
                340                 345                 350

Met Arg Val Lys Arg Ile Ile Gly Ser His Met Ala Asn Tyr Arg Glu
            355                 360                 365

Ala Trp Ala Ala Asn Glu Leu Val Ala Arg Gly Ser Ile His Pro Val
        370                 375                 380

Leu Ser Arg Val Tyr Pro Leu Asp Ala Thr Gly Asp Ala Thr His Ala
385                 390                 395                 400

Val Ala Asn Asn Ser His His Gly Lys Val Gly Val Leu Cys Leu Ala
                405                 410                 415

Asp Arg Pro Gly Met Gly Val Asp Pro Glu Leu Arg Ala Arg Lys
            420                 425                 430

Leu Asp Ser Ile Asn Leu Phe Arg Lys Gly Gln Pro Arg
            435                 440                 445

<210> SEQ ID NO 16
<211> LENGTH: 386
<212> TYPE: PRT
<213> ORGANISM: Streptomyces tsukubaensis

<400> SEQUENCE: 16

Val Ser Glu Ser Glu Arg Leu Gly Ile Val Arg Asp Phe Val Ala Arg
1               5                   10                  15

Glu Ile Leu Gly Arg Glu Gly Ile Leu Asp Ser Leu Ala Asp Ala Pro
            20                  25                  30

Leu Ala Leu Tyr Glu Arg Phe Ala Glu Thr Gly Leu Met Asn Trp Trp
        35                  40                  45

Val Pro Lys Glu His Gly Gly Leu Gly Leu Gly Leu Glu Glu Ser Val
    50                  55                  60

Arg Ile Val Ser Glu Leu Ala Tyr Gly Asp Ala Gly Val Ala Phe Thr
65                  70                  75                  80

Leu Phe Leu Pro Val Leu Thr Thr Ser Met Ile Gly Trp Tyr Gly Ser
                85                  90                  95

Glu Glu Leu Lys Glu Arg Phe Leu Gly Pro Leu Val Ala Arg Arg Gly
            100                 105                 110

Phe Cys Ala Thr Leu Gly Ser Glu His Glu Ala Gly Ser Glu Leu Ala
        115                 120                 125

Arg Ile Ser Thr Thr Val Arg Arg Asp Gly Asp Thr Leu Val Leu Asp
    130                 135                 140

Gly Thr Lys Ala Phe Ser Thr Ser Thr Asp Phe Ala Arg Phe Leu Val
145                 150                 155                 160
```

Val Ile Ala Arg Ser Ala Asp Pro Ala Arg Tyr Thr Ala Val Thr
            165                 170                 175

Val Pro Arg Asp Ala Pro Gly Leu Arg Val Asp Lys Arg Trp Asp Val
        180                 185                 190

Ile Gly Met Arg Ala Ser Ala Thr Tyr Gln Val Ser Phe Ser Asp Cys
            195                 200                 205

Arg Val Pro Gly Asp Asn Ala Leu Asn Gly Asn Gly Leu Arg Leu Leu
        210                 215                 220

Glu Ile Gly Leu Asn Ala Ser Arg Ile Leu Ile Ala Ala Ser Ala Leu
225                 230                 235                 240

Gly Val Ala Arg Arg Ile Arg Asp Val Cys Met Glu Tyr Gly Lys Thr
                245                 250                 255

Lys Ser Leu Lys Gly Ala Pro Leu Val Lys Asp Gly Val Phe Ala Gly
            260                 265                 270

Arg Leu Gly Gln Phe Glu Met Gln Ile Asp Val Met Ala Asn Gln Cys
        275                 280                 285

Leu Ala Ala Arg Ala Tyr Asp Ala Thr Ala Ala Arg Pro Asp Ala
    290                 295                 300

Ala Arg Val Leu Leu Arg Gln Gly Ala Gln Lys Ser Ala Leu Thr Ala
305                 310                 315                 320

Lys Met Phe Cys Gly Gln Thr Ala Trp Gln Ile Ala Ser Thr Ala Ser
                325                 330                 335

Glu Met Phe Gly Gly Ile Gly Tyr Thr His Asp Met Val Ile Gly Lys
            340                 345                 350

Leu Leu Arg Asp Val Arg His Ala Ser Ile Ile Glu Gly Gly Asp Asp
        355                 360                 365

Val Leu Arg Asp Leu Val Tyr Gln Arg Phe Val Val Pro Thr Ala Lys
    370                 375                 380

Arg Thr
385

<210> SEQ ID NO 17
<211> LENGTH: 384
<212> TYPE: PRT
<213> ORGANISM: Streptomyces tsukubaensis

<400> SEQUENCE: 17

Met Pro Ser His His Trp Glu Thr Arg Ala Val His Ala Gly Arg Glu
1               5                   10                  15

Asp Leu Val Asp Leu Gly Leu His Val Pro Pro Ile Asp Leu Ser Thr
            20                  25                  30

Thr Tyr Pro Ser Arg Asp Thr Val Ala Glu Ala Ala Arg Ile Asp Val
        35                  40                  45

Phe Gly Ser Gly Ala Asp Asp Gly Gly Pro Pro Ile Tyr Gly Arg Ala
    50                  55                  60

Gly Asn Pro Thr Val Ala Arg Phe Glu Ser Ala Leu Ala Glu Leu Glu
65                  70                  75                  80

Gly Ala Glu Ala Ala Val Ala Phe Ala Ser Gly Met Ala Ala Leu Cys
                85                  90                  95

Ala Cys Leu Leu Val Gln Val Ala Arg Gly Arg Pro His Ile Val Ala
            100                 105                 110

Val Arg Pro Leu Tyr Gly Thr Ser Asp Tyr Leu Leu Asp Ser Gly Leu
        115                 120                 125

Leu Gly Thr Ser Val Thr Trp Ala Gln Pro His Ser Ala Gly Asp Ala

```
                130             135             140
Ile Arg Ser Asp Thr Gly Leu Val Ile Val Glu Ser Pro Ala Asn Pro
145                 150                 155                 160

Thr Leu Thr Glu Thr Asp Ile Gln Ala Leu Ala Ala Cys Ala Pro
                165                 170                 175

Val Pro Val Leu Val Asp Asn Thr Phe Ala Thr Pro Ala Leu Gln Arg
            180                 185                 190

Pro Leu Asn Arg Gly Ala Ala Ile Val Leu His Ser Ala Thr Lys Tyr
        195                 200                 205

Leu Gly Gly His Gly Asp Val Met Gly Gly Val Val Ala Ser Asn Glu
    210                 215                 220

Glu Phe Ala Arg Ala Leu Arg Arg Ile Arg Phe Ala Thr Gly Gly Ile
225                 230                 235                 240

Leu His Pro Leu Ala Gly Tyr Gln Leu Leu Arg Gly Leu Ser Thr Leu
                245                 250                 255

Ser Val Arg Met His His Ala Ser Ala Ser Ala Ala Glu Ile Ala Arg
            260                 265                 270

Arg Leu Leu His His Pro Ala Val Thr Arg Val His Tyr Pro Gly Leu
        275                 280                 285

Ser Gly Glu Pro Arg Pro Lys Gln Met Ala Ala Gly Gly Ala Ile
    290                 295                 300

Val Ser Phe Glu Val Asp Asp Pro His Ala Val Thr Gly Gly Val Arg
305                 310                 315                 320

Leu Phe Thr Pro Ala Val Ser Leu Gly Ser Val Asp Ser Leu Ile Gln
                325                 330                 335

His Pro Val Ser Leu Thr His His Ala Met Asp Pro Gly Ser Arg Glu
            340                 345                 350

Gln Ala Gly Ile Ser Asp Arg Leu Leu Arg Ile Ser Val Gly Leu Glu
        355                 360                 365

His Val Asp Asp Leu Trp Ala Asp Leu Thr Gln Ala Leu Thr Arg Asp
    370                 375                 380

<210> SEQ ID NO 18
<211> LENGTH: 155
<212> TYPE: PRT
<213> ORGANISM: Streptomyces tsukubaensis

<400> SEQUENCE: 18

Met Lys Glu Lys Val Val Leu Asp Ser Ile Asp Gln Ala Ile Leu Arg
1               5                   10                  15

Glu Leu Gln Asn Asp Gly Arg Leu Pro Asn Lys Thr Leu Ala Arg Arg
                20                  25                  30

Val Gly Val Ala Pro Ser Thr Cys Leu Ala Arg Thr Gln Arg Leu Met
            35                  40                  45

Glu Ala Gly Val Ile Arg Gly Phe Gln Ala Gln Val Ser Ala Ala Ala
        50                  55                  60

Ile Gly Arg Gln Val Gln Ala Val Leu Ala Val Gln Phe Ile Ala His
65                  70                  75                  80

Ser Arg Pro Phe Val Asp Pro Phe Val Ala Trp Ala Arg Glu Arg Pro
                85                  90                  95

Glu Thr Arg Ala Leu His His Val Thr Gly Ala Phe Asp Phe Leu Val
            100                 105                 110

His Thr Ala Cys Arg Asp Thr Glu Asn Leu Gln Gln Leu Val Leu Glu
        115                 120                 125
```

```
Phe Thr Ala Arg Arg Glu Val Gly Arg Val Glu Thr His Leu Val Phe
    130                 135                 140

Gly Ser Trp Ser Gly Gly Pro Leu Thr Pro Gly
145                 150                 155

<210> SEQ ID NO 19
<211> LENGTH: 409
<212> TYPE: PRT
<213> ORGANISM: Streptomyces tsukubaensis

<400> SEQUENCE: 19

Val Asp Arg Glu Pro Val Phe Val Leu Asp Pro Arg Gly Gly Asp Arg
1               5                   10                  15

His Gly Glu Asp Ala Ala Leu Arg Ala Arg Gly Pro Leu Thr Arg Val
            20                  25                  30

Asp Ala Leu Gly Val Glu Ala Trp Ser Val Thr Asp Pro Val Leu Leu
        35                  40                  45

Arg Arg Leu Leu Leu Asp Ser Arg Val Ser Lys Asn Ala Arg Gln His
50                  55                  60

Trp Pro Ala Phe Pro Glu Glu Ile Val Gly Val Trp Pro Leu Ala Leu
65                  70                  75                  80

Trp Val Ala Val Glu Asn Met Phe Thr Ala Tyr Gly Glu Glu His Arg
                85                  90                  95

Arg Leu Arg Arg Thr Ile Gly Pro Ala Phe Ala Ala Arg Ile Asn
            100                 105                 110

Ala Leu Ala Pro Val Ile Glu Gln Leu Val Gly Glu Leu Leu Asp Glu
        115                 120                 125

Leu Ala Ala Thr Pro Pro Gly Glu Pro Val Asp Leu Arg Glu His Phe
130                 135                 140

Ala Tyr Pro Leu Pro Ile Gly Val Val Gly Gln Leu Ala Gly Leu Pro
145                 150                 155                 160

Glu Ser Val Arg Pro Arg Phe Arg Arg Thr Val Asp Val Ile Phe Ser
                165                 170                 175

Thr Ser His Ser Pro Glu Glu Thr Thr Ala Ala Val Gln Asp Leu Tyr
            180                 185                 190

Ala Leu Leu Ala Asp Leu Val Ala Ala Lys Arg Ala Glu Pro Gly Asp
        195                 200                 205

Asp Leu Thr Ser Ala Leu Ile Ala Ala Arg Asp Thr Glu Gly Asp Gly
        210                 215                 220

Glu Pro Leu Thr Glu Ala Glu Leu Val Asp Thr Leu Leu Leu Val Val
225                 230                 235                 240

Asn Ala Gly Phe Glu Thr Thr Val Asn Leu Leu Asp Gln Ala Ile Thr
                245                 250                 255

Ala Leu Leu Thr Asp Pro Gly Gln Leu Ala His Val Arg Ala Gly Arg
            260                 265                 270

Ala Gly Trp Lys Asp Val Val Glu Glu Ser Leu Arg His Glu Ala Pro
        275                 280                 285

Leu Ala His Leu Pro Met Arg Phe Ala Val Glu Asp Ile Pro Leu Pro
290                 295                 300

Glu His Gly Val Thr Ile Arg Gln Gly Asp Ala Val Leu Pro Ala Tyr
305                 310                 315                 320

Ala Ala Ala Asn Arg His Pro Asp Leu His Gly Leu Thr Ala Asp Asp
                325                 330                 335

Phe Asp Ala Thr Arg Ser Asp Lys Ser His Leu Ser Phe Gly His Gly
            340                 345                 350
```

```
Met His Leu Cys Leu Gly Ala Ala Leu Gly Arg Leu Glu Ala Glu Ile
            355                 360                 365

Ala Leu Arg Gly Leu Phe Glu Arg Phe Pro Arg Leu Ala Leu Ala Val
    370                 375                 380

Pro Leu Asp Arg Leu Arg Pro Lys Pro Ser Phe Ile Ser Asn Gly His
385                 390                 395                 400

Ser Glu Leu Pro Val Ile Ile Asp Pro
                405

<210> SEQ ID NO 20
<211> LENGTH: 395
<212> TYPE: PRT
<213> ORGANISM: Streptomyces tsukubaensis

<400> SEQUENCE: 20

Val Gly Thr Pro Gln Pro Asp Val Ala Glu Gly Leu Thr Pro Val Glu
1               5                   10                  15

Ala Ala Arg Ser Leu Val Pro Leu Leu Ala Ala Glu Ala Ala Arg Thr
                20                  25                  30

Glu Glu Arg Arg Ala Leu Thr Gly Ala Thr Val Thr Gly Leu Arg Arg
            35                  40                  45

Ala Gly Leu Leu Arg Leu Gly Thr Pro Thr Glu Cys Gly Gly Arg Gly
        50                  55                  60

Ala Gly Ala Arg Thr Ala Val Asp Val Cys Glu Leu Ala Lys Gly
65                  70                  75                  80

Cys Ala Ser Ala Ser Trp Ile Val Gly Ile Ala Tyr Gly Gly Ala Leu
                85                  90                  95

Phe Ala Ser Gln Leu Pro His Ser Glu Arg Ala Ala Leu Trp Arg Asp
            100                 105                 110

Asp Pro Asp Ala Val Val Cys Gly Ser Ala Asn Pro Ser Gly Thr Ala
        115                 120                 125

Arg Arg Thr Asp Gly Gly Trp Thr Leu Ser Gly Arg Trp Pro Trp Ile
    130                 135                 140

Ser Gly Ile His His Ala Pro Trp Thr Leu Leu Gly Phe Val Arg Pro
145                 150                 155                 160

Gly Ala Gly Gly Glu Pro Glu Arg Gly Met Ala Val Val Pro Thr Ala
                165                 170                 175

Gly Leu Thr Val Glu Asp Val Trp His Met Ala Gly Met Arg Gly Thr
            180                 185                 190

Gly Ser Asp Thr Ala Val Ala Asp Gly Val Tyr Val Pro Asp Ser Arg
        195                 200                 205

Thr Ile Ser Leu Thr Ala Met Ala Asp Gly Ala Tyr Arg Arg His
    210                 215                 220

Pro Gly Glu Pro Arg Val Thr Phe His Leu Ser Ile Asn Leu Pro Leu
225                 230                 235                 240

Val Ala Thr Ala Val Gly Ile Ala Thr Ala Ser Leu Glu Lys Val Leu
                245                 250                 255

Asp Ala Ala Ala Arg Gly Lys Gln Thr Val Ser Pro Leu His Arg Leu
            260                 265                 270

Val Ala Glu Asp Ser Ala His Gln Leu Asn Val Ala Asp Ala Ala Thr
        275                 280                 285

Leu Ile Asp Thr Ala Arg Leu His Leu Arg Arg Ala Ala Asp Glu Val
    290                 295                 300

Asp Ser His Ala Arg Ala Gly Arg Arg Pro Ala Leu Ala Glu Arg Ala
```

```
                305                 310                 315                 320
        Arg Leu Arg Met Asp Ala Ala His Ala Met Arg Cys Ala Arg Asp Ala
                        325                 330                 335

Val Ser Leu Leu Leu Asp Thr Ala Gly Ala Gly Ser Phe Ala Asp Gly
                        340                 345                 350

Ser Val Leu Gln Arg Ala Trp Arg Asp Ile Glu Thr Ala Ser Arg His
                        355                 360                 365

Ala Ala Leu Ser Val Gln Thr Ser Lys Glu Ile Tyr Gly Arg Ala Leu
                        370                 375                 380

Leu Gly Ala Pro Leu Pro Pro Gly Pro Val Val
        385                 390                 395

<210> SEQ ID NO 21
<211> LENGTH: 218
<212> TYPE: PRT
<213> ORGANISM: Streptomyces tsukubaensis

<400> SEQUENCE: 21

Val Ala Leu Leu Asp Arg Asp Gly Asp Ala Val Thr Gly Leu Ser Ala
        1               5                   10                  15

Ala Leu Asp Pro Ala Gly Ala Gly Thr Ala Leu Pro Leu Arg Ala Asp
                        20                  25                  30

Val Asp Asp Thr Asp Ala Val His Ala Ala Leu Arg Glu Thr Ala Ala
                        35                  40                  45

Ala Trp His Ala Pro Asp Ile Leu Ile Asn Asn Ala Ala Arg Thr Ala
                        50                  55                  60

Pro Gly Ser Val Trp Asp Ile Glu Pro Asp Glu Trp Asp Ala Val Leu
        65                  70                  75                  80

Thr Thr Asn Leu Arg Ser Val Leu Thr Leu Thr Arg Leu Cys Ala Pro
                        85                  90                  95

Ala Met Arg Asp Arg Gly Trp Gly Arg Val Val Asn Leu Ser Ser Leu
                        100                 105                 110

Ala Gly Gln Gln Gly Gly Thr Leu Ala Gly Ala His Tyr Ser Ala Ala
                        115                 120                 125

Lys Ala Gly Val Leu Val Leu Thr Lys Val Phe Ala Arg Glu Leu Ala
                        130                 135                 140

Ala His Gly Val Thr Val Asn Ala Val Ala Pro Ala Ala Val Asp Thr
        145                 150                 155                 160

Pro Ala Val Ala Gly Leu Gly Pro Ser Ala Val Ala Glu Ala Ala Arg
                        165                 170                 175

Gln Ile Pro Val Gly Arg Met Gly Arg Pro Ser Glu Val Ala Gly Leu
                        180                 185                 190

Val Ala Tyr Leu Val Gly Glu Glu Gly Gly Tyr Val Thr Gly Ala Thr
                        195                 200                 205

Phe Asp Ile Asn Gly Gly Thr His Met Arg
            210                 215

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtctagacca catcatcggc tccgacc                                             27
```

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgaattcacg ccgaccttgc cctggtgc                                          28

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caagcttcac cggtcccggg ctc                                               23

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gcatatggtc cggttcgggg gtggg                                             25

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtcacata tggcgaacta ccggg                                             25

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgaattctgt gggccgacct caccca                                            26

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaattcgtt acggggagac ggcatcccgg                                        30

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
aggatccggg cgggctcgtc gcggt                                    25

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
tggatccggc gcgtatcgcc aaccgctac                                29

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
aaagcttccc ggtagttcgc catatgtgac ccg                           33

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
acatatgctc gggtcgttcg ttacggggag                               30

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
atctagaacg tgggtcatcg gctggtcctt g                             31

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
atctagaaca tgccctaggt acgtttcgcg g                             31

```
<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atctagaggc gttcggattc gctcaccg                                          28

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atctagaggg cggatacgtc accggcg                                           27

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccaagcttat ggagatcatc gaaggcagc                                         29
```

PROCESS FOR PREPARATION OF TACROLIMUS

CROSS-REFERENCE TO RELATED APPLICATION

This application is a National Stage entry of International Application No. PCT/EP2010/059896, filed Jul. 9, 2010, which claims priority to European Application No. 09165035.8, filed Jul. 9, 2009, the entire specifications, claims and drawings of which are incorporated herewith by reference.

SEQUENCE LISTING

The instant application contains a Sequence Listing which has been submitted in ASCII format via EFS-Web and is hereby incorporated by reference in its entirety. Said ASCII copy, created on Jun. 7, 2012, is named 02948900.txt and is 74,907 bytes in size.

The present invention relates to a process for the preparation of the immunosuppressive compound tacrolimus. It also is directed to genetically modified strains of the microorganism Streptomyces tsukubaensis (S. tsukubaensis) and to an improved fermentation process for the preparation of tacrolimus (FK-506) or salts or derivatives thereof by cultivating these genetically modified strains and then isolating the immunosuppressive compound.

Furthermore, the invention relates to new genes encoding enzymes for the allylmalonyl-CoA biosynthetic pathway in particular in S. tsukubaensis and located on the tacrolimus biosynthesis gene cluster and to genetically modified strains of S. tsukubaensis, wherein these genes are overexpressed and/or inactivated. WO 2010/004304, Moss et al. describes strains producing FK-506 or FK-520.

Tacrolimus, which is also referred to as FK-506 (Fermentek catalogue number 506), is a 23-membered macrolide lactone and belongs to the group of polyketides. Tacrolimus was first isolated in the 1980's from the fermentation broth of the soil bacteria Streptomyces tsukubaensis. The antibiotic macrolide compound tacrolimus was e.g. reported in 1984 by Kino et al. (J. Antibiotics 40, 1249-1255, 1984). Later on tacrolimus was prepared as a microbial natural product by using different microorganisms, i.e. soil bacteria such as Streptomyces sp. MA6858 (U.S. Pat. No. 5,116,756) ATCC 55098, Streptomyces tsukubaensis NRRL 18488 (EP-B 0 356 399 and U.S. Pat. No. 5,200,411), Streptomyces clavuligerus CKD 1119 (KR-B 100485877) or Streptomyces glaucescens MTCC 5115 (US 2007191415).

The product tacrolimus exhibits immunosuppressive activities which are due to its effect to reduce the activity of the enzyme peptidyl-propyl isomerase and to the binding to the protein immunophilin FKBP12 (FK506 binding protein). Tacrolimus and the structurally similar polyketides ascomycin and rapamycin require initial binding to the highly conserved protein cyclophilin FKBP12 in order to be physiologically active. The rapamycin/FKBP12 complex binds to mTOR (mammalian target of rapamycin), a serine-threonine kinase that appears to act as a central controller for sensing the cellular environment and regulating translation initiation (see e.g. Easton J. B. and Houghton P. J., 2004, Expert Opin Ther Targets; 8(6):551-64). However, the tacrolimus/FKBP12 complex was found to bind to a different cellular target and inhibits the phosphatase activity of calcineurin, in analogy to cyclosporine (see Allison A. C., 2000, Immunopharmacology; 47(2-3):63-83).

Tacrolimus is often used for immunosuppression following e.g. organ transplantation. Furthermore, tacrolimus and its derivatives have been shown to be effective in treating a number of diseases such as asthma, inflammatory diseases and hyperproliferative skin disease. Tacrolimus and other immunosuppressant such as rapamycin, cyclosporine, or a combination thereof are also useful in the treatment of various auto-immmune diseases. For many years calcineurin inhibitors (e.g. cyclosporine and tacrolimus) have been the mainstay of immunosuppressive therapy. These two compounds are potent suppressors of cellular immune response and have significantly improved the outcome of organ transplants during the past two decades (see Allison A. C., 2000, Immunopharmacology; 47(2-3):63-83).

Gene clusters encoding the biosynthetic pathways of a great number of medically important drugs of microbial origin have already been cloned and sequenced, including the gene cluster of macrolides rapamycin, ascomycin and tacrolimus. With respect to cloning of the tacrolimus gene cluster, a partial sequence, mostly encompassing genes encoding polyketide synthase (PKS), was reported in the literature (see Motamedi H. and Shafiee A. 1998, Eur J Biochem; 256(3): 528-34). On the other hand, scientists reported cloning of the ascomycin gene cluster in 2000 (see Wu K et al. 2000, Gene; 251(1):81-90, U.S. Pat. No. 6,503,737). Tacrolimus structurally and by the biosynthetic origin resembles ascomycin (FK520) and rapamycin (see Reynolds et al.; Drugs and the Pharmaceutical Sciences, 1997, 82, 497-520. They all can be synthesised by combined polyketide (PKS) and non-ribosomal peptide biosynthetic pathways (NRPS) (see McDaniel R et al. 2005, Chem Rev; 105(2):543-58).

Tacrolimus and ascomycin are structurally similar. As only structural difference, the allyl side chain at carbon 21 of tacrolimus is replaced by an ethyl side chain in ascomycin. The structures of tacrolimus (FK506) and ascomycin (FK520) compounds are shown as formulae (Ia) and (Ib).

The structures of ascomycin and tacrolimus already suggest complex biosynthetic pathways which can be divided into four steps considering the biosynthetic mechanism:

1. chain initiation using the unusual shikimate derived starter,
2. chain elongation common to most PKS derived compounds,
3. chain termination and cyclization by incorporation of L-pipecolic acid and
4. post-PKS processing.

During the tacrolimus fermentation process, undesired ascomycin (FK520) product is also produced as an impurity, thus lowering the final yield of tacrolimus and causing significant additional costs to the downstream isolation processes of tacrolimus.

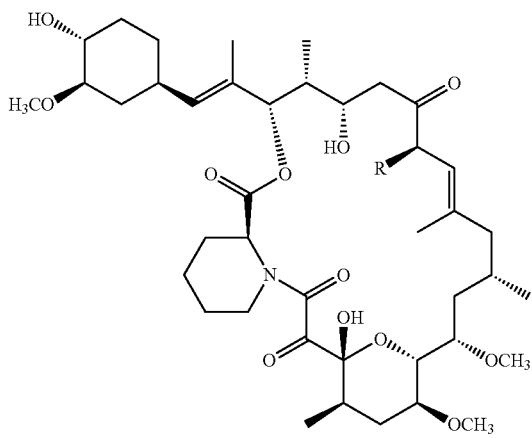

FK506, R=—CH$_2$—CH=CH$_2$ (Ia)

FK520, R=CH$_2$—CH$_3$ (Ib)

In particular, the present invention relates to the use of a compound of formula (Ia) or of formula (Ib) as defined above or an optical isomer, pharmaceutically acceptable salt, hydrate, solvate or polymorph thereof for the preparation of a medicament and for the treatment of a mammal, including humans. The invention relates to the use of a compound for the preparation of a medicament for the prevention and/or treatment of a condition or disease in an animal, including a human.

Ethylmalonyl-CoA is a known important building unit for ascomycin (FK-520) biosynthesis. The following genes which are located at the biosynthesis ascomycin cluster found in *S. hygroscopius* and involved in ascomycin biosynthesis are reported in the state of the art (see Liu et al., Journal of Bacteriology, 1999, 181, 6806-6813; Liu et al., Metabolic Engineering, 2001, 3, 40-48) and seem to be relevant:

a) gene encoding crotonyl-CoA reductase (ccr gene),
b) gene encoding B$_{12}$ dependent isobutyryl-CoA mutase (icm gene),
c) gene encoding ethylmalonyl-CoA mutase (ecm gene).

The biosynthetic pathways providing the ethylmalonyl-CoA extender unit in specific stages of polyketide chain assembly of several polyketide-derived compounds are described in the state of the art (see Wu et al., loc. cit.; Reynolds et al., loc. cit.). It seems that the ethylmalonyl-CoA extender unit is derived by the reaction of carboxylation of butyryl-CoA. At least two pathways leading to butyryl-CoA have been identified in *Streptomycetes*. One pathway involves a condensation of two acetate units, thus forming acetoacetate-CoA activated product, which is further processed to crotonyl-CoA and through a key step of reduction of crotonyl-CoA to butyryl-CoA, catalyzed by a crotonyl-CoA reductase (ccr) (see Wallace K. K. et al. 1995, Eur J Biochem; 233:954-962). This gene was first identified in *S. collinus* where it was found to be located within a set of primary metabolic genes. Later on, its homologues were identified within biosynthetic clusters encoding several compounds that require ethylmalonyl-CoA as a precursor (see Cropp et al., 2001, J Ind Microbiol Biotechnol; 27:368-377).

Recently, a ccr homologue in *Rhodobacter sphaeroides* was shown to encode an enzyme with crotonyl-CoA carboxylase/reductase activity, catalyzing reductive carboxylation of crotonyl-CoA to ethylmalonyl-CoA (see Erb T. J. et al. 2007, Proc Natl Acad Sci USA; 25: 10631-10636). Moreover, this enzyme was shown to be a part of a newly discovered acetate assimilation pathway termed "ethylmalonyl-CoA pathway" which enables growth of microorganisms lacking isocitrate lyase gene on acetate as the only carbon source. This pathway is predicted to involve several steps. It is initiated, similarly to previous predictions, by condensation of two acetyl-CoA units and subsequent processing to crotonyl-CoA. Crotonyl-CoA is then converted by Ccr directly to (2S)-ethylmalonyl-CoA which is first epimerized to (2R)-ethylmalonyl-CoA and later converted to methylsuccinyl-CoA by a vitamin B12-dependent ethylmalonyl-CoA mutase (ecm) (see Erb T. J. et al. 2008, J Biol Chem; 283: 32283-32293). Subsequently, methylsuccinyl-CoA is converted to mesaconyl-CoA by methylsuccinyl-CoA dehydrogenase and in the next step mesaconyl-CoA is converted to β-methylmalyl-CoA by mesaconyl-CoA dehydratase. Finally, β-methylmalyl-CoA is cleaved to glyoxylate and propionyl-CoA which then enter previously known metabolic pathways. Glyoxylate can be condensed with acetyl-CoA to yield malate and propionyl-CoA can be carboxylated to methylmalonyl-CoA and then succinyl-CoA. Interestingly, several *Streptomyces* species encode some of the genes involved in the ecm pathway as a cluster suggesting that this pathway is active in *Streptomyces* while growing on acetate butyrate or fatty acids as a single carbon source (see Akopiants K. et al. J Ind Microbiol Biotechnol; 33: 141-150).

A second pathway is proposed which proceeds through an isomerization step of a valine metabolite, isobutyryl-CoA, to form butyryl-CoA and is catalyzed by the coenzyme B12-dependent isobutyryl-CoA mutase (icm) (see Reynolds K. et al. 1988, J Chem Soc Perkin Trans 1; 3195-3207; and Zerbe-Burkhardt K. et al. 1998, J Biol Chem; 273:6508-6517).

The metabolic origin of allylmalonyl-CoA precursor and genes involved in its biosynthesis for tacrolimus (FK506) producing organisms have not been identified in the prior art.

The invention provides a new biosynthetic pathway for the provision of allylmalonyl-CoA. Surprisingly, a group of genes was found responsible for allylmalonyl-CoA biosynthesis, which is positioned in the left arm of the FK506 polyketide synthase (PKS) cluster. The newly obtained sequence of the extreme left side of the FK506-biosynthesis gene cluster was found to encode genes involved in allylmalonyl-CoA biosynthesis and is referred to as "Allyl(AII) cluster" or "Allyl(AII) subcluster" of the tacrolimus gene cluster (see Table 1).

The present invention relates to this novel nucleotide sequences containing genes, involved in the biosynthesis of allylmalonyl-CoA precursor (building block), which are located at the left side of the FK506 polyketide synthase (PKS) gene cluster.

The various uses of these sequences for the improvement of FK506 producing strains, in particular in terms of yields and purity, are also included in the present invention. The invention also provides a genetically modified strain having heterogeneously expressed "Allyl subcluster" that allows selective production of tacrolimus, ascomycin or related compounds.

It is one object of the present invention to provide an improved process for production of tacrolimus by reducing or abolishing the formation of by-products such as ascomycin and/or by increasing the yield of production of tacrolimus.

It was found that the availability of the extender unit allylmalonyl-CoA versus ethylmalonyl-CoA plays an important role in the final ratio of the wanted product tacrolimus (FK506) or respectively ascomycin (FK520) as by-product at the end of the fermentative process. The invention therefore provides several possibilities how to control the ratio of said extender units resulting in significantly improved ratios of the wanted product and by-products.

In this aspect, the present invention describes an improved fermentative preparation of tacrolimus carried out by genetically modified strain preferably by *Streptomyces tsukubaensis* (NRRL 18488) in which the biosynthesis of the product ascomycin (FK520) may be significantly reduced or abolished. Preferably, the yield of tacrolimus remains either constant or is increased. Thus, the process significantly reduces the disadvantages of known processes of fermentative production by employing means to reduce (or abolish) ethylmalonyl-CoA supply and/or by increasing the allylmalonyl-CoA biosynthesis. The process can reduce (or abolish) ascomycin production, and maintain or increase the production yield of tacrolimus.

The final ratios of tacrolimus on the one hand and of ascomycin on the other hand at the end of the process can be regulated by inactivating and/or over expressing these genes involved in the metabolism of ethylmalonyl-CoA and/or allylmalonyl-CoA.

Furthermore, the present application is directed to genetically modified strain of a microorganism, wherein the genetic material of the microorganism comprises at least one inactivated and/or over expressed gene involved in the metabolism and/or the biosynthesis of ethylmalonyl-CoA and/or allylmalonyl-CoA.

DETAILED DESCRIPTION OF INVENTION

The present invention is directed to a process for the preparation of tacrolimus, wherein the process comprises the step of cultivation of a genetically modified strain of a microorganism, preferably belonging to the genus *Streptomyces*, more preferably a genetically modified strain of *Streptomyces tsukubaensis*, wherein the genetic material of the microorganism comprises at least one inactivated and/or over expressed gene involved in the metabolism and/or the biosynthesis of ethylmalonyl-CoA and/or allylmalonyl-CoA.

The present invention also describes a genetically modified strain of a microorganism belonging to the genus *Streptomyces*, wherein the genetic material of the microorganism comprises at least one inactivated and/or over expressed gene involved in the metabolism and/or the biosynthesis of ethylmalonyl-CoA and/or allyl malonyl-CoA.

In particular the process for the preparation of tacrolimus according to the present application comprises at least one of the following steps:
a) Generation of genetically modified strain of a microorganism;
b) Preparation of seed medium comprising addition of genetically modified strain of a microorganism into a nutrient medium and cultivating said strain of a microorganism;
c) Main fermentation comprising addition of seed medium of genetically modified strain of a microorganism into a nutrient medium in a bioreactor, cultivating said strain of a microorganism and production of tacrolimus;
d) Separation and purification of product from the fermentation broth (harvest).

In particular the process for the preparation of tacrolimus according to the present invention comprises the generation of genetically modified strain of a microorganism, which is described in the present application, preparation of seed medium and main fermentation comprising cultivating said genetically modified strain of a microorganism. Preferably the process for the preparation of tacrolimus according to the present application comprises the steps a) to d) as mentioned above. The process steps a) to d) are described in more detail below.

In a preferred embodiment the invention deals with a process for the preparation of tacrolimus as mentioned above, wherein the process comprises the step of cultivation of a genetically modified strain of a microorganism wherein the microorganism is a bacterium preferably selected from genus *Streptomyces*. In particular the said microorganism may be selected from order Actinomycetales. Preferred is a microorganism belonging to order Actinomycetales having PKS activity or having heterologously expressed PKS or part thereof. More particularly the microorganism may be selected from the genus *Streptomyces*. Particularly *Streptomyces tsukubaensis*, *Streptomyces* sp. ATCC 55098 or *Streptomyces hygroscopicus* var. *ascomyceticus* ATCC 14891 may be used.

In particular the microorganism is selected from a genetically modified strain of *Streptomyces tsukubaensis*, preferably *Streptomyces tsukubaensis* (NRRL 18488). Further, the microorganism may be selected from a genetically modified strain of *Streptomyces hygroscopius*.

Moreover, it is also contemplated to use the following microorganisms for carrying out the process of the present invention: *Streptomyces tsukubaensis* No. 9993 (Ferm BP-927), *Streptomyces hygroscopicus* subsp. *hygroscopicus* (DSM 40822), *Streptomyces* sp. AA6554, *Streptomyces hygroscopicus* var. *ascomyceticus* MA 6475 ATCC 14891, *Streptomyces hygroscopicus* var. *ascomyceticus* MA 6678 ATCC 55087, *Streptomyces hygroscopicus* var. *ascomyceticus* MA 6674, *Streptomyces hygroscopicus* var. *ascomyceticus* ATCC 55276, *Streptomyces hygroscopicus* subsp. *ascomyceticus* ATCC 14891, *Streptomyces kanamyceticus* KCC S-0433, *Streptomyces clavuligerus* CKD1119, *Streptomyces hygroscopicus* subsp. *yakushimaensis*, *Streptomyces* sp. DSM 7348, *Micromonospora* n.sp. A92-306401 DSM 8429, *Streptomyces* sp. MA 6548 and *Streptomyces* sp. MA 6858 ATCC 55098.

In another aspect the invention relates to a process for the preparation of tacrolimus as described in the present application, wherein the process comprises the step of cultivation of a genetically modified strain of a microorganism preferably belonging to the genus *Streptomyces*, wherein the process is carried out under the external addition of allylmalonyl-CoA and/or at least one precursor of allylmalonyl-CoA. In particular allylmalonyl-CoA and/or at least one precursor of allylmalonyl-CoA are added to the fermentation medium in the main fermentation process (step c) as described above.

Furthermore, the fermentative process described in the present application may comprise cultivating a genetically modified strain of a microorganism preferably belonging to the genus *Streptomyces*, more preferably a genetically modified strain of *Streptomyces tsukubaensis*, as provided by this invention, and adding in a controlled manner allylmalonyl-, ethylmalonyl-, and/or propylmalonyl-CoA and/or precursors of allylmalonyl-, ethylmalonyl-, and/or propylmalonyl-CoA to the fermentation medium. Substantially pure tacrolimus, ascomycin or related compounds respectively, can be thus obtained. In this sense a genetically modified strain of a microorganism preferably belonging to the genus *Streptomyces*, more preferably a genetically modified strain of *Streptomyces tsukubaensis*, having inactivated at least AllR gene according to SEQ.ID.#4, has to be used.

In another embodiment the process for the preparation of tacrolimus as described in the present application comprises the step of cultivation of a genetically modified strain of a microorganism, preferably belonging to the genus *Strepto-*

*myces*, more preferably a genetically modified strain of *Streptomyces tsukubaensis*, wherein the genetic material of the microorganism comprises at least one inactivated and/or over expressed gene selected from gene sequence of Allyl-subcluster according to SEQ.ID.#1, which is composed of the following genes AllA gene according to SEQ.ID.#2, AllK gene according to SEQ.ID.#3, AllR gene according to SEQ.ID.#4, AllD gene according to SEQ.ID.#5, AllM gene according to SEQ.ID.#6, AllN gene according to SEQ.ID.#7, AllP gene according to SEQ.ID.#8, AllO gene according to SEQ.ID.#9, and AllS gene according to SEQ.ID.#10. The nucleotide sequences mentioned above are described in table 1 and listed in the appendix.

The entire gene cluster encoding ORFs (open reading frame) required for the biosynthesis of FK506 was sequenced. In addition to the published sequence of the central part of the cluster which contains the PKS (polyketide synthase) genes (see Motamedi H. and Shafiee A. 1998, Eur J Biochem; 256(3):528-34), the sequences of the genes present to the left and right fringe of the polyketide synthase cluster were obtained and annotated. On the left side of the gene cluster, a number of ORFs were identified, the majority of which did not show any homology to the genes present in the ascomycin (FK520) biosynthesis cluster (see Wu K et al. 2000, Gene; 251(1):81-90, U.S. Pat. No. 6,503,737). BLAST search using these ORFs as a query revealed the putative functions of the identified genes as presented in the Table 1.

This Allyl-cluster (or Allyl-subcluster) encoding genes are involved in the biosynthesis of allylmalonyl-CoA precursor specifically required for the biosynthesis of tacrolimus. Further, it was found that the Allyl-subcluster encoding genes are involved in the biosynthesis of ethylmalonyl-CoA.

In a further aspect, the invention deals with nucleotide sequences of Allyl-subcluster involved in ethylmalonyl-CoA or allylmalonyl-CoA biosynthesis of an microorganismen belonging to the genus *Streptomyces* comprising the sequence according to SEQ.ID #1, which is composed of several genes according to SEQ.ID #2 to SEQ.ID #10, and variants thereof comprising one or more nucleotide additions, deletions, substitutions or inversions. The nucleotide sequences of Allyl-subcluster are shown in table 1 and listed in appendices (SEQ.ID #1 to SEQ.ID #10).

TABLE 1

Organization of the Allylmalonyl-CoA Biosynthesis Part (Allyl cluster or All-cluster) of the Tacrolimus Gene Cluster

| SEQ. ID. # | Gene Name | Gene Function | Start | Stop | Length (bp) | Length (AA) | Start Codon | Stop Codon |
|---|---|---|---|---|---|---|---|---|
| 2 | AllA | Acyltransferase and acyl-Carrier Protein | 2775 | 4067 | 1551 | 517 | ATG | TGA |
| 3 | AllK | Ketoacyl synthase | 4078 | 6465 | 2428 | 776 | ATG | TGA |
| 4 | AllR | Acyl CoA reductase | 6465 | 7799 | 1335 | 445 | ATG | TGA |
| 5 | AllD | Acyl-CoA dehydrogenase | 7799 | 8956 | 1158 | 386 | GTG | TAG |
| 6 | AllM | Methionine gamma lyase | 10126 | 8975 | 1152 | 384 | ATG | TGA |
| 7 | AllN | Transcriptional regulator | 10186 | 10650 | 465 | 155 | ATG | TAG |
| 8 | AllP | P450 monooxygenase | 10757 | 11983 | 1326 | 442 | CTG | TAG |
| 9 | AllO | Acyl-CoA oxidoreductase | 12171 | 13358 | 1185 | 395 | GTG | TGA |
| 10 | AllS | Acetoacetyl-CoA reductase | 13467 | 14120 | 654 | 218 | GTG | TGA |

It was found that by blocking synthesis of ethylmalonyl-CoA and allylmalonyl-CoA in a mutant strain, a new process is possible in which by feeding these building blocks one can control which polyketide is produced. It was found that inactivation of AllR gene encoding oxidoreductases (similar to crotonyl-CoA reductase) entirely abolished the production of tacrolimus. However external feeding with allylmalonyl-CoA precursors enables exclusive production of tacrolimus, with abolished production of ascomycin in the fermentation broth. It was also found that inactivation of AllR gene entirely abolished the production of ascomycin (FK-520). However with external feeding of ethylmalonyl-CoA precursors enables exclusive production of ascomycin (FK-520), with abolished production of tacrolimus in the fermentation broth.

This process is possible in any ascomycin or tacrolimus producing organism. Method for blocking synthesis of ethylmalonyl-CoA in an ascomycin producing organism is well known to a person skilled in art, as genes responsible for ethylmalonyl-CoA biosynthesis have been elucidated in ascomycin producing organisms (Wu et al. 2000, Gene 251, 81-90). Inactivation of ccr homologues would be the first step in preparation of such organism. Since PKS for synthesis for ascomycin and tacrolimus are highly homologous, the promiscuity of module 7, incorporating allylmalonyl-CoA or ethylmalonyl-CoA can be expected for PKS of all ascomycin/tacrolimus producing organisms.

In one embodiment of the invention the process for the preparation of tacrolimus as described in the present application comprises the step of cultivation of a genetically modified strain of a microorganism belonging to the genus *Streptomyces*, preferably a genetically modified strain of *Streptomyces tsukubaensis*, wherein the process is carried out under the external addition of allylmalonyl-CoA and/or at least one precursor of allylmalonyl-CoA.

Different allylmalonyl-CoA precursors can be used. More particularly the addition of allylmalonyl-SNAC (allylmalonyl-(N-acetyl-cysteamine)thioester) is preferred. In terms of the present invention allylmalonyl-CoA precursors also includes analogues of allylmalonyl-CoA.

Alternatively, allylmalonic acid or analogue thereof can be directly used in said process given additional genetic modification of the strain used for the process. In this case malonyl-CoA synthetase and dixarboxylate carrier protein have to be expressed in the used microorganism. An example of genetically modified microorganism capable of incorporation of dicarboxylate compounds provided in the growth medium is described by Lombo et al. Biotechnol. Prog. 2001, 17, 612-617. Sufficient activity of malonyl-CoA synthetase for allylmalonic acid as a substrate is described by Pohl et al. J. Am. Chem. Soc. 2001, 123, 5822-5823.

In particular the process as described above comprises the step of cultivation of a genetically modified strain of a microorganism belonging to the genus *Streptomyces*, wherein the genetic material of the microorganism comprises at least one inactivated and/or over expressed gene selected from the group of
AIIK gene according to SEQ.ID.#3 and
AIIR gene according to SEQ.ID.#4.

In further embodiment of the invention the process as described above comprises the step of cultivation of a genetically modified strain of a microorganism belonging to the genus *Streptomyces*, preferably to a genetically modified strain of *Streptomyces tsukubaensis*, wherein the genetic material of the microorganism comprises additionally inactivated gene ccr gene according to SEQ.ID.#11.

In this particular aspect the invention relates to the following strains of *Streptomyces tsukubaensis:*
a) *Streptomyces tsukubaensis* F499
deposited with the deposition number DSM 22507 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 ΔaIIR.
b) *Streptomyces tsukubaensis* F872
deposited with the deposition number DSM 22509 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 ΔaIIK.

In a further embodiment of the invention the process as described above comprises the step of cultivation of a genetically modified strain of a microorganism belonging to the genus *Streptomyces*, preferably to a strain of *Streptomyces tsukubaensis*, wherein the genetic material of the microorganism comprises at least one inactivated gene selected from Allyl-subcluster according to SEQ.ID.#1, which is composed of the following genes AIIA gene according to SEQ.ID.#2, AIIK gene according to SEQ.ID.#3, AIIR gene according to SEQ.ID.#4, AIID gene according to SEQ.ID.#5, AIIM gene according to SEQ.ID.#6, AIIN gene according to SEQ.ID.#7, AIIP gene according to SEQ.ID.#8, AIIO gene according to SEQ.ID.#9, and AIIS gene according to SEQ.ID.#10, and wherein the process is carried out under the external addition of allylmalonyl-CoA and/or at least one precursor of allylmalonyl-CoA.

In a preferred embodiment the process as described above comprises the step of cultivation of a genetically modified strain of a microorganism belonging to the genus *Streptomyces*, wherein the genetic material of the microorganism comprises at least one inactivated gene selected from the group of AIIK gene according to SEQ.ID.#3 and AIIR gene according to SEQ.ID.#4, and wherein the process is carried out under the external addition of allylmalonyl-CoA and/or at least one precursor of allylmalonyl-CoA.

In a preferred embodiment the process as described above comprises the step of cultivation of a genetically modified strain of a microorganism belonging to the genus *Streptomyces*, preferably to a genetically modified strain of *Streptomyces tsukubaensis*, wherein the genetic material of the microorganism comprises inactivated AIIR gene according to SEQ.ID.#4 and inactivated ccr gene according to SEQ.ID.#11, and wherein the process is carried out under external addition of allylmalonyl-CoA and/or at least one precursor of allylmalonyl-CoA.

Further the present invention relates to a nucleotide sequence encoding one or several gene(s) involved in the metabolism and/or the biosynthesis of ethylmalonyl-CoA and/or allylmalonyl-CoA of an microorganism belonging to the genus *Streptomyces*, comprising the sequence according to SEQ ID #1, which is composed of the following genes AIIA gene according to SEQ.ID.#2, AIIK gene according to SEQ.ID.#3, AIIR gene according to SEQ.ID.#4, AIID gene according to SEQ.ID.#5, AIIM gene according to SEQ.ID.#6, AIIN gene according to SEQ.ID.#7, AIIP gene according to SEQ.ID.#8, AIIO gene according to SEQ.ID.#9, and AIIS gene according to SEQ.ID.#10, and variants thereof comprising one or more nucleotide addition(s), deletion(s), substitution(s) and/or inversion(s).

In particular the nucleotide sequence as described above has at least 50% nucleotide identity with SEQ. ID.#1.

Also provided by the invention is a nucleotide sequence as described above wherein the nucleotide sequence has at least 60% nucleotide identity, preferably at least 70%, preferably at least 80%, preferably at least 90% with sequence according to SEQ.ID #1, which is composed of several genes according to SEQ.ID #2 to SEQ.ID10#. The above described variants of the nucleotide sequences should retain the capacity to encode the enzymes involved in the ethylmalonyl- or allylmalonyl-CoA biosynthesis of an organism belonging to the genus *Streptomyces*.

In this sense the invention provides nucleotide sequence of every individual gene as listed in Table 1 and described in SEQ.ID #2 to SEQ.ID #10 and their amino acid products described in SEQ.ID #13 to SEQ.ID #21 and variants thereof comprising one or more nucleotide addition(s), deletion(s), substitution(s) and/or inversion(s), wherein the nucleotide sequence has at least 50% nucleotide identity, preferably at least 60%, preferably at least 70%, preferably at least 80%, preferably at least 90% with sequence according to sequence which is composed of several genes according to SE D #2 to SEQ.ID10#.

The proposed biosynthetic pathway can be described as follows. In order to obtain allylmalonyl-CoA, a C5 precursor, valeryl-CoA or 4-pentenoyl-CoA should first be formed. Analogously to ethylmalonyl-CoA, originating from two acetate units through acetoacetate and crotonyl-CoA, propylmalonyl-CoA or allylmalonyl-CoA can emerge from one 3-carbon and one 2-carbon unit. The genes AIIA (acyltransferase) and AIIK (ketosynthase) have been identified, which carry out condensation reaction as single-step by a rather short polyketide synthase (PKS)-like enzyme complex. It is not clear, how 5-carbon intermediate (3-oxopentanoic acid or its reduced intermediate) is activated by the addition of CoA or is transferred directly to the FK506 PKS complex, before it is further processed to the final allylmalonyl-CoA, a C5-precursor. Feeding experiments with final synthetic allyl precursor however indicate ability of FK506 PKS to incorporate the extender in the final allylmalonyl-CoA form. The putative AIIS gene, homologous to acetoacetyl-CoA reductase, carries out the first reduction step yielding 3-hydroxypentanoyl-CoA. Additional oxidoreductases (AIIR—similar to crotonyl-CoA carboxylase/reductase, AIID and AIIO) can then further reduce this compound to propylmalonyl-CoA and in concert with the AIIP, P450 monooxygenase, also introduce an —OH group and subsequently a double bond in the position 4, yielding allylmalonyl-CoA. This is then introduced to the nascent polyketide chain by the corresponding acyltransferase (AT4) gene on the PKS module 4. As a part of the Allyl cluster, ORF designated as AIIM were identified. This gene product shows homology to the methionine gamma lyase and likely converts methionine to 2-oxobutyrate that readily metabolizes to propionyl-CoA, a starter unit required for biosynthesis of the first 5-carbon intermediate by the AIIA. Propionyl-CoA precursor can be limiting during secondary metabolism.

Therefore, the presence of the AIIM gene product is likely needed for sufficient provision of propionyl-CoA in order to increase the yield of the final product FK-506.

The proposed pathway also explains the origin of the ethylmalonyl-CoA and thereby also the origin of FK-520 in fermentation broths of FK-506-producing microorganisms. Genes, present in the >>Allyl subcluster<< of the FK-506 biosynthetic cluster of S. tsukubaensis, involved in biosynthesis of allylmalonyl-CoA, can also produce ethylmalonyl-CoA. Namely the enoyl CoA reductase (gene AIIR) most probably shows limited promiscuity to acetoacetate (C4) unit instead of the C5 unit (3-oxopentanoic acid or its reduced intermediate), which is then processed in a similar manner as in the pathway, described above. The subsequent steps proceed in a similar manner for both precursors; however, the C4 unit seems not to be a substrate for P450 mediated hydroxylation and formation of the double bond. Deletion of enoyl-CoA reductase/carboxylase (AIIR) gene was found to completely abolish this biosynthetic pathway and production of FK-506 and FK-520. Deletion of ketoacyl synthase (AIIK) gene was found to completely abolish only production of FK-506, production of FK-520 remain on the level of wild type S. tsukubaensis strain.

Interestingly, the reaction steps described above leading to ethylmalonyl-CoA and allylmalonyl-CoA (or propylmalonyl-CoA) extender units for FK-520/FK-506 biosynthesis, mechanistically closely resemble the initial reactions of the "ethylmalonyl-CoA pathway" up to the point where ethymalonyl-CoA intermediate is formed. This primary metabolic pathway is most probably involved in the growth of most Streptomyces species on acetate as the sole carbon source and involves ethylmalonyl-CoA as an intermediate compound, produced by crotonyl-CoA carboxylase/reductase (ccr), which is further converted to methylsuccinyl-CoA by ethylmalonyl-CoA mutase (ecm). Clearly, one would expect that this pathway, if active under the given growth conditions, can also represent an important source of ethylmalonyl-CoA in S. tsukubaensis. However, many genes encoding "ethylmalonyl-CoA pathway", including ccr—which produces ethylmalonyl-CoA- and ecm—which processes it further—are located in the same operon in Streptomyces and are most likely co-transcribed. Such gene architecture is ideal when both genes must act in concert and substrates must be rapidly passed through the metabolic pathway to end-products, but may come short of providing sufficient amounts of a single intermediate, namely ethylmalonyl-CoA, as a building block for secondary metabolism. This may provide an explanation why many gene clusters for polyketide biosynthesis, which require ethylmalonyl-CoA as an extender unit, also contain an additional copy of a ccr gene homologue, in this context without the ecm gene that would immediately consume ethylmalonyl-CoA produced.

Although the reactions involved are mechanistically similar, the enzymes providing allylmalonyl-CoA (propylmalonyl-CoA) and ethylmalonyl-CoA as building blocks for FK-506 and FK-520 biosynthesis in S. tsukubaensis and the enzymes of the "ethylmalonyl-CoA pathway" of this organism differ in one important aspect. While "ethylmalonyl-CoA pathway" specifically involves ethylmalonyl-CoA intermediate and only small amounts of propylmalonyl-CoA might eventually be formed, the enzymes encoded by the all subcluster show a different specificity. They predominantly produce allylmalonyl-CoA (propylmalonyl-CoA) while ethylmalonyl-CoA is produced in small amount. The amounts are probably relatively small because some enzymes of the pathway (namely AIIR) can accept 4-carbon and 5-carbon intermediates with similar efficiency while others might be very specific for substrates leading exclusively to allylmalonyl-CoA (propylmalonyl-CoA). In the context of a fermentative process for production of FK-506 by Streptomyces enzymes both metabolic systems may be expressed although their expression is most probably induced by completely different factors. While genes of the all subcluster are probably transcribed together with other genes of the FK-506 biosynthetic cluster once secondary metabolism is induced, the expression and activity of "ethylmalonyl-CoA pathway" enzymes is most likely dependent on growth conditions, most importantly on the composition of the growth medium.

Clearly, in order for concentration of ethylmalonyl-CoA and thereby yield of FK-520 to be kept as low as possible, the composition of growth medium should be adapted so that the genes of the "ethylmalonyl-CoA pathway" are not transcribed or are transcribed at minimum level. Alternatively, the expression of enzymes which take part in the ecm pathway and which are usually encoded on the same operon in Streptomyces, has to be engineered in order to keep ethylmalonyl-CoA concentrations low. The ccr gene encoding crotonyl-CoA carboxylase/reductase should be inactivated while the other four genes encoding ethylmalonyl-CoA mutase (ecm), methylsuccinyl-CoA dehydrogenase, mesaconyl-CoA dehydratase and β-methylmalyl-CoA lyase should be overexpressed using a strong consitutive promoter. However, if complete abolishment of ethylmalonyl-CoA in the cells is desired independently of growth conditions and medium, it may be necessary to introduce target mutations which interrupt both pathways at the same mechanistic step. As described in this invention, this step may be the inactivation of both ccr homologues, the ccr gene of the "ethylmalonyl-CoA pathway" as well as the aIIR gene of the all subcluster involved predominantly in the provision of allylmalonyl-CoA (propylmalonyl-CoA).

One object of invention is to provide a process for the preparation of tacrolimus, wherein the process comprises the step of cultivation of a genetically modified strain of a microorganism, preferably belonging to the genus Streptomyces, more preferably a genetically modified strain of Streptomyces tsukubaensis, wherein the genetic material of the microorganism is modified so that it improves ratio of intracellular pool of allylmalonyl-CoA versus ethylmalonyl-CoA.

In this embodiment the process for the preparation of tacrolimus as described in the present invention comprises the step of cultivation of a genetically modified strain of a microorganism, preferably belonging to the genus Streptomyces, more preferably a genetically modified strain of Streptomyces tsukubaensis, wherein the genetic material of the microorganism comprises at least one over expressed gene selected from gene sequence of Allyl-subcluster according to SEQ.ID.#1, which is composed of the following genes AIIA gene according to SEQ.ID.#2, AIIK gene according to SEQ.ID.#3, AIIR gene according to SEQ.ID.#4, AIID gene according to SEQ.ID.#5, AIIM gene according to SEQ.ID.#6, AIIN gene according to SEQ.ID.#7, AIIP gene according to SEQ.ID.#8, AIIO gene according to SEQ.ID.#9, and AIIS gene according to SEQ.ID.#10. The nucleotide sequences mentioned above are described in table 1 and listed in the appendix.

The present application involves the generation of the S. tsukubaensis strain(s) with inactivated and/or over expressed one or several of the genes listed in Table 1, encoding proteins necessary for allylmalonyl-CoA and/or ethylmalonyl-CoA precursor synthesis.

More particularly in this aspect the present invention is directed to the generation of genetically modified strain of *Streptomyces tsukubaensis* wherein the strain comprises at least one inactivated gene involved in the provision of key building units for tacrolimus (FK-506) and/or ascomycin (FK-520) biosynthesis. These genetically modified strains have been found to be useful for the improved production of tacrolimus.

Methods for genetically modification of a microorganism are known in the art, e.g. amplification of gene copy number. Another example is insertion of additional copies of said genes under control of a strong promoter. Yet another example in this sense is modification of activity of transcriptional regulator found in the "AII" subcluster.

In this sense the invention provides an improved strain of *Streptomyces tsukubaensis* for fermentative production of tacrolimus by improving intracellular pool of allylmalonyl-CoA precursor and or reducing intracellular pool of ethylmalonyl-CoA. The novel nucleotide sequences according to table 1 and SEQ. ID #1, can be used to regulate the expression of said genes involved in biosynthesis of allylmalonyl-CoA.

In one embodiment of the invention the process for the preparation of tacrolimus as described in the present application comprises the step of cultivation of a genetically modified strain of a microorganism, wherein the genetic material of the microorganism comprises at least one inactivated and/or over expressed gene selected from crotonyl-CoA reductase (ccr) gene according to SEQ.ID.#11, and ethylmalonyl-CoA mutase (ecm) according to SEQ.ID.#12. Nucleotide sequences are listed in the appendix.

The present application is directed to a genetically modified strain of a microorganism belonging to the genus *Streptomyces*, preferably a genetically modified strain of *Streptomyces tsukubaensis*, wherein the genetic material of the microorganism comprises at least one inactivated and/or over expressed gene involved in the metabolism and/or the biosynthesis of ethylmalonyl-CoA and/or allylmalonyl-CoA.

In particular the present application is directed to a genetically modified strain of a microorganism belonging to the genus *Streptomyces* as described above, wherein the genetic material of the microorganism comprises at least one inactivated and/or over expressed gene selected from gene sequence of Allyl-subcluster according to SEQ.ID.#1, which is composed of the following genes AIIA gene according to SEQ.ID.#2, AIIK gene according to SEQ.ID.#3, AIIR gene according to SEQ.ID.#4, AIID gene according to SEQ.ID.#5, AIIM gene according to SEQ.ID.#6, AIIN gene according to SEQ.ID.#7, AIIP gene according to SEQ.ID.#8, AIIO gene according to SEQ.ID.#9, and AIIS gene according to SEQ.ID.#10.

In particular the present invention is directed to a genetically modified strain of a microorganism belonging to the genus *Streptomyces* as described above, preferably a genetically modified strain of *Streptomyces tsukubaensis*, wherein the genetic material of the microorganism comprises at least one overexpressed gene selected from the group of AIIA gene according to SEQ.ID.#2, AIIK gene according to SEQ.ID.#3 and AIIR gene according to SEQ.ID.#4.

In particular the present application is directed to a genetically modified strain of a microorganism belonging to the genus *Streptomyces* as described above, preferably a genetically modified strain of *Streptomyces tsukubaensis*, wherein the genetic material of the microorganism comprises at least one overexpressed gene selected from the group of AIIA gene according to SEQ.ID.#2 and AIIK gene according to SEQ.ID.#3.

In another, yet similar embodiment, the novel nucleotide sequences containing genes, involved in the biosynthesis of allylmalonyl-CoA precursor allow a person skilled in the art the construction of recombinant strains for production of tacrolimus. In this sense any ascomycin producer microorganism can be engineered to produce tacrolimus. A suitable microorganism in this sense may be but is not limited to *Streptomyces hygroscopicus*. This can be achieved by transfer of said nucleotide sequences to said host strain by methods known in the art.

Further, present invention deals with a genetically modified strain of a microorganism, wherein said strain has a native or engineered polyketide synthase activity.

The present invention also relates to a genetically modified strain of *Streptomyces tsukubaensis*, wherein the genetic material of the microorganism comprises at least one inactivated and/or over expressed gene selected from the group of
- AIIR gene according to SEQ.ID #4, encoding distant homologue of the crotonyl-CoA reductase,
- AIIP gene according to SEQ.ID #8, encoding a cytochrome P450 enzyme,
- AIIA gene according to SEQ. ID #2, encoding an acyltransferase enzyme and acyl carrier protein,
- AIIK gene according to SEQ. ID #3, encoding a ketoacyl synthase enzyme,
- AIID gene according to SEQ.ID.#5, encoding an acyl-CoA dehydrogenase enzyme,
- AIIM gene according to SEQ. ID #6, encoding a Methionie gamma lyase enzyme and acyl carrier protein,
- AIIN gene according to SEQ. ID. #7, encoding a transcriptional regulator,
- AIIO gene according to SEQ. ID #9, encoding an Acyl-CoA oxidoreductase enzyme, and
- AIIS gene according to SEQ.ID #10, encoding an acetoacetyl-CoA reductase enzyme.

The nucleotide sequences (DNA sequences) of the genes and the amino acid sequences of the gene products are shown in the appendix SEQ.ID #2 to SEQ.ID #10 and SEQ.ID #13 to SEQ. ID #21, respectively.

In this particular aspect the invention relates to the following strains of *Streptomyces tsukubaensis:* a) *Streptomyces tsukubaensis* F499
deposited with the deposition number DSM 22507 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 ΔaIIR b) *Streptomyces tsukubaensis* F872
deposited with the deposition number DSM 22509 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 ΔaIIK, c) *Streptomyces tsukubaensis* F917
deposited with the deposition number DSM 22511 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 AIIP+.

Furthermore, the nucleotide sequences containing genes involved in the biosynthesis of allylmalonyl-CoA precursor can be used to produce novel, hybrid polyketides. This can be achieved by transfer of said nucleotide sequences to any polyketide producing host strain microorganism by methods known in the art. Due to promiscuity of polyketide synthase (PKS) modules which is well known, one can expect at least traces of new hybrid polyketide compounds having allyl side chain in at least one carbon position.

The microorganism, which can be used for the genetic modification (over expression or inactivation of the said genes) may be selected from bacteria. More particularly the said microorganism is selected from order Actinomycetales. Preferred is a microorganism belonging to order Actinomycetales having PKS (polyketide synthase) activity. Alternatively the organism for over expression may be any microorganism having heterologously expressed PKS or part thereof.

More particularly the microorganism is selected from the genus *Streptomyces*. Particularly *Streptomyces tsukubaensis, Streptomyces* sp. ATCC 55098 or *Streptomyces hygroscopicus* var. *ascomyceticus* ATCC 14891 may be used.

Moreover, it is also contemplated to use the following microorganisms for carrying out the process of the present invention: *Streptomyces tsukubaensis* No. 9993 (Ferm BP-927), *Streptomyces hygroscopicus* subsp. *hygroscopicus* (DSM 40822), *Streptomyces* sp. AA6554, *Streptomyces hygroscopicus* var. *ascomyceticus* MA 6475 ATCC 14891, *Streptomyces hygroscopicus* var. *ascomyceticus* MA 6678 ATCC 55087, *Streptomyces hygroscopicus* var. *ascomyceticus* MA 6674, *Streptomyces hygroscopicus* var. *ascomyceticus* ATCC 55276, *Streptomyces hygroscopicus* subsp. *ascomyceticus* ATCC 14891, *Streptomyces kanamyceticus* KCC S-0433, *Streptomyces clavuligerus* CKD1119, *Streptomyces hygroscopicus* subsp. *yakushimaensis, Streptomyces* sp. DSM 7348, *Micromonospora* n.sp. A92-306401 DSM 8429, *Streptomyces* sp. MA 6548 and *Streptomyces* sp. MA 6858 ATCC 55098.

In one embodiment, this invention refers to the use of the second group of the genes which are not clustered at the specific FK506 gene cluster on the *S. tsukubaensis* chromosome. These genes are involved in the metabolism of butyryl-CoA and ethylmalonyl-CoA, a precursor for biosynthesis of ascomycin (FK520).

In order to reduce or abolish ethylmalonyl-CoA supply in *S. tsukubaensis*, several strategies were followed. In this respect, the invention relates to the use of nucleotide sequences of genes which are involved in the metabolism of ethylmalonyl-CoA, a building unit for ascomycin biosynthesis encoding the following enzymes:
  a) crotonyl-CoA reductase (referred to as ccr respectively as ccr-gene hereinafter),
  b) ethylmalonyl-CoA mutase (referred to as ecm respectively as ecm-gene hereinafter).

The nucleotide sequences and amino acid sequences are listed in the appendix (see SEQ.ID.#11, SEQ.ID.#12).

In this aspect the present application is directed to a process for the preparation of tacrolimus, wherein the process comprises the step of cultivation of a genetically modified strain of a microorganism, preferably of the genus *Streptomyces*, more preferably a genetically modified strain of *Streptomyces tsukubaensis*, wherein the genetic material of the microorganism comprises at least one inactivated and/or over expressed gene selected from crotonyl-CoA reductase (ccr) gene according to SEQ.ID.#11, and ethylmalonyl-CoA mutase (ecm) gene according to SEQ.ID.#12.

In particular the process for the preparation of tacrolimus comprises the step of cultivation of a genetically modified strain of a microorganism, preferably of the genus *Streptomyces*, more preferably a strain of *Streptomyces tsukubaensis*, wherein the genetic material of the microorganism comprises inactivated crotonyl-CoA reductase (ccr) gene according to SEQ.ID.#11.

In particular the process for the preparation of tacrolimus comprises the step of cultivation of a genetically modified strain of a microorganism, preferably of the genus *Streptomyces*, more preferably a strain of *Streptomyces tsukubaensis*, wherein the genetic material of the microorganism comprises over expressed ethylmalonyl-CoA mutase (ecm) gene according to SEQ.ID.#12.

This improved process for the preparation of tacrolimus exhibits significantly reduced or abolished production of ascomycin (FK520), thus significantly simplifying the tacrolimus purification process.

Gene homologues of ccr and icm were identified in several organisms to be involved in the biosynthesis of butyryl-CoA and consequently ethylmalonyl-CoA. The coenzyme B12-dependent isobutyryl-CoA mutase (icm; butanoyl-CoA:2-methylpropanoyl-CoA mutase, EC 5.4.99.13) catalyzes the reversible rearrangement between isobutyryl-CoA and n-butyryl-CoA in a reaction closely related to the known methylmalonyl-CoA mutase (mcm) reaction. Crotonyl-CoA reductase (EC 1.3.1.38, acyl-CoA:NADP$^+$ trans-2-oxidoreductase) catalyzes the conversion of crotonyl-CoA to butyryl-CoA, a key substrate for ethylmalonyl-CoA biosynthesis or, under some circumstances, directly converts crotonyl-CoA to ethylmalonyl-CoA. Gene homologues of ecm (ethylmalonyl-CoA mutase) have been shown to convert ethylmalonyl-CoA to methylsuccinyl-CoA thereby effectively altering the ratio of ethyl-substituted products in the mixture.

It is known that crotonyl-CoA reductase genes (ccr-gene) and ethylmalonyl-CoA mutase genes (ecm-genes) are involved in several metabolic and biosynthetic pathways in different microorganismen. The role of ecm and ccr in the polyketide biosynthesis, in particular in the biosynthesis of ethylmalonyl-CoA, have been described (e.g. the role of ecm in production of monensin in *S. cinnamonensis*, Zhang W. et al. 2001, J. Bacteriol; 183:2071-2080).

Therefore, the present invention describes a method of producing a microorganism having reduced intracellular level of ethylmalonyl-CoA. This is achieved by blocking enzymes involved in biosynthesis of ethylmalonyl-CoA and/or over expressing enzymes consuming ethylmalonyl-CoA.

The activity of crotonyl-CoA reductase (ccr) specifically involved in the biosynthesis of key building units for the biosynthesis of FK506/520 in *Streptomyces tsukubaensis* was modified. In addition, ethylmalonyl-CoA mutase (ecm), involved in further processing of ethylmalonyl-CoA, was over expressed in the tacrolimus producing strain *Streptomyces tsukubaensis*.

In one embodiment the present application is directed to a genetically modified strain of a microorganism, preferably belonging to the genus *Streptomyces*, more preferably a genetically modified strain of *Streptomyces tsukubaensis*, wherein the genetic material of the microorganism comprises at least one inactivated and/or over expressed gene selected from the group of
  ccr gene according to SEQ.ID.#11, encoding crotonyl-CoA reductase, and
  ecm gene according to SEQ.ID.#12, encoding ethylmalonyl-CoA mutase.

In a preferred embodiment the genetically modified strain of a microorganism as described in the present application is a double modified microorganism, which comprises two inactivated and/or over expressed genes as described in the present application. It was found, that double modified microorganism has substantially improved characteristics compared to wild type microorganism as well as single mutants.

The inactivation of crotonyl-CoA reductase gene homologue (ccr) and over expression of ethylmalonyl-CoA mutase (emc) lead to an improved process for production of tacrolimus, characterized by a significant reduction of ascomycin biosynthesis. It seems that under the tested growth conditions the mutase-catalyzed reaction proceeds from butyryl-CoA to isobutyryl-CoA. The ethylmalonyl-CoA mutase (ecm) gene was found to effectively consume ethylmalonyl-CoA when over expressed in the producing strain.

In one aspect, the invention provides a genetically modified microorganism, preferably of the genus *Streptomyces*, more preferably a strain of *Streptomyces tsukubaensis*, wherein the genetic material of the microorganism comprises inactivated crotonyl-CoA reductase gene (ccr) according to SEQ. ID. #11. The method of inactivating such gene in microorganism is well known in the art, for example as described in the handbook "Practical *Streptomyces* genetics" (Kieser et al., 2000, Practical *Streptomyces* genetics, A laboratory Manual. ISBN0-7084-0623-8).

In another aspect, the invention provides a genetically modified microorganism, preferably of the genus *Streptomyces*, more preferably a strain of *Streptomyces tsukubaensis*, wherein the genetic material of the microorganism comprises over expressed ethylmalonyl-CoA mutase gene (ecm) according to SEQ. ID. #12. The method of over expressing such gene in a microorganism is well known in the art, for example as described in the handbook "Practical *Streptomyces* genetics" (Kieser et al., 2000, Practical *Streptomyces* genetics, A laboratory Manual. ISBN0-7084-0623-8).

In a further aspect, the present invention provides a genetically modified microorganism, preferably of the genus *Streptomyces*, more preferably a strain of *Streptomyces tsukubaensis*, comprising inactivated crotonyl-CoA reductase gene (ccr) according to SEQ. ID. #11 and over expressed ethylmalonyl-CoA mutase (ecm) according to SEQ. ID. #12 as said above. In this aspect the use of double modified microorganism has substantially improved characteristics compared to wild type microorganism as well as single mutants described above.

In particular the invention relates to the following strains of *Streptomyces tsukubaensis*:

a) *Streptomyces tsukubaensis* F130
deposited with the deposition number DSM 22506 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 Δccr:Ts.

b) *Streptomyces tsukubaensis* F879
deposited with the deposition number DSM 22510 on 23 Apr. 2009, at the DSMZ—Deutsche Sammlung von Mikroorganismen und Zellkulturen GmbH (German Collection of Microorganism and Cell Cultures) in Braunschweig/Germany. This strain is described as NRRL 18488 ecm+.

The newly developed strains exhibits markedly reduced ascomycin content representing a significant improvement of tacrolimus fermentative production.

Further provided by the invention is the above mentioned nucleotide sequence encoding gene involved in ethylmalonyl-CoA biosynthesis of an microorganism *Streptomyces tsukubaensis* NRRL 18488 comprising the ccr gene sequence according to SEQ. ID #11, the sequence encoding for crotonyl-CoA reductase (Ccr), having amino acid sequence according to SEQ. ID #23, and variants thereof comprising one or more nucleotide additions, deletions, substitutions or inversions. Also provided by the invention is the nucleotide sequence encoding gene involved in ethylmalonyl-CoA consumption of an microorganism *Streptomyces tsukubaensis* NRRL 18488 comprising the ecm gene sequence according to SEQ. ID #12, the sequence encoding for ethylmalonyl-CoA mutase (ecm), having amino acid sequence according to SEQ. ID #24, and variants thereof comprising one or more nucleotide additions, deletions, substitutions or inversions. Also, provided by the invention is a nucleotide sequence as described above wherein the nucleotide sequence have at least 50% identity, preferably at least 60% identity, preferably at least 70%, preferably at least 80%, preferably at least 90% with sequence according to SEQ. ID #11 and SEQ. ID #12.

The present invention provides an improved process for the preparation of tacrolimus, in particular an industrial fermentative process, wherein the process comprises the step of cultivation of a genetically modified strain of a microorganism, wherein the genetic material of the microorganism comprises at least one inactivated and/or over expressed gene involved in the metabolism and/or the biosynthesis of ethylmalonyl-CoA and/or allylmalonyl-CoA. The process can be carried out by using at least one of the genetically modified strains of a microorganism as described above. In the following this process is described in more detail:

In particular the process according to the present invention comprises the following steps:

Step a) Generation of Genetically Modified Strain of a Microorganism

Preferably the present process for the production of tacrolimus encompasses the step of genetically modification of microorganism strains as described by this invention. In this sense the invention specifically relates to a genetically modified strain of *Streptomyces tsukubaensis* wherein the genetic material of the strain comprises at least one inactivated and/or over expressed gene involved in the metabolism and/or biosynthesis of ethylmalonyl-CoA and/or allylmalonyl-CoA.

Procedures to generate *Streptomyces tsukubaensis* for further modification according to the present invention are known to the person skilled in the art. Moreover, suitable strains of *Streptomyces tsukubaensis* are commercially available. One specific, non-limiting example of a suitable strain is the wild type *Streptomyces tsukubaensis* having the deposit number NRRL 18488.

The method of inactivating gene in microorganism is well known in the art, for example as described in the handbook "Practical *Streptomyces* genetics" (Kieser et al., 2000, Practical *Streptomyces* genetics, A laboratory Manual. ISBN0-7084-0623-8).

In a preferred embodiment a preparation of spores respectively a concentrated spore suspension in a sporulation medium of genetically modified strain of microorganism preferably a stain of *S. tsukubaensis* is carried out.

Step b) Preparation of Seed Medium

Cultivation of the modified strains of *Streptomyces tsukubaensis* as described in the present invention can be carried out by methods known to a person skilled in art. Cultivation processes of *Streptomyces tsukubaensis* are for example described in the handbook "Practical *Streptomyces* genetics" (Kieser et al., 2000, Practical *Streptomyces* genetics, A laboratory Manual. ISBN0-7084-0623-8).

Preferably the production of seed microorganism which can be used in the main fermentation process for the production of tacrolimus starts from a spore form of said genetically modified microorganism. In this respect the process according to the present application comprises the preparation of spore stock of described genetically modified microorganism, preferably of *Streptomyces tsukubaensis*, and optionally a concentrated spore suspension of described genetically modified microorganism. This preparation of spore form may be carried out using method known in the state of art, such as using a sporulation medium comprising a salt of manganese. Preferably this spore stock or concentrated spore suspension of genetically modified strain of microorganism is used to produce a vegetative seed medium by inoculation to a vegetative medium. The production of vegetative form of described microorganism should prepare with inoculation of a relatively small quantity of seed medium with the spores.

The seed medium may be transferred aseptically to a bioreactor.

In principle the cultivating of seed microorganism can be carried out under the conditions (e.g. pH, and temperature) as in the main fermentation process (described under step c).

Step c) Main Fermentation Process

Preferably the main fermentation process using genetically modified microorganism as described in the present application is carried out in a bioreactor in particular under agitation and/or aeration. Preferably, the process for the production of tacrolimus as described in the present application is carried out under submerged aerobic conditions in aqueous nutrient medium (production medium), containing sources of assimilable carbon, nitrogen, phosphate and minerals. Isolation of tacrolimus, which was produced in the main fermentation process from the said medium, may be carried out in a further separation step (step d).

Preferably the main fermentation process comprises the inoculation of production medium with seed microorganism obtained in step b) in particular by aseptically transfer into the reactor. It is preferred to employ the vegetative form of the microorganism for inoculation.

The addition of nutrient medium (production medium) in the main fermentation process into the reactor can be carried out once or more batch-wise or in a continuous way. Addition of nutrient medium (production medium) can be carried out before and/or during the fermentation process.

The preferred sources of carbon in the nutrient media can selected from dextrin, glucose, soluble starch, glycerol, lactic acid, maltose, fructose, molasses and sucrose as exemplified below.

The preferred sources of nitrogen in the nutrient media are yeast extract, soy peptone, soybean meal, bacterial peptone, casein hydrolysate, L-lysine, ammonium sulphate, corn steep liquor and other.

Inorganic/mineral salts such as calcium carbonate, sodium chloride, sodium or potassium phosphate, magnesium, manganese, zinc, iron and other salts may also be added to the medium.

The main fermentation process by the present process is carried out at a pH in the range of about 6.3 to 8.5 and temperature in the range of 20 to 35° C. Preferably the pH is in the range of about 6.5 to 8.3 and the temperature is in the range of about 23 to 31° C.

Preferably, the production cultures are incubated for 80 to about 300 hours, more preferably for about 130 to 280 hours.

The production of tacrolimus could be performed in aerobic conditions with agitation and aeration of production medium. Agitation and aeration of the culture mixture may be accomplished in a variety of ways. The agitation of production medium may be provided by a propeller or similar mechanical device and varied to various extents according to fermentation conditions and scale. The aeration rate can be varied in the range of 1.0 to 2.5 VVM (gas volume flow per unit of liquid volume per minute (volume per volume per minute)) with respect to the working volume of the bioreactor.

Further known additives for fermentative process may be added in particular in the main fermentation process. To prevent excessively foaming of the culture medium anti-foaming agents could be added, such as silicone oil, fatty oil, plant oil and the like. Particularly a silicone-based anti-foaming agent may be added during the fermentation process to prevent excessively foaming of the culture medium.

Step d) Separation and Purification of Product from the Fermentation Broth (Harvest)

Tacrolimus from the fermentation broth can be separated and purified by conventional methods commonly used for recovery of biologically active substances. The produced tacrolimus can be recovered from the fermentation broth by extraction in organic solvent i.e. acetone, ethanol or methanol.

Optionally the extract may be then concentrated, column chromatographed with XAD16 adsorber using acetone: water mixture to get crude tacrolimus. The crude substance may be further purified on preparative HPLC to get pure tacrolimus.

A preferred embodiment of process steps according to the present application can be summarized as follows:
i) Preparation of the *S. tsukubaensis* spore stocks from the said strains by cultivating said strains on the solid sporulation agar medium at 28° C. for 10 to 14 days.
ii) Spores of the *S. tsukubaensis* strains were harvested to produce concentrated spore suspension and inoculation to the 600 mL of vegetative medium and incubate on the shaker at 220 rpm for 24-32 hours until PMV 10-20% of vegetative medium is reached. pH at the harvest time is in the range of 6.8 to 7.3.
iii) Propagation of seed vegetative inoculum to the desired volume of 10% in order to inoculate production medium. 10 liter fermenter containing of vegetative medium is inoculated with vegetative seed and cultivated for 24 to 28 hours at 28° C.
iv) 10% of the vegetative seed culture is used to inoculate 100 L of the production medium. Fermentation process is carried out for 120 to 180 hours at 28° C. and pH maintained at 7.0-7.2 using sulphuric acid or sodium hydroxide solution.

In the following as a non limiting example preferred media for sporulation, seed growth and main fermentative process are described:
1) Solid agar sporulation medium (ISP4) comprised of soluble starch (10 g/L), sodium chloride (1 g/l), ammonium sulphate (2 g/L), calcium carbonate (2 g/L), $K_2HPO_4$ (1 g/l), $MgSO_4 \times 7H_2O$ (1 g/L), $FeSO_4 \times 7H_2O$ (0.001 g/L), $MnCl_2 \times 4H_2O$ (0.001 g/L), $ZnSO_4 \times 7H_2O$ (0.001 g/L) and bacteriogical agar (20 g/L). The pH should be adjusted to 7.0±0.2 prior to sterilization by suitable addition of base or acid.
2) Seed medium comprised of soybean meal (2.5 g/L), dextrin (10 g/L), glucose (1 g/L), yeast extract (5 g/L), casein hydrolizate (7 g/L), $K_2HPO_4$ (0.2 g/L), NaCl (0.5 g/L), $MnCl_2 \times 4H_2O$ (0.005 g/L), $FeSO_4 \times 7H_2O$ (0.025 g/L), $ZnSO_4 \times 7H_2O$ (0.001 g/L), $MgSO_4 \times 7H_2O$ (0.005 g/L) and $CaCl_2$ (0.02 g/L). The pH should be adjusted to 7.0±0.2 prior to sterilization by suitable addition of base or acid.
3) Production medium containing dextrin (60-120 g/L), glucose (0-15 g/L), soybean meal (5-20 g/L), soya peptone (5-20 g/L), glycerol (5-20 g/L), L-lysine (1-7.5 g/L), $K_2HPO_4$ (0.5-2 g/L), $CaCO_3$ (1-5 g/L) and polyethylene glycol (1-5 g/L). The pH should be adjusted to 7.0±0.2 prior to sterilization by suitable addition of base or acid.

In another preferred embodiment of the invention the main fermentation process (step c) is carried out under external addition of allylmalonyl-CoA or at least one precursor (analogue) of allylmalonyl-CoA. In terms of the present invention allylmalonyl-CoA precursors also includes analogues of allylmalonyl-CoA.

In this respect, the present invention provides a process for the preparation of tacrolimus, in particular an industrial fermentative process, wherein the process comprises the step of cultivation of a genetically modified strain of a microorganism belonging to the genus *Streptomyces*, wherein the genetic material of the microorganism comprises at least one inactivated and/or over expressed gene involved in the metabolism and/or the biosynthesis of ethylmalonyl-CoA and/or allylmalonyl-CoA and wherein the process is carried out under the external addition of allylmalonyl-CoA and/or at least one precursor (analogue) of allylmalonyl-CoA.

In particular the invention is directed to a fermentative preparation of tacrolimus (or related compounds) by cultivating a genetically modified strain of *S. tsukubaensis*, wherein the biosynthetic pathway(s) providing allylmalonyl- and ethylmalonyl CoA-activated precursors is inactivated, for example by inactivation of AIIR gene, and adding or feeding in controlled manner allylmalonyl-CoA or ethylmalonyl-CoA SNAC precursors into the culture medium during the fermentation process. This results in the production of tacrolimus or ascomycin compounds in the significant amounts compared to the wild-type strain. Thus, the novel process described herein resulted in process in which tacrolimus or ascomycin are produced exclusively, this way significantly simplifying the downstream process.

The fermentation process for the production of pure tacrolimus or pure ascomycin under external addition of allylmalonyl-CoA or ethylmalonyl-CoA or at least one precursors (analogues) thereof described herein using genetically modified strains of a microorganism belonging to genus *Streptomyces*, in particular a genetically modified strain of *S. tsukubaensis*, may be carried out under submerged aerobic conditions in aqueous nutrient medium, containing sources of assimilable carbon and nitrogen similar as described earlier.

Preferably, the target concentration range of the allylmalonyl or ethylmalonyl ester precursors is in the range of 0.1 to 5.0 g/L and more preferably in the range of 0.5 to 3.0 g/L. The target concentration may be recorded on a tangible data storage medium, preferably before the commencement of the fermentation process. For the feeding process different allylmalonyl or ethylmalonyl ester precursors could be used. Allylmalonyl or ethylmalonyl N-acetyl cysteamine (SNAC) thioesters are preferred. Both, single or double thioesters, or mixtures thereof can be used.

Tacrolimus from the fermentation broth can be separated and purified by conventional methods commonly used for recovery of biologically active substances. The process thus has significant cost advantages compared to classic process where preparative HPLC has to be employed in the downstream process.

Furthermore, the present invention deals with the use of genetically modified strain of *Streptomyces tsukubaensis* as described above in a process for the fermentative production of tacrolimus.

In a further aspect, the present invention relates to a pharmaceutical composition comprising tacrolimus or a pharmaceutically acceptable derivative or analog thereof produced by cultivation of a genetically modified strain of *Streptomyces tsukubaensis* as described above. The term "analog" or "derivative" is used herein in the conventional pharmaceutical sense, to refer to a molecule that structurally resembles a reference molecule, but has been modified in a targeted and controlled manner to replace one or more specific substituents of the referent molecule with an alternate substituent, thereby generating a molecule which is structurally similar to the reference molecule. In addition, using methods known to those skilled in the art, analogs and derivatives of the compound tacrolimus can be created which have improved therapeutic efficacy, i.e., higher potency and/or selectivity at a specific targeted receptor type, either greater or lower ability to penetrate mammalian blood-brain barriers (e.g., either higher or lower blood-brain barrier permeation rate), fewer side effects, etc.

The phrase "pharmaceutically acceptable", as used in connection with compositions of the invention, refers to molecular entities and other ingredients of such compositions that are physiologically tolerable and do not typically produce untoward reactions when administered to a mammal, e.g., a human. Preferably, as used herein, the term "pharmaceutically acceptable" means approved by a regulatory agency of the Federal or a state government or listed e.g. in the U.S. Pharmacopeia or other generally recognized pharmacopoeia for use in mammals, and more particularly in humans.

A further embodiment of the invention is a pharmaceutical composition comprising at least one compound of formula (I) or a polymorphic form thereof or a pharmaceutically acceptable salt thereof and at least one further pharmaceutically tolerable additive. The pharmaceutical composition can also comprise a further drug compound. In the pharmaceutical compositions of the present invention, the compounds of formula (I), in particular tacrolimus, or a polymorphic form or pharmaceutically acceptable salt thereof is formulated as dosage units containing e.g. from 0.1 to 4000 mg, preferably 1 to 2000 mg, of said compound or a pharmaceutically acceptable salt thereof per dosage unit for daily administration. For all aspects of the invention, particularly medical ones, the administration of a compound or composition has a dosage regime which will ultimately be determined by the attending physician and will take into consideration such factors such as the compound being used, animal type, gender, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man.

The physiologically acceptable compound according to the invention will normally be administered in a daily dosage regimen (for an adult patient) of, for example, an oral dose of between 0.01 mg/kg (mg per kilogram of body weight of the mammal to be treated) and 100 mg/kg, preferably between 0.1 mg/kg and 75 mg/kg.

Figure 1:
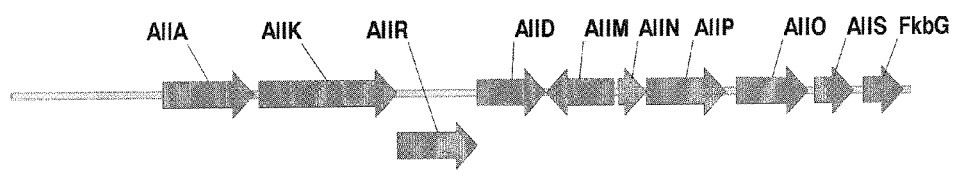
FIG. 1 shows the genetic organisation of "All-gene"-subcluster (15080 bp) of *Streptomyces tsukubaensis*.

The SEQ-ID # and the gene function are given in table 2:

TABLE 2

| SEQ. ID. # | Gene Name | Gene Function |
|---|---|---|
| 2. | AllA | Acyltransferase and acyl-Carrier Protein |
| 3. | AllK | Ketoacyl synthase |
| 4. | AllR | Enoyl CoA reductase |
| 5. | AllD | Acyl-CoA dehydrogenase |
| 6. | AllM | Methionine gamma lyase |
| 7. | AllN | Transcriptional regulator |
| 8. | AllP | P450 monooxygenase |
| 9. | AllO | Acyl-CoA oxidoreductase |
| 10. | AllS | Acetoacetyl-CoA reductase |

The following examples are for illustrating the present invention.

EXPERIMENTAL PROCEDURES

The following are detailed examples of the experimental procedures used to clone and analyse "ccr", "AIIK", "AIIR", "AIIP" and "ecm" genes, and for the generation of Streptomyces tsukubaensis mutants using these gene homologues. Also included are examples of fermentation procedures using these strains and determinations of FK506 and FK520 production yields. Additional details of standard techniques, which are well known to those skilled in molecular biology or microbiology, and the designation of the particular enzymes used, are described, for example, in the handbook "Practical Streptomyces genetics" (Kieser et al., 2000, Practical Streptomyces genetics, A laboratory Manual. ISBN0-7084-0623-8).

Example 1

Maintenance and Spores Preparation of Streptomyces tsukubaensis Strains

Streptomyces tsukubaensis strains mycelium were grown as a confluent lawn on the sporulation medium ISP4 for 8-14 days at 28° C. The ISP4 medium comprised:

| | | |
|---|---|---|
| Soluble starch | 10 | grams |
| K$_2$HPO$_4$ | 1 | gram |
| MgSO$_4$ × 7 H$_2$O | 1 | gram |
| NaCl | 1 | gram |
| (NH$_4$)$_2$SO$_4$ | 2 | grams |
| CaCO$_3$ | 2 | grams |
| FeSO$_4$ × 7 H$_2$O | 0.001 | gram |
| MnCl$_2$ × 4 H$_2$O | 0.001 | gram |
| ZnSO$_4$ × 7 H$_2$O | 0.001 | gram |
| Bacteriological agar | 20 | grams |
| Final volume | 1 | liter |
| pH adjusted to | 7.0 | |

The pH was adjusted to 7.0 with 1 M NaOH. Sterilization was performed at 121±2° C., 120±10 kPa for 20 minutes. After 8-14 days of growth, spores were collected and stored at −20° C. in glycerol (20%) until use.

Example 2

Preparation of Streptomyces tsukubaensis Genomic DNA

Spores of Streptomyces tsukubaensis NRRL 18488 (wild type) were used to inoculate 50 ml of TSB medium (Kieser et al., 2000, Practical Streptomyces genetics, A laboratory Manual. ISBN-0-7084-0623-8) in a 250-ml Erlenmeyer flask, which was maintained with shaking (210 rpm) at 28° C. for 24 hours. Cultures were grown for 24 hours at 28° C. Mycelium was recovered by centrifugation and genomic DNA was prepared using PureLink Genomic DNA Mini Kit (Invitrogen) according to the instructions of the kit manufacturer. DNA was resuspended in 100 μl TE buffer (Sambrook, and Russell, 2000, Molecular Cloning: A Laboratory Manual, ISBN-978-087969577-4).

Example 3

The isolated Genomic DNA was sequenced with Roche FLX technology at GATC AG, Germany. Once the sequence contigs belonging to the FK506 biosynthesis genetic cluster were identified the position and orientation of open reading frames (ORFs) was analyzed using the FramePlot beta 4.0. Software (Ishikawa et al., FEMS Microbiot Lett 174 (1999) 251-253). Using the predicted amino acid sequences, homology searches were carried out in GenBank databases using BLASTp and BLASTx algorithm at the NCBI (NCBI/Blast: http://blast.ncbi.nlm.nih.gov/Blast.cgi). Based on these results and supported by conserved domain searches, putative gene functions were assigned.

In total 15 ORFs were identified to the left from fkbC. Six of these show high similarity with the ORFs present in the FK520 cluster (fkbL—lysine cyclodeaminase, fkbG, fkbH, fkbI, fkbJ, fkbK—five genes involved in methoxymalonyl-ACP biosynthesis) and nine genes were predicted to form the "allyl subcluster". This subcluster consists of 1 gene containing acyltransferase and acyl carrier protein domains, 1 gene containg a ketoacyl synthase domain, 1 distant crotonyl-CoA reductase domain, 2 distant acyl-CoA dehydrogenase domain containing homologues, 1 methionine gamma lyase containing gene, 1 AsnC family regulator gene, 1 P450 monooxygenase gene and 1 distant acetoacetyl-CoA reductase homologue.

Example 4

Construction of Vectors for Disruption of the Ccr Gene, Construction of Mutant Strains of S. Tsukubaensis NRRL 18488 with Inactivated Ccr Gene and Analysis of Tacrolimus and Ascomycin Production of the Said Mutants a) Design of primers: Primers for amplification of a large region of ccr gene were designed based on conserved regions of other known ccr genes of different Streptomyces species, found using BLAST search with ccr gene from Streptomyces coelicolor (Protein ID: NP_630556.1, GeneID:1101912) as template, and a ClustalW pile-up sequence comparison of the obtained BLAST results. Thus, ccr-F2 (GTCTAGACCACAT-CATCGGCTCCGACC) (SEQ ID NO: 22) with an XbaI restriction site and ccr-R1 (CGAATTCACGCCGAC-CTTGCCCTGGTGC) (SEQ ID NO: 23) with an EcoRI restriction site were made to amplify a 917 bp long region of ccr gene.

b) PCR amplification of DNA fragments: S. tsukubaensis genomic DNA obtained in Example 2 was PCR amplified using a Biorad iCycler Thermal Cycler. The PCR reaction was carried out with Pfu polymerase (New England Biolabs) and the buffer provided by the manufacturer in the presence of 200 μM dNTP, 10% glycerol, 0.5 μM of each primer, approximately 50 ng of template S. *tsukubaensis* genomic DNA and 2.5 units of enzyme in a final volume of 100 µl for 30 cycles. The thermal profile of all 30 cycles was 95° C. for 45 sec (denaturation step), 69° C. for 45 sec (annealing step), and 72° C. for 1 min (extension step). The PCR-amplified product was cloned into a pUC19 cloning vector. The sequence analysis of the cloned PCR product confirmed its respective partial ccr sequence.

c) Construction of a temperature-sensitive pKC1139-based and suicide pKC1132-based vectors to be used in the disruption of the *S. tsukubaensis* ccr gene by homologous recombination: The F2-R1 amplified fragment of ccr gene was excised from pUC19 by EcoRI and XbaI restriction sites and the transferred by ligation into vectors pKC1139 and pKC1132 which were previously cut with EcoRI and XbaI restriction enzymes, making pKC1139-ccr and pKC1132-ccr. Vector pKC1139 contains a normal pUC19-based Ori for replication in *E. coli*, but a temperature-sensitive Ori for replication in *Streptomyces*, which is unable to function at elevated temperatures above 34° C. (Bierman et al., 1992 Gene. 116(1):43-9, Muth et al., 1989 Mol Gen Genet. 219(3): 341-348). Vector pKC1132 only contains the normal pUC19-based Ori for replication in *E. coli* but cannot maintain replication in *Streptomyces* (Bierman et al., 1992 Gene. 116(1):43-9) and is, thus, lost without integration into genome by homologous recombination. Vectors pKC1139-ccr1 and pKC1132-ccr were then opened using BamHI restriction enzyme which cuts within the ccr gene, splitting the 917 bp long fragment into 346 bp on one side and 571 bp on the other side, which were then blunt-ended with DNA Polymerase I, Large (Klenow) Fragment. A cassette, conferring thiostrepton (Ts) resistance, was then introduced into pKC1139-ccr and pKC1132-ccr BamHI-cut and blunt-ended vectors. The p330 vector was digested with XbaI restriction enzyme, the approximately 961 bp long fragment containing the Ts cassette was blunt-ended with DNA Polymerase I, Large (Klenow) Fragment and ligated into the pKC1139-ccr and pKC1132-ccr vectors, making pKC1139-ccrTs and pKC1132-ccrTs vectors, respectively.

d) Introduction of vectors for disruption of the ccr gene into the *S. tsukubaensis* NRRL 18488 strain: Plasmid constructs pKC1139-ccrTs and pKC1132-ccrTs were introduced by transformation into electrocompetent *E. coli* strain ET12567 containing the conjugative plasmid pUZ8002 (Paget et al., 1999 J. Bacteriol. 181: 204-211). The plasmid pUZ8002 contains all the necessary genes for construction of conjugative pilli, however it lacks the origin of transfer and, thus, remains in the host cell (Jones et al., 1997 Mol. Microbiol. 23:169-178). Conjugation procedure was done as described in Kieser et al., 2000 (Practical *Streptomyces* genetics, A laboratory Manual. ISBN0-7084-0623-8). Only transformation with vector pKC1139-ccrTs gave exconjugants. Exconjugants were grown at 28° C. on Sporulation medium which is described in Example 1 with addition of 50 µg/ml apramycin.

e) Selection for stable secondary recombinant strains of *S. tsukubaensis* with disrupted ccr gene by thiostrepton resistance conferring cassette: *S. tsukubaensis* exconjugants of vector pKC1139-ccrTs, grown at 28° C. on Sporulation medium with addition of 50 µg/ml apramycin were inoculated into liquid TSB medium with thiostrepton (25 µg/ml) and grown in shake flasks at 28° C. and 210 rpm without the addition of apramycin to produce good seed culture. After 24 h, seed culture was subcultivated into a new shake flask with fresh TSB medium with thiostrepton (25 µg/ml) and grown at an increased temperature, higher than 24° C. and 210 rpm. Above 34° C. the pKC1139-based vector is unable to replicate and is forced to integrate into the *S. tsukubaensis* genome, thus yielding primary recombinants. The culture was further subcultivated several times into new shake flasks with fresh TSB medium with thiostrepton (25 µg/ml), and then plated onto Sporulation medium with thiostrepton and grown at 28° C. Harvested spores were filtered and serial dilution was made on plates of Sporulation medium. After 5-8 days single colonies were patched onto plates with Sporulation medium with thiostrepton, and on plates of Sporulation medium with thiostrepton and apramycin. Primary recombinants are still resistant to apramycin, while secondary recombinants lost the apramycin resistance and cannot grow on Sporulation medium with apramycin. Selected secondary recombinant strains were also confirmed by Southern hybridization as described in next paragraph.

f) Analysis of *S. tsukubaensis* ccr-disrupted mutants genomic DNA by Southern Hybridization: Preparation of DIG-labelled plasmid DNA probe: Only the insert (part of the ccr gene with inserted $Ts^R$ cassette) of the plasmid pKC1139-ccrTs was used as a probe; the vector was digested with EcoRI and XbaI restriction enzymes and the 1.744 bp long fragment purified with a Wizard SV Gel and PCR Clean-Up System (Promega). Approximately 1 µg of the eluted fragment was labelled overnight with digoxigenin-dUTP by random primed labelling technique using the DIG High Prime DNA Labelling and Detection Starter Kit I (Roche).

i) DNA transfer: Genomic DNA of *S. tsukubaensis* wild type and pKC1139-ccrTs mutants (putative primary recombinants and secondary recombinants) was prepared using the PureLink Genomic DNA Mini Kit (Invitrogen) according to the instructions of the kit manufacturer. Approximately 10 µg of each isolated genomic DNA was digested with NaeI restriction enzyme. At the end of the digestion, the DNA fragments were separated by electrophoresis in a 1% agarose gel at 20 V for 12 hours, and transferred to a positively charged Hybond-N+ nylon membrane (GE Healthcare) using the alkali capillary blotting method (Southern, E. M., 1975, J. Mol. Biol., 98:503) for 6 hours.

ii) Hybridisation: Pre-hybridization and hybridization of DIG-labeled DNA probe to DNA immobilized on a nylon membrane was performed as suggested by the DIG High Prime DNA Labeling and Detection Starter Kit I manufacturer (Roche). Pre-hybridization was carried out in the supplied pre-hybridization solution for 1 hour at 50° C. For hybridization, 1 µg of denatured DNA (at 90° C. for 10 minutes) was added to fresh pre-hybridization solution pre-warmed to 50° C. After overnight hybridization, membranes were washed as follows: two washes with 2×SSC, 0.1% SDS, at room temperature for 5 minutes, and two washes with 0.5×SSC, 0.1% SDS at 55° C. for 15 minutes.

iii) Immunological detection: The hybridized probes were immunodetected with anti-digoxigenin-AP Fab fragments and visualized with the colorimetric substrates NBT/BCIP, as suggested by the DIG High Prime DNA Labeling and Detection Starter Kit I supplier (Roche).

iv) Analysing the expected bands, true secondary recombinants derived by pKC1139-ccrTs vector were confirmed by described Southern hybridization procedure. The ccr-disrupted strain *S. tsukubaensis* F130 was selected for further testing on tacrolimus and ascomycin production.

g) Fermentative tacrolimus production of thiostrepton resistant ccr disrupted mutants derived by secondary homologous recombination using pKC1139-ccrTs.
i) Seed culture Process: Seed medium comprised:

|  |  |  |
|---|---|---|
| Soy meal | 2.5 | grams |
| Dextrin | 10 | grams |
| Glucose | 1 | gram |
| Yeast extract | 5 | grams |
| Casein hydrolyzate | 7 | grams |
| $K_2HPO_4$ | 0.2 | gram |
| NaCl | 0.5 | gram |
| $MnCl_2 \times 4H_2O$ | 0.005 | gram |
| $FeSO_4 \times 7H_2O$ | 0.025 | gram |
| $ZnSO_4 \times 7H_2O$ | 0.001 | gram |
| $MgSO_4 \times 7H_2O$ | 0.005 | gram |
| $CaCl_2$ | 0.02 | gram |
| Final volume | 1 | liter |

The pH was adjusted to 7.0 with 1 M NaOH. 50 ml of this medium without glucose was filled into a 250 ml Erlenmeyer flask, closed with a foam plug and sterilized. Sterilization was performed at 121±2° C., 120±10 kPa for 25 minutes. After sterilization sterile glucose suspension was added. The sterilized Seed medium 50 μg/ml thiostrepton was added and spores of *Streptomyces tsukubaensis* strains (1% v/v) were inoculated in seed medium and incubated on shaker at 28° C. and 250 rpm for 24-48 hours under aerobic conditions.

ii) Main Fermentation Process: About 10% v/v of the above seed culture was used for the inoculation of a 250 ml Erlenmeyer flask, which contained 50 ml of Fermentation medium. The Fermentation medium contained:

|  |  |  |
|---|---|---|
| Dextrin | 90 | grams |
| Glucose | 5 | grams |
| Soy meal | 10 | grams |
| Soy peptone | 10 | grams |
| Glycerol | 10 | grams |
| L-lysine | 2.5 | gram |
| $K_2HPO_4$ | 1 | gram |
| $CaCO_3$ | 1.5 | grams |
| PEG (1000) | 1 | gram |
| Final volume | 1 | liter |

The pH of the Fermentation medium was adjusted before sterilization to pH 7.0 with 1M NaOH. Sterilization was performed at 121° C. for 25 minutes. Fermentation was carried out on shaker at 28° C., 250 rpm for 6-7 days.

h) Determination of tacrolimus and ascomycin production with HPLC of thiostrepton resistant ccr disrupted mutants derived by secondary homologous recombination using pKC1139-ccrTs.:
Method for tacrolimus and ascomycin determination: The analysis for determination of tacrolimus or ascomycin production thereof was carried out by isocratic reversed phase HPLC using an appropriate column and running conditions: column Nucleosil-100 C18 (150×4.0 mm, particle size 3 μm), flow 1.5 ml/min, T° C.=60° C., mobile phase: 560 ml water, 335 ml acetonitrile, 70 ml MTBE and 0.2 ml 85% $H_3PO_4$, detection 210 nm, sample injection 20 μl.

The tacrolimus and ascomycin content in samples quantification was performed by using external standards of tacrolimus and ascomycin, where tacrolimus was eluted at 12.5 min and ascomycin at 11.5 min. Results are expressed as % of ascomycin production compared to tacrolimus production in samples.

Sample preparation: To 5 ml of well shaken broth 5 ml of methanol was added and samples were placed on a shaker for 1 hour to extract samples. After extraction, 1 ml of methanol extract of broth was taken to 1.5 ml tube and centrifuged for 10 min at 14000 rpm. 0.8 ml of supernatant was transferred into vials and to perform HPLC analysis.

| Description of strain | Tacrolimus production (mg/l) | % of ascomycin production compared to tacrolimus production |
|---|---|---|
| NRRL 18488 (w.t.) | 43.4 ± 7.4 | 10.1 ± 1.6 |
| Δccr Ts[a] | 33.5 ± 13.4 | 6.4 ± 1.0 |

[a]Secondary recombinant mutants with disrupted ccr gene by integrated thiostrepton cassette. Mutants derived by secondary homologous recombination using pKC1139-ccrTs.

Isolated secondary recombinant mutants with disrupted ccr gene showed in average 40% reduction of ascomycin production compared to the wild type strain *Streptomyces tsukubaensis* NRRL 18488.

Example 5

Construction of Vectors for Disruption of the AIIR Gene, Construction of Mutant Strains of *S. tsukubaensis* NRRL 18488 with Inactivated AIIR and Analysis of Tacrolimus and Ascomycin Production of the Said Mutants a) Design of primers: As described in Example 4, a 454-based whole genome sequencing was used on the genome of *S. tsukubaensis*, which allowed us to design primers for amplification of the regions flanking the AIIR gene, based on a known DNA sequence of the region flanking the AIIR gene. Thus, AIIR-F1 (CAAGCTTCACCGGTCCCGGGCTC) (SEQ ID NO: 24) with a HindIII restriction site and AIIR-R1 (GCATATGGTCCGGTTCGGGGGTGGG) (SEQ ID NO: 25) with an NdeI restriction site were made to amplify the upstream region of the AIIR gene, and AIIR-F2 (GGGTCACATATGGCGAACTACCGGG) (SEQ ID NO: 26) with an NdeI and AIIR-R2 (CGAATTCT-GTGGGCCGACCTCACCCA) (SEQ ID NO: 27) with an EcoRI restriction site were made to amplify the downstream region of AIIR gene. Between primers AIIR-R1 and AIIR-F2, an 894 bp (298 amino acid) gap was generated for the deletion of almost entire 1335 bp AIIR gene. When the two overlapping fragments are combined at NdeI restriction site, the reading frame is preserved, which allows for an "in-frame" deletion of the target AIIR gene with a minimum impact on the downstream genes.

b) PCR amplification of DNA fragments: *S. tsukubaensis* genomic DNA obtained in Example 2 was PCR amplified using a Biorad iCycler Thermal Cycler using the same conditions as described in the paragraph ii of Example 4, using AIIR-F1+AIIR-R1 and AIIR-F2+AIIR-R2 primer combinations. The PCR-amplified products were cloned into a pUC19 cloning vector, and the sequence analysis of cloned PCR products confirmed their respective DNA sequence.

c) Construction of a temperature-sensitive pKC1139-based and suicide pKC1132-based vectors to be used in the disruption of the *S. tsukubaensis* AllR gene by homologous recombination: The F1-R1 and F2-R2 amplified fragments of the flanking regions of the AllR gene were excised from pUC19 by restriction enzymes HindIII and NdeI, and EcoRI and NdeI, respectively. Vectors pKC1139 and pKC1132 were previously cut with EcoRI and HindIII restriction enzymes, and the two fragments were combined and ligated into each of the target vector, making pKC1139-AllR and pKC1132-AllR, respectively. Vectors pKC1139-AllR and pKC1132-AllR were then opened using NdeI restriction enzyme, as described in paragraph iv of Example 4, and antibiotic resistance conferring cassette was inserted. For AllR, different cassettes were used; thiostrepton (Ts) resistance cassette was obtained from the p330 vector as described in Example 4, erythromycin (Er) resistance cassette was obtained from pIJ4026 vector by digesting the vector with EcoRI and XbaI and blunt-ending the 1690 bp long fragment, and kanamycin (Kn) resistance cassette was obtained from pSuperCos1 (REFI) vector by digesting the vector with SmaI and HindIII and blunt-ending the 1323 bp long fragment. Each of the cassettes was ligated into the open pKC1132-AllR and pKC1139-AllR vectors, making pKC1132-AllRTs, pKC1132-AllREr, pKC1132-AllRKn, pKC1139-AllRTs, pKC1139-AllREr, and pKC1139-AllRKn vectors, respectively.

d) Introduction of vectors for disruption of the AllR gene into the *S. tsukubaensis* NRRL 18488 strain: Plasmid constructs pKC1139-AllRTs, pKC1139-AllREr, and pKC1139-AllRKn were introduced into *S. tsukubaensis* NRRL 18488 strain by the same conjugation procedure as described in Example 4d.

e) Selection for stable secondary recombinant strains of *S. tsukubaensis* with disrupted AllR gene by antibiotic resistance conferring cassette: The procedure for selecting stable secondary recombinant strains of *S. tsukubaensis* with disrupted AllR gene by thiostrepton antibiotic conferring cassette for *S. tsukubaensis* exconjugants of vectors pKC1139-AllRTs, pKC1139-AllREr and pKC1139-AllRKn pKC1139-ccrTs was the same as described in Example 6. Subcultivation was carried out in liquid TSB medium with the corresponding antibiotic for which the resistance cassette is inserted between the flanking regions of the AllR gene. Selected secondary recombinant strains were no longer able to grow on apramycin, but were able to grow on the secondary antibiotic for which the resistance cassette is inserted between the flanking regions of the AllR gene.

f) Introduction of vectors for disruption of the AllR gene into the *S. tsukubaensis* F130 strain already conferring inactivated ccr-gene: Plasmid pKC1139-AllREr and pKC1139-AllRKn were introduced into *S. tsukubaensis* F130 ccr-disrupted strain, described in Example 4, by the same conjugation procedure as described in Example 4d.

g) Selection for stable secondary recombinant strains of *S. tsukubaensis* with disrupted ccr gene by thiostrepton resistance conferring cassette and disrupted AllR gene by erythromycin resistance conferring cassette: The procedure for selecting stable secondary recombinant strains of *S. tsukubaensis*, derivatives of *S. tsukubaensis* F130, with disrupted both ccr as well as AllR genes was the same as described in Example 4e. Subcultivation was carried out in liquid TSB medium with the corresponding antibiotic for which the resistance cassette is inserted between the flanking regions of the AllR gene. Selected secondary recombinant strains were no longer able to grow on apramycin, but were able to grow both thiostrepton (disrupting the ccr gene) as well as on the secondary antibiotic for which the resistance cassette is inserted between the flanking regions of the AllR gene.

h) Fermentative tacrolimus production of erythromycin resistant AllR disrupted mutants derived by secondary homologous recombination using pKC1139-AllREr: Tacrolimus production for erythromycin resistant AllR disrupted mutants was performed as described in Example 4g, except erythromycin 50 μg/ml was added to the Fermentation medium at the start of cultivation.

i) Fermentative tacrolimus production with double, ccr and AllR disrupted mutants: Tacrolimus production for erythromycin resistant ccr and AllR disrupted mutants was carried out as described in Example 4g, except thiostrepton and erythromycin ware added at the concentration of 50 μg/ml, each, to the fermentation medium at the start of cultivation. For the feeding experiments, allymalonyl-CoA and ethylmalonyl-CoA precursors, diethyl allylmalonyl-SNAC, allylmalonyl-di-SNAC and ethylmalonyl-SNAC, were added to the Fermentation medium in at 5-20 mM concentration.

j) Determination of tacrolimus and ascomycin production with HPLC of erythromycin resistant AllR disrupted mutants derived by secondary recombination using pKC1139-AllREr:

For the determination of tacrolimus and ascomycin production of erythromycin resistant AllR disrupted mutants was used the same method as described in Example 4h.

| Description of strain | Tacrolimus production (mg/l) | Ascomycin production (mg/l) | Dihydrotacrolimus production (mg/l) |
|---|---|---|---|
| NRRL 18488 (w.t.) | 30.0 ± 6.6 | 3.2 ± 0.6 | <1.0 |
| ΔallR Er[a] | 0.0 | 0.0 | 0.0 |
| ΔallR Er[a] + allylmalonyl-SNAC | 8.1 ± 2.3 | 0.0 | 0.0 |
| ΔallR Er[a] + allylmalonyl-diSNAC | 7.5 ± 2.0 | 0.0 | 0.0 |
| ΔallR Er[a] + ethylmalonyl-CoA precursor | 0.0 | 10.2 ± 3.2 | 0.0 |

[a]Secondary recombinant mutants with disrupted allR gene by integrated erythromycin cassette. Mutants derived by secondary homologous recombination using pKC1139-allREr.

Isolated secondary recombinant mutants with disrupted AllR gene caused complete abolishment of tacrolimus production. When allylmalonyl-SNAC or alllymalonyl-diSNAC were added to the Fermentation medium, production of tacroliomus was re-established. Similarly, when ethylmalonyl-SNAC was added, ascomycin production was re-established.

k) Determination of tacrolimus and ascomycin production with HPLC of double, ccr and AllR disrupted mutants:

For the determination of tacrolimus and ascomycin production of double, ccr and AllR disrupted mutants, method as described in Example 4h was used.

| Description of strain | Tacrolimus production (mg/l) | Ascomycin production (mg/l) | Dihydrotacrolimus production (mg/l) |
|---|---|---|---|
| NRRL 18488 (w.t.) | 36.9 ± 9.9 | 3.5 ± 1.2 | <1.0 |
| Δccr allR[a] | 0.0 | 0.0 | 0.0 |
| Δccr allR[a] + allylmalonyl-CoA precursor | 7.8 ± 2.0 | 0.0 | 0.0 |
| Δccr allR[a] + allylmalonyl-CoA precursor | 6.9 ± 2.2 | 0.0 | 0.0 |
| Δccr allR[a] + ethylmalonyl-CoA precursor | 0.0 | 11.8 ± 2.1 | 0.0 |

[a]Secondary recombinant mutants with disrupted ccr and allR genes by integrated erythromycin cassette. Mutants derived by secondary homologous recombination using pKC1139-allREr.

Complete abolishment of tacrolimus occurred with isolated secondary recombinant mutants with inactivated ccr and AllR genes. When allylmalonyl-SNAC or allymalonyl-diSNAC were added to the Fermentation medium, production of tacroliomus was re-established. Similarly, when ethylmalonyl-SNAC was added, ascomycin production was re-established.

Example 6

Construction of Vectors for Disruption of the aIIK Gene, Construction of Mutant Strains of S. tsukubaensis NRRL 18488 with Inactivated aIIK and Analysis of Tacrolimus and Ascomycin Production of the Said Mutants a) Design of primers: a 454-based whole genome sequencing was used on the genome of S. tsukubaensis, which allowed us to design primers for amplification of the regions flanking the aIIK gene, based on the known DNA sequence of the region flanking the aIIK gene. Thus, aIIK-F1 (AGAATTCGTTACGGGGAGACGGCATCCCGG) (SEQ ID NO: 28) with an EcoRI restriction site and aIIK-R1 (AGGATCCGGGCGGGCTCGTCGCGGT) (SEQ ID NO: 29) were made to amplify the upstream region of the aIIK gene containing an internal BamHI restriction site, and aIIK-F2 (TGGATCCGGCGCGTATCGCCAACCGCTAC) (SEQ ID NO: 30) with a BamHI and aIIK-R2 (AAAGCTTCCCGGTAGTTCGCCATATGTGACCCG) (SEQ ID NO: 31) with a HindIII restriction site were made to amplify the downstream region of the aIIK gene. Between the internal BamHI restriction site and aIIK-F2, a 1698 bp (566 amino acid) gap was generated for the deletion of almost entire 2388 bp aIIK gene. When the two overlapping fragments are combined at BamHI restriction site, the reading frame is preserved, which allows for deletion of the target aIIK gene with a minimum impact on the downstream genes.

b) PCR amplification of DNA fragments: S. tsukubaensis genomic DNA obtained in Example 2 was PCR amplified using a Biorad iCycler Thermal Cycler using the same conditions as described in the paragraph ii of Example 4b, using aIIK-F1+aIIK-R1 and aIIK-F2+aIIK-R2 primer combinations. The PCR-amplified products were cloned into a pUC19 cloning vector, and the sequence analysis of cloned PCR products confirmed their respective DNA sequence.

c) Construction of a temperature-sensitive pKC1139-based and suicide pKC1132-based vectors to be used in the disruption of the S. tsukubaensis aIIK gene by homologous recombination: The F1-R1 and F2-R2 amplified fragments of the flanking regions of the aIIK gene were excised from pUC19 by restriction enzymes EcoRI and BamHI and HindII and BamHI, respectively. Vectors pKC1139 and pKC1132 were previously cut with EcoRI and HindIII restriction enzymes, and the two fragments were combined and ligated into each of the target vector, making pKC1139-aIIK and pKC1132-aIIK, respectively.

d) Introduction of vector for in-frame disruption of the aIIK gene into the S. tsukubaensis NRRL 18488 strain: Plasmid construct pKC1139-aIIK was introduced into S. tsukubaensis NRRL 18488 strain by the same conjugation procedure as described in Example 4d.

e) Selection for stable secondary recombinant strains of S. tsukubaensis with disrupted aIIK gene: S. tsukubaensis exconjugants of vector pKC1139-aIIK, grown at 28° C. on Sporulation medium with addition of 50 μg/ml apramycin were inoculated into liquid TSB medium and grown in shake flasks at 28° C. and 210 rpm with the addition of 50 μg/ml apramycin to produce good seed culture. After 24 h, seed culture was subcultivated into a new shake flask with fresh TSB medium with the addition of 50 μg/ml apramycin and grown at an increased temperature, higher than 34° C., and 210 rpm. Above 34° C. the pKC1139-based vector is unable to replicate and is forced to integrate into the S. tsukubaensis genome, thus yielding primary recombinants. The culture was then subcultivated several times into new shake flasks with fresh TSB medium without apramycin, allowing the pKC1139-based vector to be removed by homologous recombination, then plated onto the Sporulation medium and grown at 28° C. Harvested spores were filtered and serial dilution was made on plates of Sporulation medium. After 5-8 days, single colonies were patched onto plates with Sporulation medium, and on plates of Sporulation medium with apramycin. Primary recombinants are still resistant to apramycin, while secondary recombinants lost the apramycin resistance and cannot grow on Sporulation medium with apramycin. True secondary recombinant mutants with the desired in-frame deletion of the aIIK gene were identified against wild type revertants using Southern hybridization as described in Example 4f.

f) Fermentative tacrolimus production of aIIK disrupted mutants derived by secondary homologous recombination using pKC1139-aIIK: Tacrolimus production for aIIK disrupted mutants was performed as described in example 4g with no antibiotic added to growth media.

g) Fermentative tacrolimus production with aIIK disrupted mutants: Tacrolimus production aIIK disrupted mutants was carried out as described in example 4g. For the feeding experiments, allymalonyl-CoA and ethylmalonyl-CoA precursors, allylmalonyl-SNAC, allylmalonyl-diSNAC and ethylmalonyl-SNAC, were added to the Fermentation medium at 5-20 mM concentration.

h) Determination of tacrolimus and ascomycin production with HPLC of aIIK disrupted mutants derived by secondary recombination using pKC1139-aIIK: For the determination of tacrolimus and ascomycin production of aIIK disrupted mutants the same method was used as described in Example 4h.

| Description of strain | Tacrolimus production (mg/l) | Ascomycin production (mg/l) | Dihydrotacrolimus production (mg/l) |
|---|---|---|---|
| NRRL 18488 (w.t.) | 36.8 ± 4.3 | 3.4 ± 0.6 | <1.0 |
| ΔallK[a] | 0.0 | 3.7 ± 0.5 | 0.0 |
| ΔallK[a] + allylmalonyl-SNAC | 8.3 ± 2.2 | 2.2 ± 0.6 | 0.0 |
| ΔallK[a] + allylmalonyl-diSNAC | 7.1 ± 2.1 | 3.8 ± 0.5 | 0.0 |
| ΔallK[a] + ethylmalonyl-SNAC | 0.0 | 11.8 ± 2.6 | 0.0 |

[a]Secondary recombinant mutants with disrupted allK gene. Mutants derived by secondary homologous recombination using pKC1139-allK.

Isolated secondary recombinant mutants with disrupted allK gene caused complete abolishment of tacrolimus and dihydrotacrolimus production. When allylmalonyl-SNAC or allylmalonyl-diSNAC were added to the Fermentation medium, production of tacroliomus was re-established. Similarly, when ethylmalonyl-SNAC was added, ascomycin production was substantially increased.

Example 7

Construction of Vectors for Overexpression of the AIIP Gene, Construction of Mutant Strains of *S. tsukubaensis* NRRL 18488 with Overexpressed AIIP and Analysis of Tacrolimus and Ascomycin Production of the Said Mutants a) Chemical synthesis of the AIIP gene: The DNA sequence of the genome of *S. tsukubaensis* NRRL 18488, based on a 454-whole genome sequencing was used to design and synthesize the DNA sequence of the AIIP gene conferring NdeI restriction site at the 5'-end of the ORF and Xba I restriction site at the 3'-end of the ORF.
b) Construction of a pSET152-based expression vector for overexpression of the AIIP gene: The synthesized AIIP gene was cut by restriction enzymes NdeI and XbaI. Erm* promoter sequence was previously introduced into the multiple cloning site of the pSET152 vector using EcoRI and XbaI restriction sites generating a NdeI site to the 3'-end of the promoter sequence. This vector was cut with NdeI and XbaI and ligated with the NdeI and XbaI fragment of the AIIP gene to generated pSET-152-AIIP plasmid.
c) Overexpression of the AIIP gene into the *S. tsukubaensis* NRRL 18488 strain:
Plasmid construct pSET152-AIIP was introduced into *S. tsukubaensis* NRRL 18488 strain by conjugation procedure as described in Example 4d.
d) Determination of tacrolimus and ascomycin production of *S. tsukubaensis* mutants conferring pSET152-AIIP plasmid.
For the determination of tacrolimus and ascomycin production HPLC method was used as described in Example 4h.

| Description of strain | Tacrolimus production (mg/l) | % of ascomycin production compared to tacrolimus production |
|---|---|---|
| NRRL 18488 (w.t.) | 31.2 ± 14.6 | 12.7 ± 3.0 |
| Strains with overexpressed AIIP gene | 39.3 ± 12.0 | 12.1 ± 3.2 |

Isolated recombinant mutants with in which AIIP gene was over expressed showed 25% increased tacrolimus production compared to the wild type strain *Streptomyces tsukubaensis* NRRL 18488.

Example 8

Construction of Vectors for Over Expression of the Ecm Gene, Construction of Mutant Strains of *S. tsukubaensis* NRRL 18488 with Ecm Gene Over Expressed and Analysis of Tacrolimus and Ascomycin Production of the Said Mutants a) Chemical synthesis of the ecm gene: The DNA sequence of the genome of *S. tsukubaensis* NRRL 18488, based on a 454-whole genome sequencing was used to design and chemically synthesize the DNA sequence of the ecm gene conferring NdeI restriction site at the 5'-end of the ORF and XbaI restriction site at the 3'-end of the ORF.
b) Construction of a pSET152-based expression vector for over expression of the AIIP gene: The synthesized ecm gene fragment was cut by restriction enzymes NdeI and XbaI. Erm* promoter sequence was previously introduced into the multiple cloning site of the pSET152 vector using EcoRI and XbaI restriction sites adding a NdeI site to the 3'-end of the promoter sequence. This vector was cut with NdeI and XbaI and ligated with the NdeI and XbaI fragment of the AIIP gene to generate pSET-152-ecm construct.
c) Introduction of vector for over expression of the ecm gene into the *S. tsukubaensis* NRRL 18488 strain:
Plasmid construct pSET152-ecm was introduced into *S. tsukubaensis* NRRL 18488 strain by conjugation procedure as described in Example 4d.
d) HPLC analysis of tacrolimus and ascomycin production in ecm over expressing mutants
For the determination of tacrolimus and ascomycin production of ecm over expressing mutants method was used as is described in Example 4h.

| Description of strain | Tacrolimus production (mg/l) | % of ascomycin production compared to tacrolimus production |
|---|---|---|
| NRRL 18488 (w.t.) | 31.6 ± 11.7 | 9.3 ± 2.8 |
| Strains with overexpressed ecm gene | 31.4 ± 8.5 | 7.5 ± 2.6 |

Isolated recombinant mutants with over expressed ecm gene showed 20% reduced ascomycin production compared to the wild type strain *Streptomyces tsukubaensis* NRRL 18488.

Example 9

Construction of a Vector for Overexpression of aIIA and aIIK Genes, Complementation of aIIK-Inactivated Strains of *S. tsukubaensis* NRRL 18488 with this Vector and Analysis of Tacrolimus and Ascomycin Production of the Said Mutants a) Design of primers: As described in Example 4, a 454-based whole genome sequencing was used on the genome of *S. tsukubaensis*, which allowed us to design primers for amplification of the region of all subcluster from aIIA to aIID gene. Thus, AT-exp-F1 (ACATAT-GCTCGGGTCGTTCGTTACGGGGAG) (SEQ ID NO:

32) with a NdeI restriction site and AT-exp-R1 (ATCTA-GAACGTGGGTCATCGGCTGGTCCTTG) (SEQ ID NO: 33) with an XbaI restriction site were made to amplify these two ORFs (aIIA and aIIK).

b) PCR amplification of DNA fragments: *S. tsukubaensis* genomic DNA obtained in Example 2 was PCR amplified using a Biorad iCycler Thermal Cycler. The PCR reaction was carried out with Phusion polymerase (Finnzymes) and the buffer provided by the manufacturer in the presence of 200 µM dNTP, 3% DMSO, 0.5 µM of each primer, approximately 50 ng of template *S. tsukubaensis* genomic DNA and 2.5 units of enzyme in a final volume of 50 µl for 30 cycles. The thermal profile of the first 5 cycles was 98° C. for 15 sec (denaturation step), 65° C. for 30 sec (annealing step), and 72° C. for 3 min 15 sec (extension step). The thermal profile of the remaining 25 cycles was 98° C. for 15 sec (denaturation step), 60° C. for 30 sec (annealing step), and 72° C. for 3 min 15 s (extension step). The PCR-amplified product was cloned into a pUC19 cloning vector. The sequence analysis of the cloned PCR product confirmed the sequence of aIIA and aI/K genes.

c) Construction of a pSET152-based expression vector for overexpression of aIIA and aI/K genes: The 3.9 kb insert was cut from pUC19 vector by restriction enzymes NdeI and XbaI. ErmE* promoter sequence was previously introduced into the multiple cloning site of the pSET152 vector using EcoRI and XbaI restriction sites generating a NdeI site to the 3'-end of the promoter sequence. This vector was cut with NdeI and XbaI and subsequently ligated with the NdeI and XbaI fragment containing aIIA and aI/K genes to generate pSET152-ermE*-aIIA-K plasmid.

d) Introduction of the aIIA and aIIK gene into the *S. tsukubaensis* strain with inactivated aliK gene, obtained in Example 6: plasmid construct pSET152-ermE*-aIIA-K was introduced into the aIIK-inactivated strain of *S. tsukubaensis* NRRL 18488 by conjugation procedure as described in Example 4d.

e) Fermentative tacrolimus production of aIIK disrupted mutants transformed with a pSET152-ermE*-aIIA-K vector: Tacrolimus production for transformed mutants was performed as described in example 4g with no antibiotic added to growth media.

f) Determination of tacrolimus and ascomycin production of aIIK-inactivated *S. tsukubaensis* mutants conferring pSET152-ermE*-aIIA-K plasmid

| Description of strain | Tacrolimus production (mg/l) | Ascomycin production (mg/l) |
| --- | --- | --- |
| NRRL 18488 (w.t.) | 37.7 ± 19.3 | 3.4 ± 1.8 |
| ΔaIIK | 0.0 | 2.6 ± 1.1 |
| ΔaIIK strains with overexpressed aIIA and aIIK genes | 24.7 ± 14.1 | 3.4 ± 1.6 |

Isolated recombinant mutants of aIIK-inactivated strains in which the loss of aIIK gene activity was complemented by overexpression of aIIA and aIIK showed restored production of tacrolimus.

Example 10

Construction of a Vector for Overexpression of aIIA, aIIK, aIIR, aIID Genes, Complementation of aIIR-Inactivated Strains of *S. tsukubaensis* NRRL 18488 with this Vector and Analysis of Tacrolimus and Ascomycin Production of the Said Mutants a) Design of primers: As described in Example 4, a 454-based whole genome sequencing was used on the genome of *S. tsukubaensis*, which allowed us to design primers for amplification of the region of all subcluster from aIIA to aIID gene Thus, AT-exp-F1 (ACATAT-GCTCGGGTCGTTCGTTACGGGGAG) (SEQ ID NO: 32) with a NdeI restriction site and AT-exp-R2 (ATCTA-GAACATGCCCTAGGTACGTTTCGCGG) (SEQ ID NO: 34) with an XbaI restriction site were made to amplify these four ORFs (aIIA, aIIK, aIIR, and aIID).

b) PCR amplification of DNA fragments: *S. tsukubaensis* genomic DNA obtained in Example 2 was PCR amplified using a Biorad iCycler Thermal Cycler. The PCR reaction was carried out with Phusion polymerase (Finnzymes) and the buffer provided by the manufacturer in the presence of 200 µM dNTP, 3% DMSO, 0.5 µM of each primer, approximately 50 ng of template *S. tsukubaensis* genomic DNA and 2.5 units of enzyme in a final volume of 50 µl for 30 cycles. The thermal profile of the first 5 cycles was 98° C. for 15 sec (denaturation step), 65° C. for 30 sec (annealing step), and 72° C. for 3 min 15 sec (extension step). The thermal profile of the remaining 25 cycles was 98° C. for 15 sec (denaturation step), 60° C. for 30 sec (annealing step), and 72° C. for 3 min 15 sec (extension step). The PCR-amplified product was cloned into a pUC19 cloning vector. The sequence analysis of the cloned PCR product confirmed the sequence of aIIA, aIIK, aIIR and aIID genes.

c) Construction of a pSET152-based expression vector for overexpression of aIIA, aIIK, aIIR and aIID genes: The 6.4 kb insert was cut from pUC19 vector by restriction enzymes NdeI and XbaI. ErmE* promoter sequence was previously introduced into the multiple cloning site of the pSET152 vector using EcoRI and XbaI restriction sites generating a NdeI site to the 3'-end of the promoter sequence. This vector was cut with NdeI and XbaI and subsequently ligated with the NdeI and XbaI fragment containing aIIA, aIIK, aIIR and aIID genes to generate pSET152-ermE*-aIIA-D plasmid.

d) Introduction of the aIIA, aIIK, aIIR and aIID gene into the *S. tsukubaensis* strain with inactivated aIIR gene, obtained in Example 5: plasmid construct pSET152-ermE*-aIIA-D was introduced into the aI/R-inactivated strain of *S. tsukubaensis* NRRL 18488 by conjugation procedure as described in Example 4d.

e) Fermentative tacrolimus production of aIIR inactivated mutants transformed with a pSET152-ermE*-aIIA-D vector: Tacrolimus production for transformed mutants was performed as described in example 4g with no antibiotic added to growth media.

f) Determination of tacrolimus and ascomycin production of aIIR-inactivated *S. tsukubaensis* mutants conferring pSET152-ermE*-aIIA-D plasmid

| Description of strain | Tacrolimus production (mg/l) | Ascomycin production (mg/l) |
|---|---|---|
| NRRL 18488 (w.t.) | 36.1 ± 20.2 | 4.4 ± 1.5 |
| ΔallR Er$^r$ | 0.0 | 0.0 |
| ΔallR Er$^r$ strains with overexpressed allA, allK, allR and allD genes | 15.2 ± 7.7 | 3.0 ± 1.0 |

Isolated recombinant mutants of allR-inactivated strains in which the loss of allR gene activity was complemented by overexpression of allA, allK, allR and allD showed restored production of tacrolimus and ascomycin.

Example 11

Introduction of the Plasmid pSET152-ermE*-allA-D into the Strain *Streptomyces hygroscopicus* Var. *Ascomyceticus* ATCC14891, Overexpression of allA, allK, allR and allD Genes in this Strain and Analysis of Tacrolimus and Ascomycin Production of the Said Mutants a) Construction of a pSET152-based expression vector for overexpression of allA, allK, allR and allD genes: pSET152-ermE*-allA-D plasmid was prepared as described in Example 10.

b) Introduction of the allA, allK, allR and allD genes into the strain *Streptomyces hygroscopicus* var. *ascomyceticus* ATCC14891: Plasmid construct pSET152-ermE*-allA-D was introduced by transformation into electrocompetent *E. coli* strain ET12567 containing the conjugative plasmid pUZ8002 (Paget et al., 1999 J. Bacteriol. 181: 204-211). The plasmid pUZ8002 contains all the necessary genes for construction of conjugative pilli, however it lacks the origin of transfer and, thus, remains in the host cell (Jones et al., 1997 Mol. Microbiol. 23:169-178). Conjugation procedure of *Streptomyces hygroscopicus* var. *ascomyceticus* ATCC14891 was done as described in Kieser et al., 2000 (Practical *Streptomyces* genetics, A laboratory Manual. ISBN0-7084-0623-8). Exconjugants were grown at 28° C. on Sporulation medium which is described in Example 1 with addition of 50 μg/ml apramycin.

c) Fermentative ascomycin and tacrolimus production of strains transformed with a pSET152-ermE*-allA-D vector: Fermentation process for ascomycin and tacrolimus production of transformed mutants was performed as described in example 4g with no antibiotic added to growth media.

d) Determination of tacrolimus and ascomycin production with LC-MS/MS of *Streptomyces hygroscopicus* var. *ascomyceticus* ATCC14891 mutants overexpressing the allA, allK, allR and allD genes:

Sample preparation: To 5 ml of well shaken broth 5 ml of methanol was added and samples were placed on a shaker for 1 hour to extract samples. After extraction, 1 ml of methanol extract of broth was taken to 1.5 ml tube and centrifuged for 10 min at 14000 rpm. 0.8 ml of supernatant was transferred into vials and to perform LC-MS/MS analysis.

Figure 2:
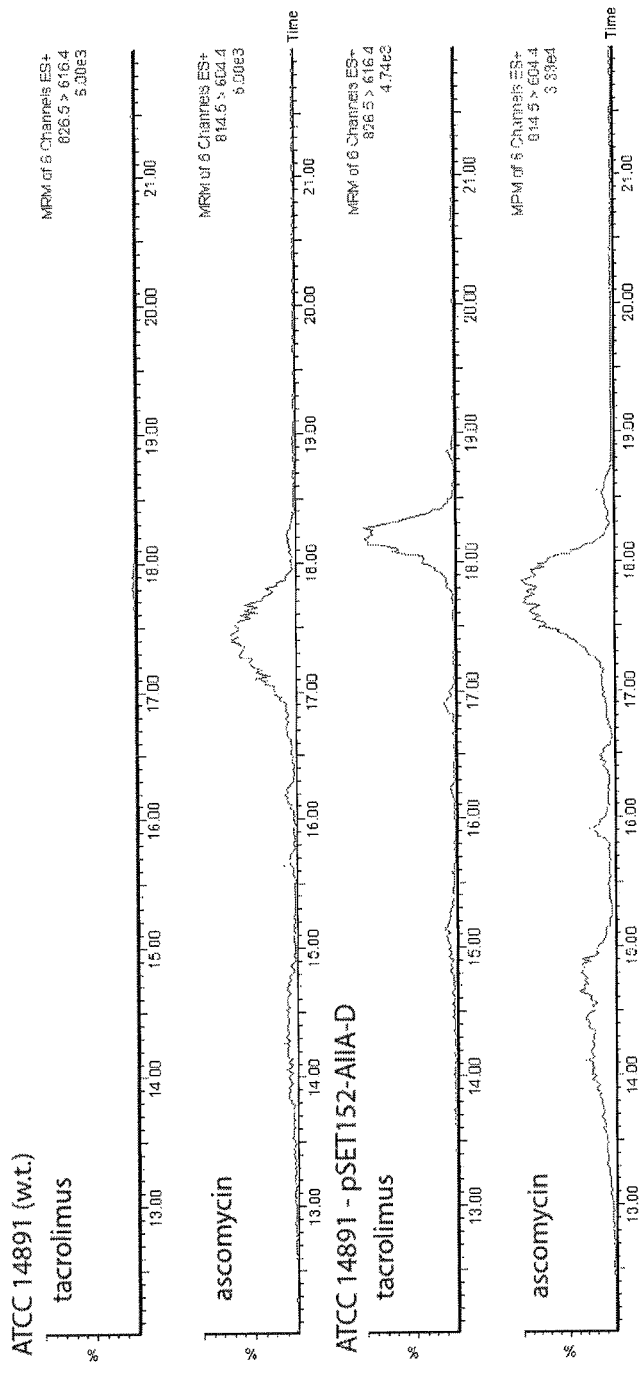
FIG. 2 shows LC-MS chromatograms (MRM) for monitoring the presence of tacrolimus and ascomycin in extracted fermentation broths of *Streptomyces hygroscopicus* var. *ascomyceticus* ATCC 14891. Ascomycin is produced by the wild type strain (row 2) and a mutant strain overexpressing the aIIA, aIIK, aIIR and aIID genes (row 4). On the other hand, tacrolimus is not produced by the wild type strain (row 1) and is only produced when the aIIA, aIIK, aIIR and aIID are overexpressed (row 3).

Method for tacrolimus and ascomycin determination: Identity of FK506 and FK520 in cultivation broths was determined by LC-MS/MS analysis. We used the Agilent 1100 series LC-MS system coupled with Watters Micromass Quattro micro detector using reversed phase column (Gemini C18 column, 5 μm, 150 mm×2 mm i.d.) from Phenomenex. The separation was performed at a flow rate of 0.250 ml/min by gradient elution with 0.5% TFA as solvent A and acetonitrile as solvent B. The gradient program was: 60% A, 0 min; 60-20% A, 0-17 min; 20-60% A, 17-18 min; 60% A, 18-30 min and the injection volume 10 μL at temperature of the column 45° C. was used. The mass selective detector (Waters, Quattro micro API) was equipped with an electrospray ionisation using a cone voltage of 20 V and capillary voltage of 3.5 kV for positive ionization of the analytes. Dry nitrogen was heated to 350° C., the drying gas flow was 400 l/h and collision energy was 20 eV. In ESI$^+$ positive mode, an ion of m/z=826.5 that corresponds to a capture of a sodium ion of FK506 ([M+Na]$^+$) was most intensive, in accordance with the results of other investigators (see Yuan J. et al. 2008, J. Chromatogr., B: Anal. Technol. Biomed Life Sci. 868, 34-41). For FK506 identity confirmation, multiple reaction-monitoring mode was used and the transition FK506 m/z 826.5 [M+Na]$^+$→m/z 616.4 was recorded. Analogously, for FK520 monitoring the transition m/z 814.5 [M+Na]$^+$→m/z 604.4 was recorded. Tacrolimus was eluted at approx. 18.2 min and ascomycin at approx. 17.5-17.7 min. Abundance of FK506 and FK520 could not be determined therefore only presence or absence of both compounds could be established (FIG. 2).

| Description of strain | Tacrolimus production | Ascomycin production |
|---|---|---|
| ATCC 18491 (w.t.) | absent | present |
| Strains with overexpressed allA, allK, allR and allD genes | present | present |

Isolated recombinant mutants of *Streptomyces hygroscopicus* var. *ascomyceticus* ATCC14891 in which allA, allK, allR and allD genes were overexpressed showed production of tacrolimus in addition to ascomycin which is usually produced by this strain.

Example 12

Construction of Vectors for Deletion of a Large Part of the all Subcluster (from allD to allS), Construction of Mutant Strains of *S. tsukubaensis* NRRL 18488 with this Part of the all Subcluster Deleted and Analysis of Tacrolimus and Ascomycin Production of the Said Mutants a) Design of primers: As described in Example 4, a 454-based whole genome sequencing was used on the genome of *S. tsukubaensis*, which allowed us to design primers for amplification of the regions flanking the region between allD and allS genes, based on a known DNA sequence of the region upstream of the allD gene and downstream of the allS gene. Thus, KS-delF2b (TGGATCCGGCGCGTATCGCCAACCGCTAC) (SEQ ID NO: 30) with a BamHI restriction site and AllRexpR1 (ATCTAGAGGCGTTCGGATTCGCTCACCG) (SEQ ID NO: IQ with an XbaI restriction site were made to amplify the region upstream of the allD gene, and ClusDelF2 (ATCTAGAGGGCGGATACGTCACCGGCG) (SEQ ID NO: 36) with an XbaI and ClusDelR2b (CCAAGCTTATGGAGATCATCGAAGGCAGC) (SEQ ID NO: 37) with an HindIII restriction site were made to amplify the region downstream of the allS gene. Between primers AllRexpR1 and ClusDelF2, a 6262 bp gap was generated for the deletion of allD, allM, allN, allP, allO and allS genes.

b) PCR amplification of DNA fragments: *S. tsukubaensis* genomic DNA obtained in Example 2 was PCR amplified using a Biorad iCycler Thermal Cycler. The PCR reaction was carried out with Phusion polymerase (Finnzymes) and the buffer provided by the manufacturer in the presence of 200 µM dNTP, 3% DMSO, 0.5 µM of each primer, approximately 50 ng of template *S. tsukubaensis* genomic DNA and 2.5 units of enzyme in a final volume of 50 µl for 30 cycles. The thermal profile of the first 5 cycles was 98° C. for 15 sec (denaturation step), 65° C. for 30 sec (annealing step), and 72° C. for 1 min (extension step). The thermal profile of the remaining 25 cycles was 98° C. for 15 sec (denaturation step), 60° C. for 30 sec (annealing step), and 72° C. for 1 min (extension step). The PCR-amplified products were cloned into a pUC19 cloning vector. The sequence analysis of the cloned PCR product confirmed the sequence of the amplified upstream and downstream regions.

c) Construction of a temperature-sensitive pKC1139-based vector to be used in the disruption of the aIID-aIIS region of the *S. tsukubaensis* genome by homologous recombination: The KS-delF2b-AIIRexpR1 and ClusDelF2-ClusDelR2 amplified fragments of the flanking regions were excised from pUC19 by restriction enzymes BamHI and XbaI and XbaI and HindIII, respectively. Vector pKC1139 was previously cut with BamHI and HindIII restriction enzymes, and the two fragments were combined and ligated into the target vector, making pKC1139-ClusDel.

d) Introduction of vector for deletion of the aIID-aIIS region of all subcluster into the *S. tsukubaensis* NRRL 18488 strain: Plasmid construct pKC1139-ClusDel was introduced into *S. tsukubaensis* NRRL 18488 strain by the same conjugation procedure as described in Example 4d.

e) Selection for stable secondary recombinant strains of *S. tsukubaensis* with deleted aIID-aIIS region: Selection of secondary recombinants was carried out using the same procedure as described in Example 6d.

f) Fermentative tacrolimus production of mutants with deleted aIID-aIIS region, derived by secondary homologous recombination using pKC1139-ClusDel: Fermentation process for tacrolimus production of the aIID-aIIS-deleted mutants was performed as described in example 4g with no antibiotic added to growth media.

g) Determination of tacrolimus and ascomycin production with HPLC of aIID-aIIS deleted mutants derived by secondary recombination using pKC1139-ClusDel: For the determination of tacrolimus and ascomycin production of aIID-aIIS-deleted mutants the same method was used as described in Example 4h.

| Description of strain | Tacrolimus production (mg/l) | Ascomycin production (mg/l) |
|---|---|---|
| NRRL 18488 (w.t.) | 37.7 ± 19.3 | 3.4 ± 1.8 |
| ΔalID-alIS[a] | 0.0 | 0.0 |

[a]Secondary recombinant mutants with deleted alID-alIS region. Mutants derived by secondary homologous recombination using pKC1139-ClusDel.

Isolated secondary recombinant mutants with disrupted aIID-aIIS region caused complete abolishment of tacrolimus and ascomycin production.

The invention claimed is:

1. A genetically modified strain of a microorganism belonging to the genus *Streptomyces*, wherein said microorganism comprises genes represented by SEQ ID NO: 2, SEQ ID NO: 3, SEQ ID NO: 4, SEQ ID NO: 5, SEQ ID NO: 6, SEQ ID NO: 7, SEQ ID NO:8, SEQ ID NO: 9 and SEQ ID NO: 10, which are involved in the metabolism and/or the biosynthesis of ethylmalonyl-CoA and/or allylmalonyl-CoA, wherein in said genetically modified strain of said microorganism, one or more of said genes is inactivated and/or over expressed.

2. The genetically modified strain of a microorganism according to claim 1, wherein said strain has a native or engineered polyketide synthase activity.

3. A process for the preparation of tacrolimus, wherein the process comprises the step of cultivating the genetically modified strain of claim 1.

4. The process according to claim 3, wherein the process is carried out under the external addition of allylmalonyl-CoA and/or at least one precursor of allylmalonyl-CoA.

5. A *Streptomyces tsukubaensis* strain deposited at Deutsche Sammlung von Microorganismen and Zellkulturen GmbH (Braunschweig, Germany) and having a deposit number selected from the group consisting of DSM 22507, DSM 22509, DSM22511, DSM 22506 and DSM 22510.

\* \* \* \* \*